(12) United States Patent
Kamiya et al.

(10) Patent No.: US 8,198,418 B2
(45) Date of Patent: Jun. 12, 2012

(54) NUCLEOSIDE TRIPHOSPHATE DERIVATIVE, NUCLEIC ACID PROBE, MULTILABELED NUCLEIC ACID PROBE, METHOD FOR PRODUCTION OF MULTILABELED NUCLEIC ACID PROBE, AND METHOD FOR DETECTION OF TARGET NUCLEIC ACID

(75) Inventors: Noriho Kamiya, Fukuoka (JP); Sumihare Noji, Tokushima (JP); Yoshiyuki Hiraishi, Mitaka (JP)

(73) Assignees: Kyushu University, National University Corporation, Fukuoka-shi, Fukuoka (JP); The University of Tokushima, Tokushima-shi, Tokushima (JP); Hitachi Aloka Medical, Ltd., Tokyo (JP)

( * ) Notice: Subject to any disclaimer, the term of this patent is extended or adjusted under 35 U.S.C. 154(b) by 0 days.

(21) Appl. No.: 13/003,380

(22) PCT Filed: Jul. 22, 2009

(86) PCT No.: PCT/JP2009/063454
§ 371 (c)(1),
(2), (4) Date: Jan. 10, 2011

(87) PCT Pub. No.: WO2010/010966
PCT Pub. Date: Jan. 28, 2010

(65) Prior Publication Data
US 2011/0189671 A1 Aug. 4, 2011

(30) Foreign Application Priority Data

Jul. 24, 2008 (JP) .................................. 2008-191343
Feb. 16, 2009 (JP) .................................. 2009-032763

(51) Int. Cl.
C07G 3/00 (2006.01)
C07H 19/04 (2006.01)
C07H 21/00 (2006.01)
C07H 21/02 (2006.01)
C12Q 1/68 (2006.01)
C12P 19/34 (2006.01)

(52) U.S. Cl. ...... 536/4.1; 536/23.1; 536/25.3; 536/26.6; 435/6; 435/91.1

(58) Field of Classification Search ................... 536/4.1, 536/23.1, 25.3, 26.6; 435/6, 91.1
See application file for complete search history.

(56) References Cited

U.S. PATENT DOCUMENTS
5,986,086 A 11/1999 Brush et al.
(Continued)

FOREIGN PATENT DOCUMENTS
JP 2000-504009 A 4/2000
(Continued)

OTHER PUBLICATIONS

Notification of Transmittal of Translation of the International Preliminary Report on Patentability (Form PCT/IB/338) of International Application No. PCT/JP2009/063454 mailed Mar. 10, 2011 with Form PCT/IPEA/409.
(Continued)

Primary Examiner — Jezia Riley
(74) Attorney, Agent, or Firm — Westerman, Hattori, Daniels & Adrian, LLP

(57) ABSTRACT

A novel nucleoside triphosphate derivative, a nucleic acid probe, and a multilabeled nucleic acid probe that can detect a target nucleic acid conveniently and with high sensitivity, as well as a method for producing the multilabeled nucleic acid probe, and a method for detecting a target nucleic acid using the multilabeled nucleic acid probe or the nucleic acid probe. A target nucleic acid can be detected conveniently and with high sensitivity by using a transglutaminase (TGase), and by using a multilabeled nucleic acid probe in which a plurality of labeling portions have been introduced in advance by covalent binding, or by introducing a plurality of labeling portions by covalent binding into a nucleic acid probe that has been hybridized with the target nucleic acid.

12 Claims, 23 Drawing Sheets

U.S. PATENT DOCUMENTS

| | | |
|---|---|---|
| 6,063,628 A | 5/2000 | Loeb et al. |
| 6,239,159 B1 | 5/2001 | Brown et al. |
| 6,340,747 B1 | 1/2002 | Bazin et al. |
| 6,482,938 B1 | 11/2002 | Hayashizaki et al. |
| 6,777,395 B2 | 8/2004 | Bhat et al. |
| 2002/0064782 A1 | 5/2002 | Shinoki et al. |
| 2002/0147160 A1 | 10/2002 | Bhat et al. |
| 2003/0143561 A1 | 7/2003 | Pedersen et al. |
| 2010/0092957 A1 | 4/2010 | Zhao et al. |

FOREIGN PATENT DOCUMENTS

| | | |
|---|---|---|
| JP | 2001-288197 A | 10/2001 |
| JP | 2001-519354 A | 10/2001 |
| JP | 2001-525797 A | 12/2001 |
| JP | 2002-507203 A | 3/2002 |
| JP | 2003-507072 A | 2/2003 |
| JP | 2004-135673 A | 5/2004 |
| JP | 2004-529650 A | 9/2004 |
| JP | 2004-532184 A | 10/2004 |
| JP | 2004-329218 A | 11/2004 |
| JP | 2004-535193 A | 11/2004 |
| JP | 2008-054658 A | 3/2008 |
| WO | 01/14568 A1 | 3/2001 |
| WO | 01/19841 A1 | 3/2001 |
| WO | 02/057425 A2 | 7/2002 |
| WO | 2008/042067 A2 | 4/2008 |

OTHER PUBLICATIONS

Kuwahara, Masayasu et al. "Direct PCR amplification of various modified DNAs having amino acids: Convenient preparation of DNA libraries with high-potential activities for in vitro selection," Bioorganic and Medicinal Chemistry, Received Oct. 9, 2006, vol. 14(8), pp. 2518-2526, cited in ISR.

Kuwahara, Masayasu et al. "Enzymatic incorporation of chemically-modified nucleotides into DNAs," Nucleic Acids Research Supplement, 2002, No. 2, pp. 83-84, cited in ISR.

Stuhmiller, Louise M. et al. "Methotrexate 5-Aminoallyl-2'-Deoxyuridine 5'-Mono-Phosphate: A Potential Bifunctional Inhibitor of Thymidylate Synthase," Advances in Enzyme Regulation, 1989, vol. 29, pp. 141-157, cited in ISR.

International Search Report of PCT/JP2009/063454, mailing date Oct. 13, 2009.

Japanese Office Action dated Oct. 6, 2009, issued in corresponding Japanese Patent Application No. 2009-032763.

(1 : Marker, 2 : 0% 3 : 20%, 4 : 40 %, 5 : 60%, 6 : 80%, 7 :100%)

(1 : Marker, 2 : 0% 3 : 20%, 4 : 40 %, 5 : 60%, 6 : 80%, 7 :100%)

(1 : Marker, 2 : MTG (-) , MTG (+))

Lane
M: Size Marker
1: Z-QG-dUTP 0%
2: Z-QG-dUTP 50%
3: Z-QG-dUTP 100%

Lane
M: Size Marker
1: Z-QG-dUTP 50%, HEAT TREATMENT PRIOR TO MTG REACTION
2: Z-QG-dUTP 100%, HEAT TREATMENT PRIOR TO MTG REACTION
3: Z-QG-dUTP 50%, HEAT TREATMENT FOLLOWING MTG REACTION
4: Z-QG-dUTP 100%, HEAT TREATMENT FOLLOWING MTG REACTION

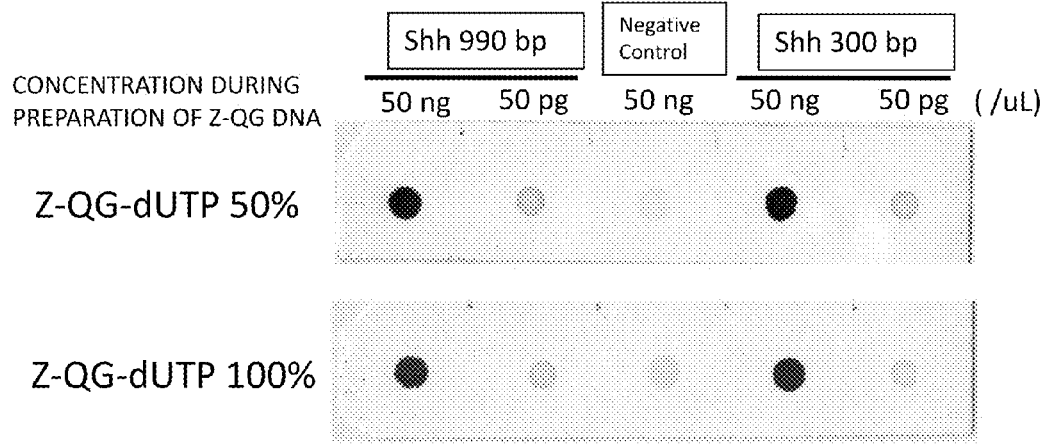
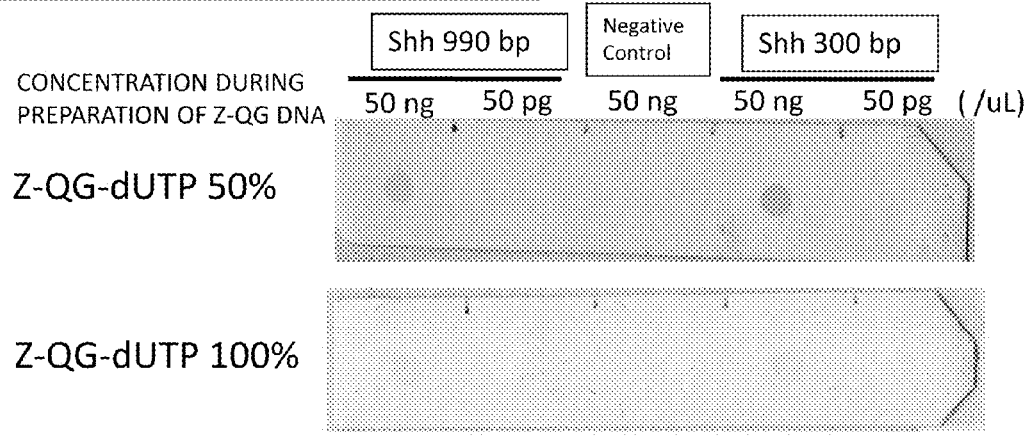
FIG. 23

EVALUATION OF PROBE PERFORMANCE OF BAP
MULTILABELED RNA (ALL USING S CHAIN ANCHORING)

1 2 3 4 5

NUCLEOSIDE TRIPHOSPHATE DERIVATIVE, NUCLEIC ACID PROBE, MULTILABELED NUCLEIC ACID PROBE, METHOD FOR PRODUCTION OF MULTILABELED NUCLEIC ACID PROBE, AND METHOD FOR DETECTION OF TARGET NUCLEIC ACID

TECHNICAL FIELD

The present invention relates to a nucleoside triphosphate derivative, a nucleic acid probe, a multilabeled nucleic acid probe, a method for producing a multilabeled nucleic acid probe, and a method for detecting a target nucleic acid.

BACKGROUND ART

By using a nucleic acid probe such as an RNA probe that has been subjected to some form of labeling to detect and visualize the pattern of expression of DNA or RNA at a cellular level, a multitude of problems related to vital phenomena can be explained. This type of technique that enables the visualization of gene expression patterns at a cellular level is termed in situ hybridization (ISH), and the labeling methods employed for the probes used in this technique can be broadly classified into "radioactive isotope labeling methods", "fluorescent antibody labeling methods" and "enzyme antibody labeling methods." Historically, nucleic acid probes having an introduced radioactive isotope were developed first, but in recent years, restrictions have been introduced relating to the handling of such probes, and therefore fluorescent antibody labeling methods and enzyme antibody labeling methods, which do not require the use of a radioactive isotope element, are attracting much attention.

In these techniques, labeling is performed with an antigen or biotin during preparation of the nucleic acid probe, and following hybridization of the nucleic acid probe with the target nucleic acid, detection is performed by an immunostaining method using an antibody or avidin labeled with an enzyme or a fluorescent material. Enzyme antibody labeling methods, in which a signal amplification effect is achieved as a result of an enzyme reaction, offer superior sensitivity and are therefore currently the most widely used.

Examples of known nucleic acid probes that utilize enzyme antibody labeling methods include antigen-multilabeled nucleic acid probes in which a plurality of nucleotide derivatives that have been modified at the antibody recognition site such as digoxigenin (DIG) are introduced in a random arrangement. Following in situ hybridization of this antigen-multilabeled nucleic acid probe and the target nucleic acid, an antigen-antibody reaction is conducted with an enzyme-labeled antibody that recognizes the antibody recognition site, and detection is performed using a color development reaction that utilizes a hybrid with enzyme alkaline phosphatase. However, there are several problems associated with this method, including the fact that the enzyme-labeled antibody is extremely expensive, the complexity of the operations required for the antigen-antibody reaction, and an increased background reading caused by nonspecific adsorption and the like.

On the other hand, a method is known in which a transglutaminase (TGase) is used to achieve site-specific binding of an exogenous molecule, which is anionic and has a glutamine (Gln) residue that is recognizable by TGase, to a peptide or protein having a lysine (Lys) residue or a primary amine which are recognizable by TGase (for example, see Patent Document 1).

PRIOR ART

Patent Documents

PATENT DOCUMENT 1: JP 2008-54658 A

DISCLOSURE OF INVENTION

Problems to be Solved by the Invention

The present invention provides a novel nucleoside triphosphate derivative, a nucleic acid probe, and a multilabeled nucleic acid probe that can detect a target nucleic acid conveniently and with high sensitivity, and also provides a method for producing the multilabeled nucleic acid probe, and a method for detecting a target nucleic acid using the multilabeled nucleic acid probe or the nucleic acid probe.

Means for Solving the Problems

The present invention provides a nucleoside triphosphate derivative having a glutamine (Gln) residue.

Further, the nucleoside triphosphate derivative is preferably represented by formula (1) shown below.

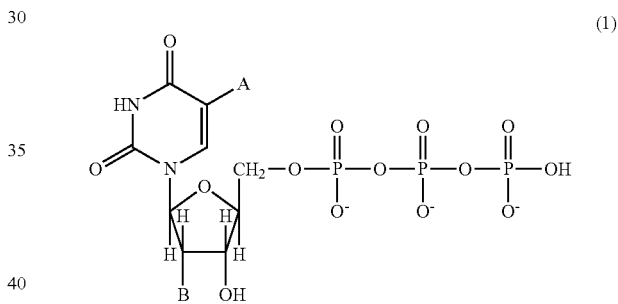

In formula (1), A represents a substituent having a glutamine (Gln) residue, and B represents a hydrogen atom or a hydroxyl group.

Furthermore, the nucleoside triphosphate derivative is preferably represented by formula (2) shown below.

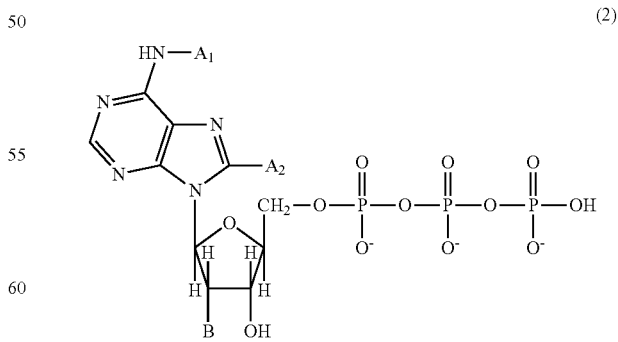

In formula (2), at least one of $A_1$ and $A_2$ represents a substituent having a glutamine (Gln) residue, with any remainder representing a hydrogen atom, and B represents a hydrogen atom or a hydroxyl group.

Furthermore, the nucleoside triphosphate derivative is preferably represented by formula (3) shown below.

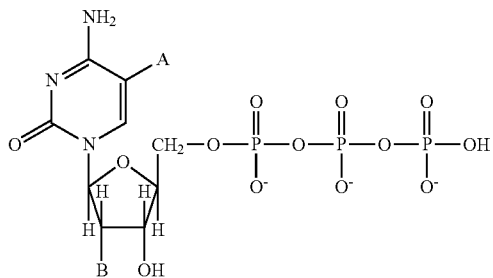

(3)

In formula (3), A represents a substituent having a glutamine (Gln) residue, and B represents a hydrogen atom or a hydroxyl group.

Furthermore, the nucleoside triphosphate derivative is preferably represented by formula (4) shown below.

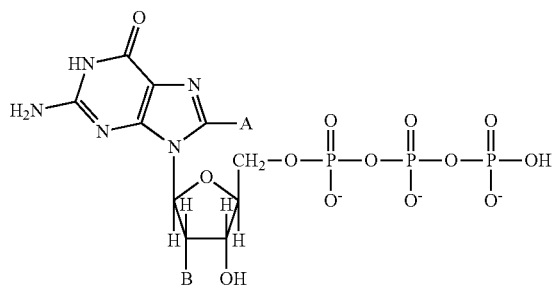

(4)

In formula (4), A represents a substituent having a glutamine (Gln) residue, and B represents a hydrogen atom or a hydroxyl group.

Furthermore, the nucleoside triphosphate derivative is preferably represented by formula (5) shown below.

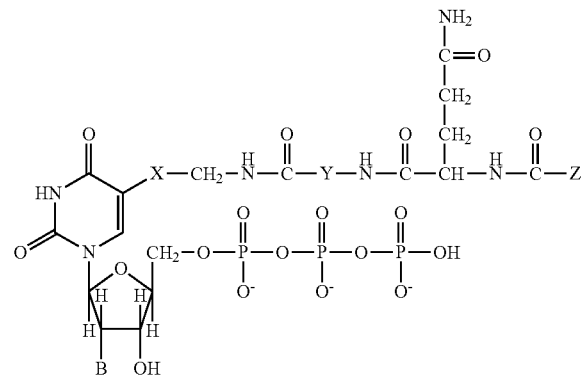

(5)

In formula (5), each of X and Y independently represents a bivalent linking group, and Z represents a substituent.

Further, in the nucleoside triphosphate derivative, each of the above-mentioned X and Y preferably independently represents an alkylene group having a carbon number of 1 to 48 or an alkenylene group having a carbon number of 2 to 48, and Z preferably represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48. Furthermore, Y may be an oxyalkylene group having a carbon number of 2 to 48 (such as an oxyethylene group or oxypropylene group), and at least one of Y and Z may be independently a substituent with an amino acid other than Lys.

Furthermore, in the nucleoside triphosphate derivative, X is preferably an ethenylene group, Y is preferably a methylene group, and Z is preferably a benzyloxy group.

Further, the present invention also provides a nucleic acid probe that is a nucleic acid in which a plurality of the above nucleoside triphosphate derivatives have been introduced as structural units.

Furthermore, the present invention also provides a multilabeled nucleic acid probe comprising a labeling compound having a lysine (Lys) residue or a primary amine and containing a labeling portion bound to each of at least two glutamine (Gln) residues within the above-mentioned nucleic acid probe.

Further, in the multilabeled nucleic acid probe, the labeling portion is preferably at least one of an enzyme and a fluorescent dye.

Further, in the multilabeled nucleic acid probe, the enzyme is preferably an enzyme derived from a hyperthermophile.

Further, in the multilabeled nucleic acid probe, the enzyme is preferably an enzyme that is stable with respect to organic solvents and heat.

Furthermore, the present invention also provides a method for producing a multilabeled nucleic acid probe, the method comprising using a transglutaminase (TGase) to bind a labeling compound having a lysine (Lys) residue or a primary amine and containing a labeling portion to each of at least two glutamine (Gln) residues within the above-mentioned nucleic acid probe.

Further, in the method for producing a multilabeled nucleic acid probe, the labeling portion is preferably at least one of an enzyme and a fluorescent dye.

Further, in the method for producing a multilabeled nucleic acid probe, the enzyme is preferably an enzyme derived from a hyperthermophile.

Furthermore, the present invention also provides a method for detecting a target nucleic acid, the method comprising performing specific binding, via the nucleic acid portions, of the multilabeled nucleic acid probe and a target nucleic acid that exists within a target material, and detecting the bound multilabeled nucleic acid probe via the labeling portion.

Furthermore, the present invention also provides a method for detecting a target nucleic acid, the method comprising performing specific binding, via the nucleic acid portions, of the above-mentioned nucleic acid probe and a target nucleic acid that exists within a target material, subsequently introducing a plurality of labeling portions by using a transglutaminase (TGase) to react glutamine (Gln) residues within the nucleic acid probe with a lysine (Lys) residue or a primary amine of a labeling compound having a lysine (Lys) residue or a primary amine and containing a labeling portion, and detecting the bound nucleic acid probe via the labeling portions.

Advantages of the Invention

The present invention is able to provide a novel nucleoside triphosphate derivative and a nucleic acid probe used for preparing a multilabeled nucleic acid probe having a plurality of labeling portions introduced therein by covalent binding.

Further, the present invention is able to provide a multilabeled nucleic acid probe that can detect a target nucleic acid conveniently and with high selectivity, by introducing a plurality of labeling portions into a nucleic acid probe in advance by covalent binding, prior to hybridization of the probe with the target nucleic acid.

Furthermore, the present invention is able to provide a method for producing a multilabeled nucleic acid probe that can detect a target nucleic acid conveniently and with high selectivity, by using a transglutaminase (TGase) to introduce a plurality of labeling portions into a nucleic acid probe by covalent binding.

Further, the present invention is able to provide a method for detecting a target nucleic acid conveniently and with high selectivity, by using a multilabeled nucleic acid probe having a plurality of enzymes introduced therein in advance by covalent binding.

Furthermore, the present invention is able to provide a method for detecting a target nucleic acid conveniently and with high selectivity, by hybridizing a nucleic acid probe with a target nucleic acid, and subsequently introducing a plurality of labeling portions by covalent binding via a simple reaction between glutamine (Gln) residues within the nucleic acid probe and a lysine (Lys) residue or a primary amine of a labeling compound.

BRIEF DESCRIPTION OF THE DRAWINGS

FIG. 23 is a diagram illustrating the results of dot blots for each PfuAP-labeled DNA probe in example 3 of the present invention.

MODE FOR CARRYING OUT THE INVENTION

Embodiments of the present invention are described below. These embodiments are merely examples of implementing the present invention, and the present invention is in no way limited by these embodiments.

The inventors of the present invention focused their attention on the site-specific protein-modifying ability possessed by transglutaminases (TGase) such as microbial transglutaminase (MTG), as a technique for introducing a plurality of enzymes into a nucleic acid probe via covalent binding. TGase is an enzyme that catalyzes transacylation reactions, and for example, catalyzes covalent binding between the γ-carboxamide group of specific Gln residues (Q) within a protein, and the ε-amino group of a lysine residue (K) or any of various primary amines. Using this TGase, multilabeled nucleic acid probes containing a plurality of introduced labeling portions such as labeling enzymes can be created.

Figure 1:
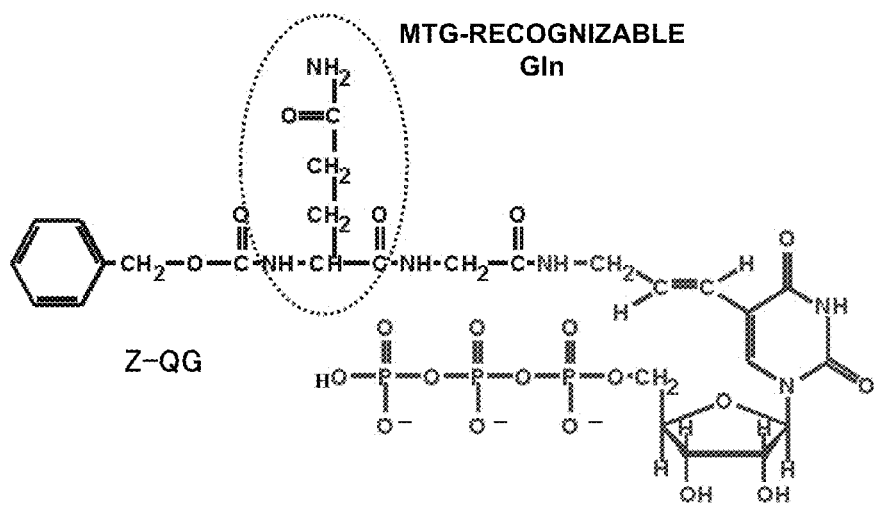
FIG. 1 is a diagram illustrating one example of the structure of a nucleotide derivative (Z-QG-UTP) according to an embodiment of the present invention.
Figure 2:
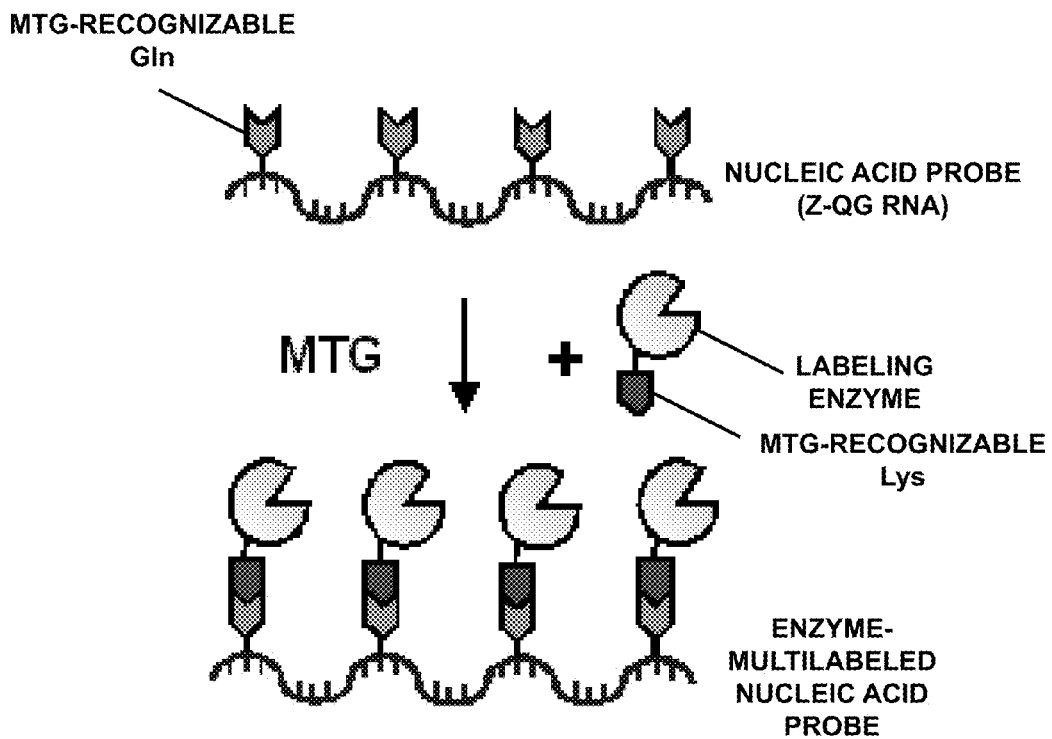
FIG. 2 is a schematic view illustrating a method for preparing an enzyme-multilabeled nucleic acid probe according to an embodiment of the present invention.

In a specific example, Z-QG-UTP is synthesized, which is a nucleotide derivative illustrated in FIG. 1 in which Z-QG having a Gln residue that is recognized by TGase (MTG-recognizable Gln) is bound to uridine triphosphate (UTP), and then as illustrated in FIG. 2, by incorporating this Z-QG-UTP during preparation of an RNA that functions as a nucleic acid probe, a Z-QG RNA having introduced TGase-recognizable Gln residues at a plurality of locations is prepared. Subsequently, by using a TGase such as MTG to achieve binding of a labeling compound such as a labeling enzyme having an introduced TGase-recognizable Lys such as MTG-recognizable Lys, a multilabeled nucleic acid probe in which the labeling ratio between the RNA and the labeling portion such as a labeling enzyme is 1:n (wherein n is an integer of 2 or greater) can be produced.

Because this multilabeled nucleic acid probe can be subjected to a detection reaction immediately following hybridization with the target nucleic acid, the operation can be simplified considerably and the background reduced, and because the bulk enzyme microbial transglutaminase (MTG) is used, significant cost reductions can be expected compared with conventional techniques.

In FIG. 2, the Gln residue in the nucleic acid probe and the Lys residue in the labeling compound may be reversed. In other words, by synthesizing a nucleoside triphosphate derivative having a Lys residue that is recognized by TGase (MTG-recognizable Lys), and then incorporating this derivative during preparation of an RNA that functions as a nucleic acid probe, a nucleic acid probe having introduced TGase-recognizable Lys residues at a plurality of locations is prepared. Subsequently, by using a TGase such as MTG to achieve binding of a labeling compound having an introduced TGase-recognizable Gln residue such as MTG-recognizable Gln, a multilabeled nucleic acid probe in which the labeling ratio between the RNA and the labeling portion is 1:n (wherein n is an integer of 2 or greater) may be produced.

Figure 16:
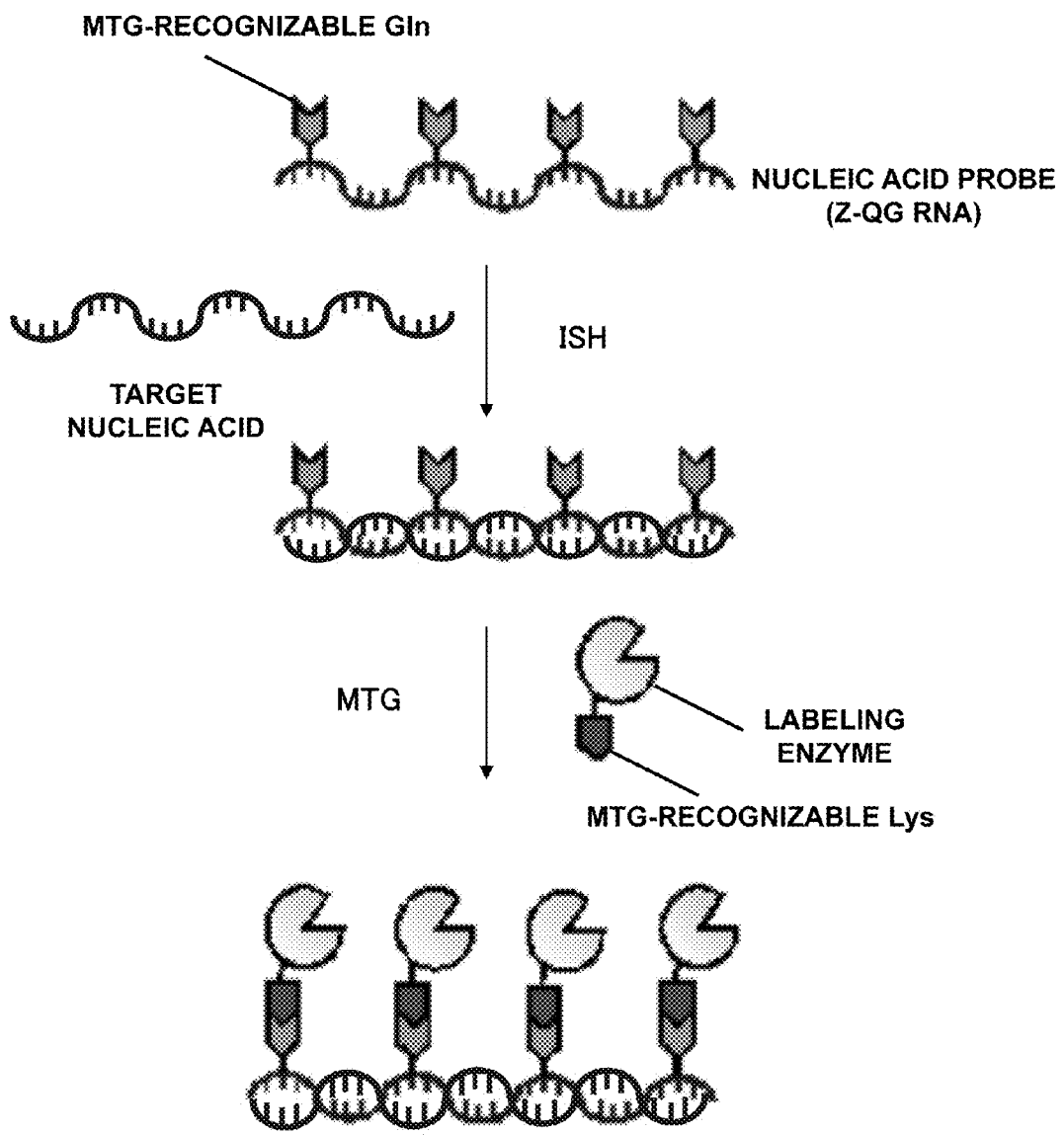
FIG. 16 is a schematic illustration illustrating one example of a method for detecting a target nucleic acid according to an embodiment of the present invention.

Furthermore, as illustrated in FIG. 16, a nucleic acid probe such as Z-QG RNA may be first hybridized with the target nucleic acid, and a TGase such as MTG then used to bind a labeling compound such as a labeling enzyme having an introduced TGase-recognizable Lys such as MTG-recognizable Lys. The labeling ratio between the RNA and the labeling portion such as a labeling enzyme is 1:n (wherein n is an integer of 2 or greater), and by subsequently performing a detection reaction for these introduced labeling portions, the operation can be simplified considerably and the background reduced, and because the bulk enzyme microbial transglutaminase (MTG) is used, significant cost reductions and the like can be expected compared with conventional techniques.

In FIG. 16, the Gln residue in the nucleic acid probe and the Lys residue in the labeling compound may be reversed. In other words, by synthesizing a nucleoside triphosphate derivative having a Lys residue that is recognized by TGase (MTG-recognizable Lys), and then incorporating this derivative during preparation of an RNA that functions as a nucleic acid probe, a nucleic acid probe having introduced TGase-recognizable Lys residues at a plurality of locations is prepared. Subsequently, this nucleic acid probe may be hybridized with the target nucleic acid, and a TGase such as MTG then used to bind a labeling compound having an introduced TGase-recognizable Gln such as MTG-recognizable Gln.

<Nucleoside Triphosphate Derivative>

The nucleoside triphosphate derivative according to an embodiment of the present invention has a glutamine (Gln) residue. Examples of this nucleoside triphosphate derivative having a glutamine (Gln) residue include uridine triphosphate (UTP) derivatives having a glutamine (Gln) residue, adenosine triphosphate (ATP) derivatives having a glutamine (Gln) residue, guanosine triphosphate (GTP) derivatives having a glutamine (Gln) residue, cytidine triphosphate (CTP) derivatives having a glutamine (Gln) residue, deoxyuridine triphosphate (dUTP) derivatives having a glutamine (Gln) residue, deoxyadenosine triphosphate (dATP) derivatives having a glutamine (Gln) residue, deoxyguanosine triphosphate (dGTP) derivatives having a glutamine (Gln) residue, and deoxycytidine triphosphate (dCTP) derivatives having a glutamine (Gln) residue. In the nucleoside triphosphate derivative according to this embodiment, for example the glutamine (Gln) residue is bonded to the uracil, adenine, guanine or cytosine portion, either directly or with a substituent disposed therebetween.

These nucleoside triphosphate derivatives can be obtained from UTP, ATP, GTP, CTP, dUTP, dATP, dGTP, dCTP or derivatives thereof.

Further, these nucleoside triphosphate derivatives may also be obtained from uridine, uridine monophosphate (UMP) and diphosphate (UDP), adenosine, adenosine monophosphate (AMP) and diphosphate (ADP), guanosine, guanosine monophosphate (GMP) and diphosphate (GDP), cytidine, cytidine monophosphate (CMP) and diphosphate (CDP), deoxyuridine, deoxyuridine monophosphate (dUMP) and diphosphate (dUDP), deoxyadenosine, deoxyadenosine monophosphate (dAMP) and diphosphate (dADP), deoxyguanosine, deoxyguanosine monophosphate (dGMP) and diphosphate (dGDP), deoxycytidine, deoxycytidine monophosphate (dCMP) and diphosphate (dCDP), as well as various derivatives of these compounds.

For example, the triphosphate derivatives of the above compounds can be obtained from uridine, adenosine, guanosine, cytidine, deoxyuridine, deoxyadenosine, deoxyguanosine or deoxycytidine by phosphorylation using a phosphorylation enzyme or the like (for example, see Seibutsu-kogaku kaishi (Journal of The Society for Biotechnology, Japan), 85(9), pp. 397 to 399 (2007), and Journal of Bioscience and Bioengineering, 87(6), pp. 732 to 738 (1999)), or by phosphorylation by phosphorus oxychloride or the like in the presence of a proton sponge (for example, see Tetrahedron Letters, 29(36), pp. 4525 to 4528 (1988)).

The nucleoside triphosphate derivative according to the present embodiment is, for example, a uridine triphosphate derivative represented by formula (1) below, having a glutamine (Gln) residue that is recognizable by TGase.

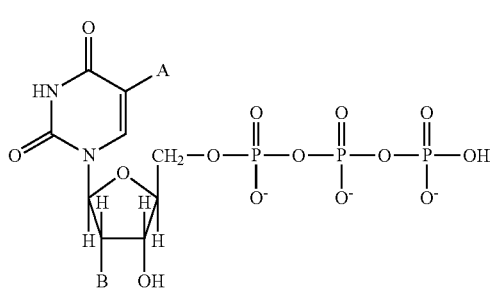

In formula (1), A represents a substituent having a glutamine (Gln) residue, and B represents a hydrogen atom or a hydroxyl group.

The nucleoside triphosphate derivative according to the present embodiment is, for example, an adenosine triphosphate derivative represented by formula (2) below, having a glutamine (Gln) residue that is recognizable by TGase.

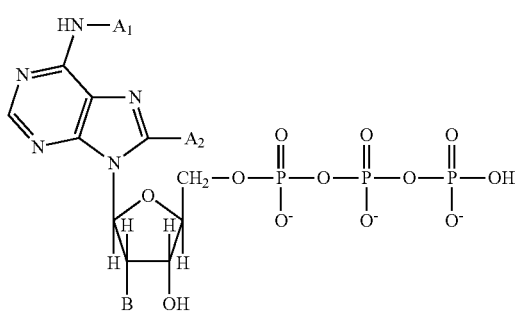

In formula (2), at least one of $A_1$ and $A_2$ represents a substituent having a glutamine (Gln) residue, with any remainder representing a hydrogen atom, and B represents a hydrogen atom or a hydroxyl group.

The nucleoside triphosphate derivative according to the present embodiment is, for example, a cytidine triphosphate derivative represented by formula (3) below, having a glutamine (Gln) residue that is recognizable by TGase.

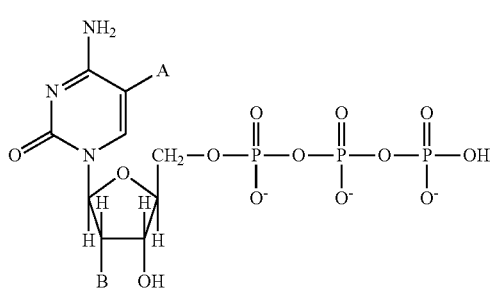

In formula (3), A represents a substituent having a glutamine (Gln) residue, and B represents a hydrogen atom or a hydroxyl group.

The nucleoside triphosphate derivative according to the present embodiment is, for example, a guanosine triphosphate derivative represented by formula (4) below, having a glutamine (Gln) residue that is recognizable by TGase.

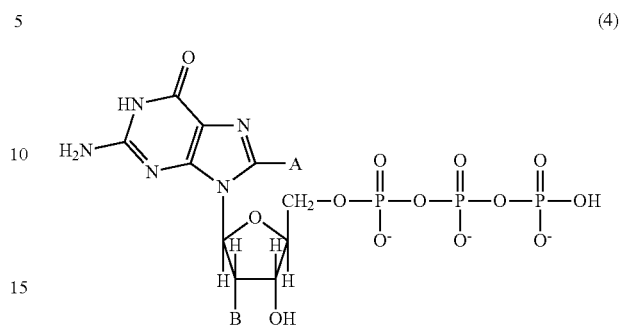

In formula (4), A represents a substituent having a glutamine (Gln) residue, and B represents a hydrogen atom or a hydroxyl group.

There are no particular limitations on the substituent having a glutamine (Gln) residue represented by A, and examples include substituents comprising a linear, branched or cyclic saturated or unsaturated alkyl group, aminoalkyl group, aryl group or heteroaryl group that has a glutamine (Gln) residue. The substituent may be selected with due consideration of factors such as the ease of synthesis.

The nucleoside triphosphate derivative according to the present embodiment is, for example, a TGase substrate modified nucleotide derivative represented by formula (5) below, having a glutamine (Gln) residue that is recognizable by TGase.

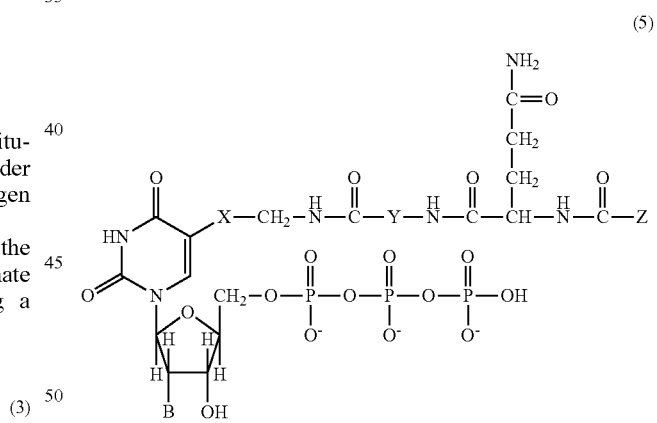

In formula (5), each of X and Y independently represents a bivalent linking group, and Z represents a substituent.

Examples of the bivalent linking groups represented by X and Y, which are mutually independent, include alkylene groups having a carbon number of 1 to 48 such as a methylene group, ethylene group, propylene group or butylene group, and alkenylene groups having a carbon number of 2 to 48 such as an ethenylene group, propenylene group or butenylene group. Of these, each of X and Y preferably independently represents an alkylene group having a carbon number of 1 to 48, an alkenylene group having a carbon number of 2 to 48, or an alkoxy group having a carbon number of 1 to 48, and those cases in which X represents an ethenylene group and Y represents a methylene group are particularly desirable. X and Y may also be substituted with an ethenylene group or oxyalkylene group, such as —(C$_2$H$_4$O)$_n$— or —(C$_3$H$_6$O)$_n$— (wherein n represents a repetition number, such that n=2, 4, 8, 12 or 24).

Examples of the substituent represented by Z include alkyl groups having a carbon number of 1 to 48 such as a methyl group, ethyl group or propyl group, alkoxy groups having a carbon number of 1 to 48 such as a methoxy group, ethoxy group or propoxy group, aryl groups having a carbon number of 6 to 48 such as a phenyl group or naphthyl group, aryloxy groups having a carbon number of 6 to 48 such as a phenyloxy group, arylalkyl groups having a carbon number of 7 to 48 such as a benzyl group, and arylalkyloxy groups having a carbon number of 7 to 48 such as a benzyloxy group. Of these, Z is preferably an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48, and is more preferably a benzyloxy group. Z may also be substituted with a dinitrophenyl group or L-3,4-dihydroxyphenyl group or the like. Further, in combination with the above substituent represented by Y, at least one of Y and Z may be independently a substituent with an amino acid other than Lys.

By appropriate selection of X, the structure of the linker region that links the Z-QG and UTP can be optimized, so that for example, by introducing a flexible linker region, access by enzymes or the like can be improved. Further, appropriate selection of Y and Z enables the substrate peptide sequence to be optimized, so that for example, the affinity for enzymes or the like can be improved.

In those cases where microbial TGase (MTG) is used, the MTG-recognizable Gln residue preferably exists as benzyloxycarbonyl-L-glutamylglycine (Z-QG). Z-QG is preferable as it has a smaller molecular size than digoxigenin (DIG) or the like. In the nucleoside triphosphate derivative represented by formula (5), the nucleotide derivative in which X represents an ethenylene group, Y represents a methylene group and Z represents a benzyloxy group is the nucleotide derivative Z-QG-UTP in which Z-QG is bonded to UTP. Further, selection of a nucleoside triphosphate derivative that does not also contain a TGase-recognizable Lys residue or primary amine is preferred. This is because if the nucleoside triphosphate derivative also contains such a Lys residue or primary amine, then TGase may cause self cross-linking, which has an adverse effect on the yield of the targeted multilabeled nucleic acid probe.

Further, examples of good substrates for microbial TGase include peptides composed of amino acid sequences represented by LLQG (sequence number: 1), LAQG (sequence number: 2), LGQG (sequence number: 3), PLAQSH (sequence number: 4), FERQHMDS (sequence number: 5) or TEQKLISEEDL (sequence number: 6), or peptides composed of amino acid sequences represented by GLGQGGG (sequence number: 7), GFGQGGG (sequence number: 8), GVGQGGG (sequence number: 9), or GGLQGGG (sequence number: 10). Further examples of good substrates for guinea pig liver-derived TGase include benzyloxycarbonyl-L-glutamylphenylalanine (Z-QF), peptides composed of an amino acid sequence EAQQIVM (sequence number: 11), or peptides composed of amino acid sequences represented by GGGQLGG (sequence number: 12), GGGQVGG (sequence number: 13), GGGQRGG (sequence number: 14), GQQQLG (sequence number: 15), PNPQLPF (sequence number: 16), or PKPQQFM (sequence number: 17). Depending on the type of TGase used, the Gln residue that is recognizable by TGase may exist as one of these types of peptides.

In substrate peptides in which the N-terminal is a glycine (G), the N-terminal amino group can functions as the TGase substrate, and therefore by-products caused by self cross-linking may occur. Accordingly, in the case of substrate peptides in which the N-terminal is a glycine (G), the peptide can be protected from becoming the TGase substrate by substituting the hydrogen atoms of the N-terminal amino group with an appropriate group, thereby ensuring that the desired linkage occurs. In this description, unless specifically stated otherwise, the expression "N-terminal protection" is used to describe this type of protection. It is known that the reactivity varies depending on the method employed for the N-terminal protection. Specifically, it is known that for mammals-derived TGase, protection by N-terminal acetylation of GQQQLG (namely, Ac-GQQQLG) or conversion of the N-terminal amino acid to DOPA (L-3,4-dihydroxyphenylalanine) (namely, DOPA-GQQQLG) result in increased reactivity. These types of protection examples may also be utilized in the present embodiment.

Figure 3:
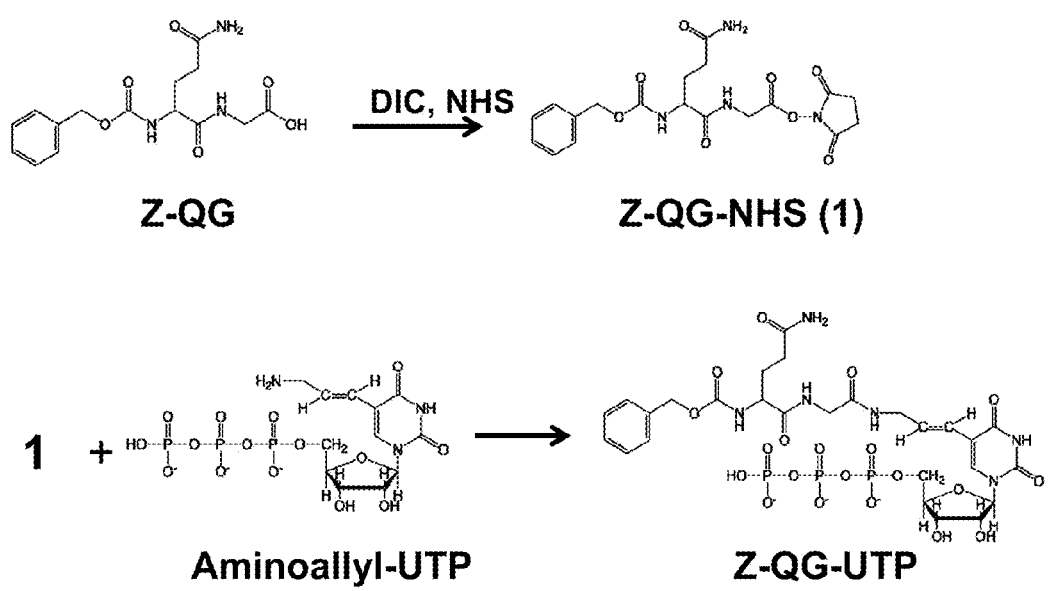
FIG. 3 is a diagram illustrating one example of a method for synthesizing Z-QG-UTP, which represents one example of a nucleotide derivative according to an embodiment of the present invention.

A method for preparing Z-QG-UTP is illustrated in FIG. 3. This merely represents one example of a method for preparing a nucleoside triphosphate derivative according to the present embodiment, and the present invention is not limited to this example.

First, an N-hydroxysuccinimide (NHS) group or the like is introduced into benzyloxycarbonyl-L-glutamylglycine (Z-QG) to activate the molecule (Z-QG-NHS). Subsequently, a UTP having an aminated substituent at the terminal such as aminoallyl-UTP is condensed with the Z-QG-NHS, yielding Z-QG-UTP.

Further, in addition to the above method in which the C-terminal carboxyl group is converted to an active ester, a method in which a functional group that exhibits high reactivity with amino groups is introduced into the peptide may also be used as a method of introducing a peptide having a TGase-recognizable Gln residue into UTP. For example, if a substrate peptide that has undergone conversion to an aldehyde, acyl azide, sulfonyl chloride, epoxide, isocyanate or isothiocyanate can be prepared, then subsequent reaction of this substrate peptide with an aminated UTP can be used to prepare a UTP having a Gln residue that is recognizable by TGase. However, these reactive functional groups can be introduced into the substrate peptide at a portion that does not effect TGase recognition. In order to satisfy this requirement, the method described above in which the carboxyl group of the C-terminal distant from the Gln residue is activated is the most desirable.

Purification of the Z-QG-UTP can be performed by high performance liquid chromatography (HPLC) or gel permeation chromatography (GPC) or the like. Further, identification of the Z-QG-UTP can be performed by MALDI TOF-MS, NMR and IR and the like. Further, HPLC can be used to confirm the product and determine the yield.

<TGase Substrate-Multilabeled Nucleic Acid>

The TGase substrate-multilabeled nucleic acid according to an embodiment of the present invention is a TGase substrate-multilabeled nucleic acid in which a TGase substrate-labeled nucleoside triphosphate derivative such as those represented by formulas (1) to (5) is prepared, and a plurality of these TGase substrate-labeled nucleoside triphosphate derivatives are then introduced into the nucleic acid as a structural unit, wherein the nucleic acid portion has a sequence that is complementary to all or part of the target molecule specific sequence of the target nucleic acid that represents the detection target.

The nucleic acid includes DNA, PNA and RNA. There are no particular limitations on the sequence or length of the nucleic acid. In terms of length, a length of at least approximately 20 mer is preferred.

For example, by using Z-QG-UTP as a substrate, and using an enzyme having RNA polymerase activity to incorporate a plurality of Z-QG-UTP and introduce TGase-recognizable Gln residues at a plurality of locations, a TGase substrate-multilabeled nucleic acid probe Z-QG RNA having the desired sequence can be prepared (see FIG. 2).

<Multilabeled Nucleic Acid Probe>

The multilabeled nucleic acid probe according to an embodiment of the present invention comprises a labeling compound having a lysine (Lys) residue or a primary amine and containing a labeling portion bound to each of at least two glutamine (Gln) residues of the nucleoside triphosphate derivative that functions as a structural unit within the above nucleic acid probe. The multilabeled nucleic acid probe can be generated, for example, by using a TGase such as MTG to bind a labeling enzyme or the like having a TGase-recognizable Lys introduced therein to the nucleic acid probe Z-QG RNA having a TGase-recognizable Gln residue such as MTG-recognizable Gln introduced at a plurality of locations, and has a labeling ratio between the RNA and the labeling portion of the labeling enzyme or the like of 1:n. (see FIG. 2).

There are no particular limitations on the value of n in the ratio between the RNA and the labeling portion of the labeling enzyme or the like, provided that n is 2 or greater. The value of n may be altered as required, but a larger value of n yields a higher detection sensitivity and is therefore preferred. However, if n is too large, then the efficiency of the hybridization with the target nucleic acid may deteriorate.

Further, by using the methods described below, a plurality of multilabeled nucleic acid probes having different labeling portions such as different labeling enzymes or different fluorescent dyes can be prepared.

(1) Changing the origin of the TGase
(2) Changing the substrate specificity of the TGase In method (1), for example, UTP molecules that have been modified with different substrate peptides may be prepared by changing the variety of TGase that is used.

In method (2), for example, an amino acid variation may be introduced by protein engineering to change the substrate specificity. For example, MTG may be prepared in coli bacteria (for example, see Christian K. Marx, Thomas C. Hertel and Markus Pietzch, Enzyme and Microbial Technology, volume 40, issue 6, 2 May 2007, pp. 1543 to 1550, "Soluble expression of a pro-transglutaminase from *Streptomyces mobaraensis* in *Escherichia coli*"), a variant library then generated, and the MTG variants exhibiting improved heat resistance then acquired (for example, see Christian K. Marx, Thomas C. Hertel and Markus Pietzch, Journal of Biotechnology, volume 136, issues 3-4, 10 Sep. 2008, pp. 156 to 162, "Randommutagenesis of a recombinant microbial transglutaminase for the generation of thermostable and heat-sensitive variants").

When the present description states that "binding is performed using TGase", with the exception of special circumstances, this description means that the obtained linking portion is generated as a result of the Lys residue and the Gln residue forming an $\epsilon$-($\gamma$-glutamyl) lysine bond.

In the present embodiment, the Lys residue that is recognizable by TGase may be a primary amine. In this description, a Lys residue is used as an example, but unless specifically stated otherwise, the description also applies to primary amines.

There are no particular limitations on the labeling compound having a lysine (Lys) residue or a primary amine and containing a labeling portion.

Examples of the labeling portion include enzymes, fluorescent dyes, compounds containing a radioactive isotope, markers that can be detected magnetically (such as magnetic nanoparticles), markers that can be detected thermally (such as temperature-responsive polymers) and markers that can be detected electrically (such as polymers containing ferrocene sites), although from the viewpoints of detection sensitivity and handling, at least one of an enzyme and a fluorescent dye is preferable.

There are no particular limitations on the fluorescent dye, provided it is a material that emits fluorescence or phosphorescence in response to irradiation with ultraviolet light or visible light or the like of a selected wavelength. Examples of fluorescent dyes include fluorescein, rhodamine, dansyl and carbocyanine derivatives, whereas examples of fluorescent proteins include green fluorescent protein and variants thereof.

Examples of radioactive isotopes include deuterium ($^2$H), tritium ($^3$H), $^{10}$B, $^{11}$B, $^{13}$C, $^{15}$N and $^{18}$O.

It is thought that for TGase, the substrate that functions as a Lys residue (or primary amine) donor has fewer structural restrictions than the substrate that functions as a Gln residue donor. Accordingly, there are cases where the labeling enzyme that is to be modified has a TGase-recognizable Lys residue from the beginning, and cases where a tag comprising a TGase-recognizable Lys residue is added to the enzyme.

The Lys residue (K) that is recognizable by TGase may exist as a peptide having an amino acid sequence represented by MKHKGS (sequence number: 18), MRHKGS (sequence number: 35), MRRKGS (sequence number: 36) or MHRKGS (sequence number: 37). Tagging with this type of peptide comprising a TGase-recognizable Lys residue can be used for the purpose of binding the labeling enzyme to a desired site on a protein, such as the C-terminal or N-terminal. Examples of other peptides comprising a TGase-recognizable Lys residue and their amino acid sequences include altered S-peptides (GSGMKETAAARFERAHMDSGS (sequence number: 19)), MGGSTKHKIPGGS (sequence number: 20), N-terminal glycines (N-terminal GGG, N-terminal GGGGG (sequence number: 21)), and MKHKGGGSGGGSGS (sequence number: 22) in which the linker region between N-terminal MKHKGS and the target protein has been extended.

Labeling enzymes having an added peptide comprising a TGase-recognizable Lys residue at the C-terminal or N-terminal can be prepared as recombinant proteins using genetic engineering techniques. Purification of such recombinant proteins in which a TGase substrate peptide tag has been introduced at the C-terminal or N-terminal can be conducted by gel permeation chromatography or the like, using a purification peptide tag added at the N-terminal or C-terminal (for example, a (His)$_6$-tag (hexahistidine tag)) (in order to avoid any deterioration in the reactivity of the TGase, the design should be made so that the purification peptide tag is introduced at a different terminal from the terminal containing the introduced substrate peptide tag). Confirmation of the amino acid sequence may be performed by using a DNA sequencer to confirm the gene sequence of the plasmid vector that codes the protein, or in the case of a substrate peptide introduced at the N-terminal, by direct identification by N-terminal analysis. Confirmation of the protein purification can be performed by SDS-PAGE or the like.

There are no particular limitations on the labeling enzyme, provided it possesses a property that enables detection to be performed using a coloration reaction or the like. Examples include alkaline phosphatase (AP), glutathione S-transferase (GST), luciferase and peroxidase. Of these, from the viewpoints of achieving high catalytic activity and good stability, alkaline phosphatase or peroxidase is preferred. From the viewpoint of facilitating introduction of a peptide tag, proteins that can be produced by genetic engineering are preferred.

In order to achieve a more precise base sequence-specific double strand formation between the enzyme-multilabeled nucleic acid probe and the target nucleic acid, reaction may sometimes be performed under comparatively high temperature conditions (for example, 70° C. or higher), and therefore if a mesophile-derived enzyme is used, loss of activity may be a concern. Accordingly, an alkaline phosphatase derived from the hyperthermophile Pyrococcus furiosus (PfuAP) is preferred as the target enzyme.

Enzymes derived from hyperthermophiles are known to generally exhibit a high level of stability relative to organic solvents and heat, and are therefore preferred (for example, see H. Atomi, Current Opinion in Chemical Biology, 9, pp. 166 to 173 (2005)), and are also preferred in terms of being comparatively easy to prepare in large quantities using a coli bacteria host. When preparing a heat-resistant enzyme using a coli bacteria host, by subjecting the cell homogenate to a high-temperature treatment (for example, by holding at 80° C. for 30 minutes), substantially all of the contaminant protein derived from the coli bacteria can be precipitated, enabling a crude purification to be performed with comparative ease.

Hyperthermophiles are microbes that can grow in extreme environments in which most bioorganisms cannot survive, and therefore hyperthermophile-derived proteins exhibit extremely high levels of heat resistance. Moreover, not only do they exhibit excellent resistance to heat, but generally also have much higher resistance to denaturants, organic solvents and pH and the like than mesophile-derived enzymes. Accordingly, it is thought that by using PfuAP, a more precise double strand formation can be achieved with no loss of enzyme activity.

An example of a preferred configuration of the enzyme-multilabeled nucleic acid probe according to the present embodiment is a complex of PfuAP and Z-QG RNA. In this type of complex, the stable enzyme PfuAP and the stable molecule of RNA are bound via stable covalent bonding provided by amide linkages, and therefore the overall complex also offers the advantage of favorable stability.

Further, in the enzyme-multilabeled nucleic acid probe, the enzyme may be stable relative to organic solvents and heat. This type of high-stability enzyme can be obtained by screening from the natural world (for example, see Chemistry and Chemical Industry, vol. 61 (No. 6), pp. 571 to 575 (2008), Taku Uchiyama and Kentaro Miyazaki, Bioscience and Industry, vol. 66 (No. 5), pp. 234 to 239 (2008), and Noriyuki Dokyu, Bioscience and Industry, vol. 66 (No. 12), pp. 667 to 670 (2008)), or by techniques for increasing the stability using protein engineering (for example, see Hiroyasu Ogino, Bio Industry, vol. 25 (No. 7), pp. 16 to 23 (2008), and Kentaro Miyazaki, Bio Industry, vol. 25 (No. 7), pp. 52 to 58 (2008)). By using these techniques, even enzymes derived from mesophiles can be converted to enzymes that exhibit favorable organic solvent resistance and heat resistance.

Labeling compounds containing an introduced fluorescent dye portion and having a lysine (Lys) residue or primary amine can be prepared, for example, by introducing a diamine at a carboxyl group (for example, see G. T. Hermanson (1996), Bioconjugate Techniques, chapter 1, section 4.3, pp. 100 to 104, Academic Press, San Diego).

A variety of enzymes can be used as the transglutaminase (TGase). Currently known TGase varieties include those derived from mammals (guinea pig and human), invertebrates (insects, horseshoe crab, sea urchin), plants, bacteria and protists (myxomycetes), and in the case of human-derived TGase, eight isozymes have been discovered. An example of a preferred TGase for use in the present embodiment, particularly in terms of stability, ease of handling, bulk producibility or the like, is microbial transglutaminase (MTG).

When MTG is used in the present embodiment, then based on the expected MTG catalysis, the binding reaction between the labeling compound containing a labeling portion such as a labeling enzyme having a Lys residue and the Z-QG RNA is predicted to proceed in two stages, namely formation of an acyl-enzyme complex via a nucleophilic substitution reaction of the cysteine (Cys) residue that represents the MTG active center at the Gln of the Z-QG RNA, and a subsequent elimination of the MTG via a nucleophilic substitution reaction at the acyl-enzyme complex by the Lys of the labeling compound.

In a preferred configuration of the present embodiment, the molar concentration ratio of the labeling compound having a TGase-recognizable Lys residue or primary amine, relative to the Z-QG RNA having a TGase-recognizable Gln residue is preferably 2 or greater, and is more preferably 5 or greater. When the abbreviated term "concentration ratio" is used in this description, unless specifically stated otherwise, the term refers to a ratio between molar concentrations. For example, the molar concentration ratio of NK14-PfuAP relative to Z-QG RNA is expressed as [NK14-PfuAP]/[Z-QG RNA].

[Preparation of NK14-PfuAP]

NK14-PfuAP is a structure in which an additional sequence composed of an amino acid 14 residue having the sequence MKHKGGGSGGGSGS is introduced at the PfuAP N-terminal by genetic engineering, and a purification tag is introduced at the C-terminal. The expression vector for PfuAP was received from Professor Haruhiko Sakuraba of Kagawa University. During amplification of the PfuAP coding region by PCR, recombination with the protein expression vector pET22 was conducted so as to introduce both tags, and the coli bacterium BL21 was transformed. Following preculture in an LB medium containing ampicillin and subsequent main culture, the resulting transformant was collected by centrifugal separation, and then washed twice with 25 mM TBS. Following freezing and thawing of the thus obtained microbe, the cells were pulverized by an ultrasonic treatment, and then centrifugal separation was used to collect the soluble fraction. The hyperthermophile-derived PfuAP is stable even under high-temperature conditions, and therefore a crude purification was performed by treating the obtained cell-free extract at 80° C. for 30 minutes, thus precipitating other proteins. Following this crude purification, the supernatant was collected by centrifugal separation and filtration, and subsequently purified using a His-tag column. Following purification, the liquid was concentrated by ultrafiltration, a PD-10 column was used to substitute the solvent medium with 10 mM Tris-HCl (pH 8.0), and the sample was frozen and stored until testing.

Furthermore, in order to improve the expression of the NK14-PfuAP in the coli bacteria, the expression vector of an NK14-PfuAP in which the base sequence has been altered in accordance with the coli bacteria codon usage frequency (accession number: AB479383, sequence number: 26) may be used. This expression vector was obtained via custom synthesis by Codon Devices, Inc. (http://www.codondevices.

com). An appropriate restriction enzyme site was introduced at both terminals of the gene region for coding the NK14-PfuAP, these sites were used to achieve recombination with the protein expression vector pET22, and the coli bacterium BL21 was transformed by the resulting NK14-PfuAP expression vector. Following preculture in an LB medium containing ampicillin and subsequent main culture, the resulting transformant was collected by centrifugal separation, and then washed twice with 25 mM TBS. Following freezing and thawing of the thus obtained microbe, the cells were pulverized by an ultrasonic treatment, and then centrifugal separation was used to collect the soluble fraction. The hyperthermophile-derived PfuAP is stable even under high-temperature conditions, and therefore a crude purification was performed by treating the obtained cell-free extract at 80° C. for 30 minutes, thus precipitating other proteins. Following this crude purification, the supernatant was collected by centrifugal separation and filtration, and subsequently purified using a His-tag column. Following purification, the liquid was concentrated by ultrafiltration, a PD-10 column was used to substitute the solvent medium with 10 mM Tris-HCl (pH 8.0), and the sample was frozen and stored until testing.

In those cases where MTG is used as the TGase in the binding reaction, then in addition to ensuring that the molar concentration ratio satisfies a specific range as described above, the reaction is preferably performed at a pH of 5.5 to 8.0 and at a temperature of 4 to 50° C. (for example, at room temperature (18 to 22° C.)). Under such conditions, a satisfactorily high reaction rate can be achieved within 12 hours, preferably within 6 hours, and more preferably within 3 hours.

The solution of the multilabeled nucleic acid probe obtained using this type of method that yields a high reaction rate contains substantially no unreacted nucleic acid probe (such as free Z-QG RNA), and even if the solution is used without further treatment in the detection of the target nucleic acid, which is described below in detail, essentially no competition occurs between the multilabeled nucleic acid probe and unreacted molecules, or even if such competition does occur, it is thought to be sufficiently minimal to have no substantial effect on the results of the target detection. Accordingly, the multilabeled nucleic acid probe solution offers the advantage of being able to be used directly for detection, without requiring purification.

Prior to this embodiment, no known examples existed of multilabeled nucleic acid probes obtained by using a TGase to bind a labeling compound such as a labeling enzyme having a TGase-recognizable Lys residue or primary amine to a Z-QG RNA having a TGase-recognizable Gln residue. Accordingly, the multilabeled nucleic acid probe generated using the method of the present embodiment can be claimed to be a novel material.

The method for forming the enzyme-multilabeled nucleic acid probe in the present embodiment has the following features and advantages compared with conventional methods.

The target enzyme includes enzymes having a TGase-recognizable Lys residue or a primary amine, and all manner of enzymes into which a TGase-recognizable Lys residue or a primary amine can be introduced. Further, large protein tags such as intein are unnecessary.

The modification region of the enzyme is not limited to the C-terminal. Modification can occur at any region where a TGase-active Lys residue exists, or where a tag having such a Lys residue can be introduced.

In addition to the C-terminal and N-terminal, regions having a high degree of fluctuation within the protein structure, such as a loop region, can also function as the modification target.

There are no particular limitations on the base sequence or length of the bound nucleic acid.

<Method for Detecting Target Nucleic Acid>

The method for detecting a target nucleic acid according to an embodiment of the present invention comprises: preparing a multilabeled nucleic acid probe, which comprises a labeling compound such as a labeling enzyme having a lysine (Lys) residue or a primary amine bound to each of at least two glutamine (Gln) residues within a nucleic acid probe, which is a nucleic acid in which a plurality of nucleoside triphosphate derivatives represented by one of the above formulas (1) to (5) have been introduced as structural units, wherein the multilabeled nucleic acid probe has a labeling portion that is readily detectable, and has a nucleic acid portion with a base sequence that binds specifically with the target nucleic acid; performing specific binding of the nucleic acid portions of the multilabeled nucleic acid probe and the target nucleic acid within the target material; and detecting the bound multilabeled nucleic acid probe via the labeling portion such as the enzyme portion.

The method for detecting a target nucleic acid according to the present embodiment can be used for qualitative or quantitative analysis, or for identification, staining or localization or the like of the target nucleic acid.

In this method, the multilabeled nucleic acid probe described above is used, and the nucleic acid portion has a nucleic acid sequence that can bind specifically with the target nucleic acid. The labeling portion such as the enzyme portion has a readily detectable property. In this method, the target molecule containing the target nucleic acid may be a nucleic acid, a comparatively low molecular weight organic compound (ATP), a protein, a peptide, a metal ion, a multimer having a complex structure, or a virus or the like. The detection target may be (i) a DNA transfer membrane, or (ii) a cell or solid tissue section or the like.

In the case of a detection target (i), the target nucleic acid is a DNA or genomic fragment DNA that has been amplified by PCR, whereas in the case of a detection target (ii), the target nucleic acid is a nucleic acid (mRNA or DNA) contained within a cell or solid tissue. This method is superior to conventional methods that use, for example, a digoxigenin (DIG)-labeled probe in a number of respects. For example, in a DIG method, DIG modification of the nucleic acid probe and a labeled anti-DIG antibody are required, and as a result the method requires complex washing operations, whereas if the multilabeled nucleic acid probe according to the present embodiment is used, then neither a DIG-labeled probe nor a labeled anti-DIG antibody are required, meaning the number of reagents, and the amount of time and effort can be reduced considerably. Further, because a plurality of signal amplification regions (such as enzymes) are located within a single recognition region (nucleic acid), the detection sensitivity can be improved.

In this method, the multilabeled nucleic acid probe is supplied to the target nucleic acid, and the target nucleic acid is hybridized with the portion of the multilabeled nucleic acid probe that has a sequence complementary to the target nucleic acid, and the conditions for this hybridization can be designed appropriately by a person skilled in the art in accordance with the length and base sequence and the like of the nucleic acid portions being used.

In the method for detecting a target nucleic acid according to the present embodiment, a plurality of multilabeled nucleic acid probes having different labeling portions such as different enzymes or different fluorescent dyes may be prepared, and a plurality of target nucleic acids then detected simultaneously.

Furthermore, in the present embodiment, the method for detecting a target nucleic acid comprises: preparing (a) a nucleic acid immobilized on a substrate surface, (b) an aptamer nucleic acid having a sequence that is complementary to all or part of the immobilized nucleic acid (an immobilized nucleic acid complementary sequence), and a sequence that can bind specifically to the target nucleic acid (a target nucleic acid-specific sequence), and (c) a multilabeled nucleic acid probe, which comprises a labeling compound such as a labeling enzyme having a lysine (Lys) residue or a primary amine bound to each of at least two glutamine (Gln) residues within a nucleic acid probe, which is a nucleic acid in which a plurality of nucleotide derivatives represented by the above formula (1) or the like have been introduced as structural units, wherein the multilabeled nucleic acid probe has a labeling portion that is readily detectable, and/or has a nucleic acid portion with a sequence that is complementary to all or part of the target nucleic acid-specific sequence of the aptamer nucleic acid, and subsequently (A) supplying the aptamer nucleic acid to the immobilized nucleic acid, and hybridizing the immobilized nucleic acid and the portion of the aptamer nucleic acid having the immobilized nucleic acid complementary sequence, thereby immobilizing the aptamer nucleic acid, (B) supplying the sample that may comprise a target molecule containing the target nucleic acid to the immobilized aptamer nucleic acid, and in those cases where the target molecule does exist, binding the target nucleic acid to the portion of the aptamer nucleic acid having the target nucleic acid-specific sequence, and then supplying the above-mentioned multilabeled nucleic acid probe, and in those cases where the target molecule does not exist, hybridizing the nucleic acid portion of the multilabeled nucleic acid probe and the aptamer nucleic acid, thereby immobilizing the protein, and (C) detecting the existence of, and the amount of, the immobilized enzyme portion based on the properties of the enzyme, thereby detecting the target molecule within the sample.

In order to immobilize the nucleic acid on the substrate surface in this invention, conventional techniques such as the techniques used during the preparation of DNA microarrays can be applied. The "substrate" may be a chip, beads, a well, or a plate or the like made of glass, silicon or plastic or the like, and the nucleic acid can be immobilized on the substrate surface by non-covalent binding (electrostatic binding) or covalent binding using conventional techniques. A nucleic acid that has been prepared in advance may be immobilized on the substrate, or the nucleic acid may be synthesized directly on the substrate. For the sake of convenience, a commercially available plate coated with avidin or the like can be used, and a biotinylated desired DNA then immobilized on the plate.

In this method, a nucleic acid (aptamer nucleic acid) having a sequence that is complementary to all or part of the immobilized nucleic acid (an immobilized nucleic acid complementary sequence), and a sequence that can bind specifically to the target nucleic acid contained within a target molecule (a target nucleic acid-specific sequence) is used. The target molecule may be a nucleic acid, a comparatively low molecular weight organic compound, a protein, a peptide, a metal ion, a multimer having a complex structure, or a virus or the like. The portion having the target nucleic acid-specific sequence can be produced using conventional techniques, for example by using a SELEX step (an in vitro artificial evolution method). Further, this portion may exhibit extremely high target affinity and specificity for the target molecule. The portion having the target nucleic acid-specific sequence may be composed of a modified nucleotide.

In this method, the multilabeled nucleic acid probe described above is used, wherein the nucleic acid portion of the probe has a sequence that is complementary to all or part of the target nucleic acid-specific sequence of the aptamer nucleic acid. The labeling portion such as the enzyme portion has a readily detectable property. In this method, the target molecule containing the target nucleic acid may be a nucleic acid, a comparatively low molecular weight organic compound (ATP), a protein, a peptide, a metal ion, a multimer having a complex structure, or a virus or the like. The detection target may be (i) a DNA transfer membrane, or (ii) a cell or solid tissue section or the like.

In this method, the aptamer nucleic acid is immobilized by supplying the aptamer nucleic acid to the immobilized nucleic acid, and hybridizing the immobilized nucleic acid with the portion of the aptamer nucleic acid having the immobilized nucleic acid complementary sequence, and the conditions for this hybridization can be designed appropriately by a person skilled in the art in accordance with the length and base sequence and the like of the nucleic acid portions being used.

Further, in this method, a sample that may comprise the target molecule is subsequently supplied to the immobilized nucleic acid, and in those cases where the target molecule does exist, the target molecule is bound to the portion of the aptamer nucleic acid having the target nucleic acid-specific sequence, and the above-mentioned multilabeled nucleic acid probe is then supplied, and in those cases where the target molecule does not exist, the nucleic acid portion of the multilabeled nucleic acid probe and the aptamer nucleic acid are hybridized. The sample may be a cell or tissue extract, or a bodily fluid or the like.

Moreover, in this method, the existence of, or the amount of, the immobilized enzyme portion can be detected based on the properties of the enzyme, thus enabling detection of the target molecule within the sample.

The aptamer nucleic acid can be designed so that the portion having the immobilized nucleic acid complementary sequence and the portion having the target nucleic acid-specific sequence overlap, are positioned in a consecutive arrangement, or exist with a suitable spacer disposed therebetween. Considering the fact that the portion having the target nucleic acid-specific sequence (the aptamer region) adopts a certain three dimensional structure in order to achieve molecular recognition, this portion may, at the least, preferably not overlap with the portion having the immobilized nucleic acid complementary sequence.

If required, the aptamer nucleic acid may also comprise, besides the immobilized nucleic acid complementary sequence and the target nucleic acid-specific sequence, a sequence for undergoing suitable hybridization with the multilabeled nucleic acid probe. The nucleic acid portion of the multilabeled nucleic acid probe has a sequence that is complementary to all or part of the target molecule-specific sequence of the aptamer nucleic acid, but if the region comprising the sequence that is complementary to all or part of the specific sequence is long (so that the overlap with the target nucleic acid-specific sequence is large), then in some cases, hybridization with the aptamer nucleic acid may actually be impossible. Further, if the region is too short (with minimal overlap), then even in those cases where the target molecule exists and has bound to the aptamer nucleic acid, the multilabeled nucleic acid probe and the aptamer nucleic acid may still undergo hybridization. A person skilled in the art will be able to take these factors into consideration when designing the immobilized nucleic acid, the aptamer nucleic acid and the nucleic acid portion of the multilabeled nucleic acid probe.

Furthermore, a method for detecting a target nucleic acid according to an embodiment of the present invention comprises: performing specific binding, via the nucleic acid portions, of a nucleic acid probe, in which the nucleic acid portion is a nucleic acid having a base sequence that can bind specifically with a target nucleic acid and in which a plurality of nucleoside triphosphate derivatives represented by one of the above formulas (1) to (5) have been introduced as structural units, and a target nucleic acid that exists within the target material, subsequently introducing a plurality of labeling portions having a readily detectable property by using a transglutaminase (TGase) to react glutamine (Gln) residues within the nucleic acid probe with a lysine (Lys) residue or a primary amine of a labeling compound having a lysine (Lys) residue or a primary amine and containing a labeling portion, and then detecting the bound nucleic acid probe via the labeling portion (see FIG. 16).

In this method, the nucleic acid probe described above is used, and the nucleic acid portion has a nucleic acid sequence capable of binding specifically with the target nucleic acid. Further, the labeling portion has a readily detectable property.

This method is superior to conventional methods that use, for example, a digoxigenin (DIG)-labeled probe in a number of respects. For example, in a DIG method, DIG modification of the nucleic acid probe and a labeled anti-DIG antibody are required, and as a result the method requires complex washing operations, whereas if the nucleic acid probe according to the present embodiment is used, then neither a DIG-labeled probe nor a labeled anti-DIG antibody are required, meaning the number of reagents, and the amount of time and effort can be reduced considerably. Further, because a plurality of signal amplification regions (labeling portions) are located within a single recognition region (nucleic acid), the detection sensitivity can be improved.

For example, using a TGase such as MTG, a labeling compound such as an enzyme or fluorescent dye having an introduced TGase-recognizable Lys can be bound to a nucleic acid probe Z-QG RNA containing introduced TGase-recognizable Gln residues such as MTG-recognizable Gln residues at a plurality of locations.

EXAMPLES

A more detailed description of the present invention is presented below based on a series of examples and comparative examples, although the present invention is in no way limited by the following examples.

In the present invention, hyperthermophile-derived enzyme-multilabeled RNA was developed with the aim of application to in situ hybridization (ISH). The protein modification ability of microbial transglutaminase (MTG) was used to perform the enzyme labeling. ZQG-UTP, which contains an introduced Z-QG that acts as a good substrate for MTG, was synthesized, and a transcription reaction using RNA polymerase was then used to prepare Z-QG RNA. Subsequently, MTG was used to prepare a hyperthermophile-derived enzyme-multilabeled nucleic acid probe, and the performance of the probe was then evaluated by dot blots.

Example 1

Synthesis and Purification of Z-QG-UTP

The scheme for the synthesis of Z-QG-UTP is as illustrated in FIG. 3.

First, 100 mM of N,N'-diisopropylcarbodiimide (DIC), 100 mM of N-hydroxysuccinimide (NHS) and 50 mM of Z-QG were reacted for 20 hours at room temperature (27.0° C. on the day of preparation) in 4 mL of N, N-dimethylformamide (DMF), thus yielding NHS-modified Z-QG (50 mM) (which at this stage was divided into 500 µL portions and stored at −80° C.). Subsequently, 25 mM of the NHS-modified Z-QG and 5 mM of 5-(3-aminoallyl)-UTP (hereinafter abbreviated as "aminoallyl-UTP", manufactured by Sigma-Aldrich Co., Ltd.) were reacted for 12 hours at 25° C. in 0.32 mL of a mixed solvent (v/v=1/1) of a 100 mM boric acid buffer solution (pH 8.8) and DMF. Following completion of the reaction, a sample was diluted 10-fold with Milli-Q, and purification was performed by HPLC (manufactured by JASCO Corporation) (high-performance liquid chromatograph and pump: TRI ROTAR-V series, variable loop injector: model VL-613, ultraviolet-visible spectroscopic detector: model UVIDEC-100-IV). The HPLC measurement conditions were as listed in Table 1. Identification of the product was performed using a laser ionization time-of-flight mass spectrometry apparatus MALDI TOF-MS (AXIMA (a registered trademark)-CFR Plus, manufactured by Shimadzu Corporation). The sample preparation sequence involved first dripping 1 µL of the sample onto a MALDI sample plate, subsequently dripping a matrix solution (a 10 mg/ml solution (in ultra pure water) of 2,5-dihydroxybenzoic acid (DHB)) onto the top of the plate, blow drying the plate, and then introducing the thus prepared sample plate into the ion source of the MALDI TOF-MS apparatus for measurement.

Figure 4:
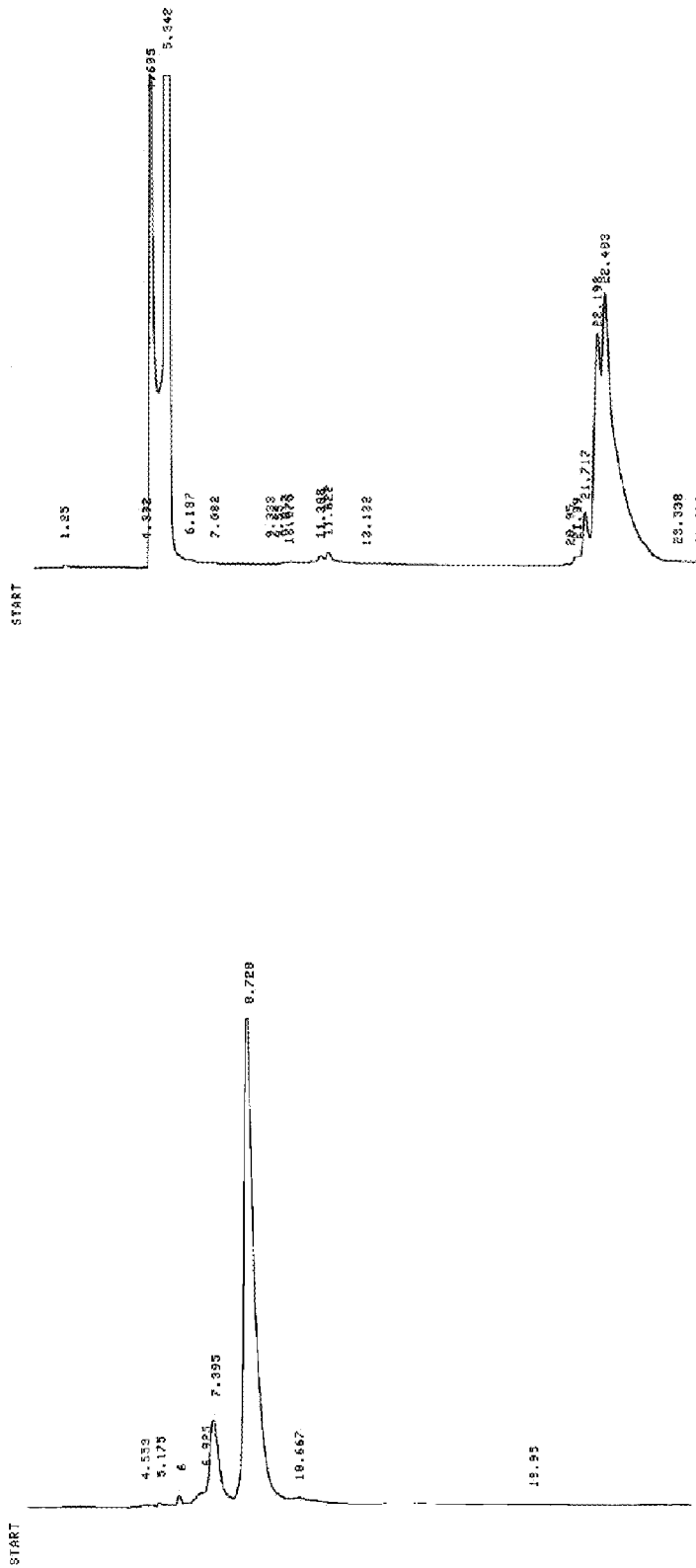
FIG. 4A is a diagram illustrating the results of performing reverse phase HPLC (under the HPLC measurement conditions listed in Table 1) of aminoallyl-UTP in example 1 of the present invention.
FIG. 4B is a diagram illustrating the results of performing reverse phase HPLC (under the HPLC measurement conditions listed in Table 1) following the synthesis of Z-QG-UTP in example 1 of the present invention.
Figure 5:
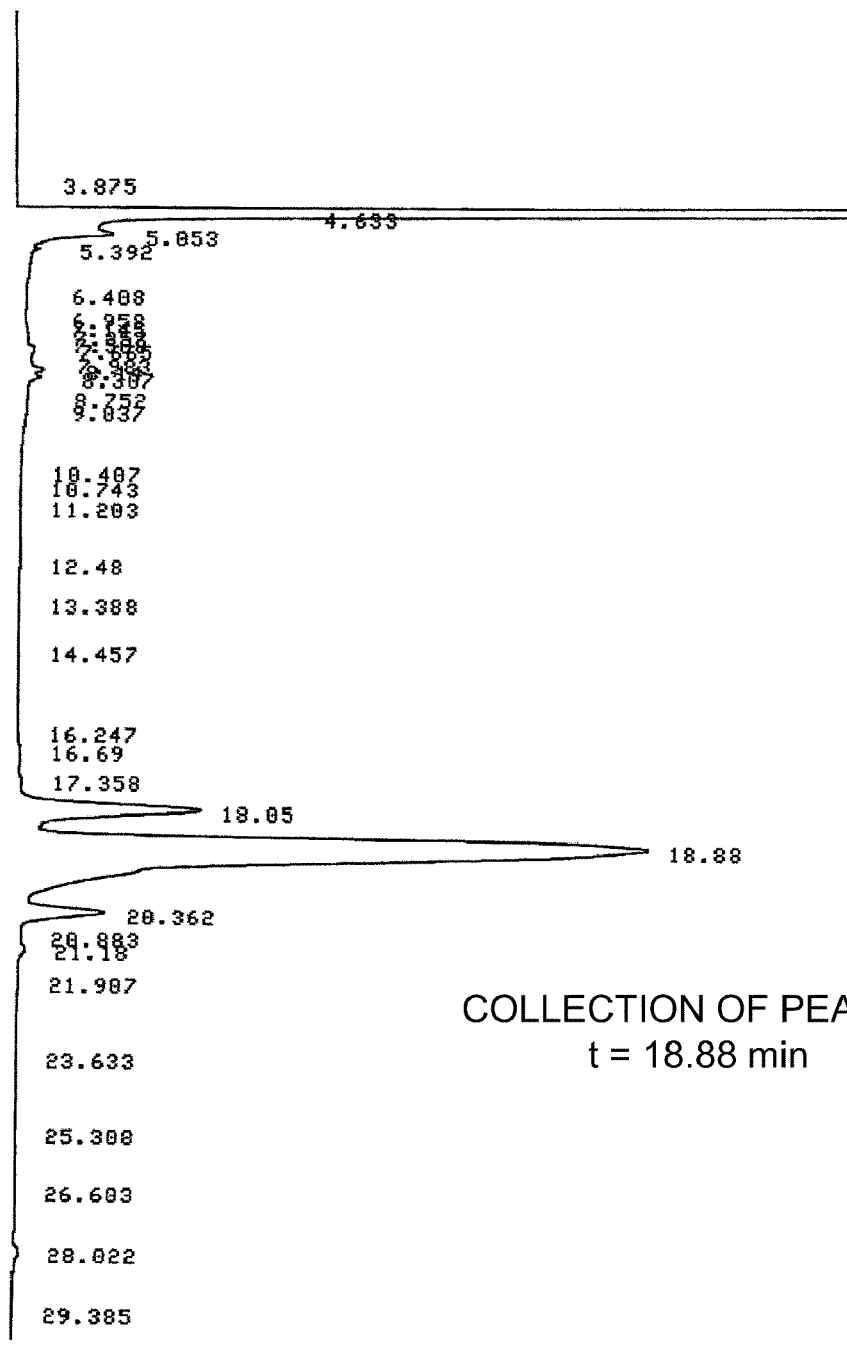
FIG. 5 is a diagram illustrating the results of performing reverse phase HPLC (under the HPLC measurement conditions listed in Table 2) following the synthesis of Z-QG-UTP in example 1 of the present invention.

The results of performing reverse phase HPLC under the conditions listed in Table 1 following synthesis of the Z-QG-UTP are illustrated in FIG. 4. Compared with the results obtained for aminoallyl-UTP (FIG. 4A), a new peak appeared at the hydrophobic side (22 min) (FIG. 4B), and it was assumed that this peak represents the Z-QG-UTP. However, separation of the product peak was inadequate, and therefore an investigation was performed in which the HPLC conditions were altered to those listed in Table 2. The results are illustrated in FIG. 5.

TABLE 1

| HPLC measurement conditions | |
|---|---|
| Column | Inertsil ODS-3 (4.6 mm × 250 mm) |
| Solvent | A = 50 mM TEAA (pH 7.0), B = acetonitrile |
| Gradient | A = 98% → 58% (40 min) |
| Flow rate | 1.0 mL/min |
| Detection wavelength | 260 nm |

TABLE 2

| HPLC measurement conditions | |
|---|---|
| Column | Inertsil ODS-3 (10 mm × 250 mm) |
| Solvent | A = 100 mM TEAA (pH 7.0), B = acetonitrile |
| Gradient | A = 98% → 88% (5 min) |
| | 88% → 73% (30 min) |
| | 73% → 98% (10 min) |
| Flow rate | 5.0 mL/min |
| Detection wavelength | 260 nm |

Figure 6:
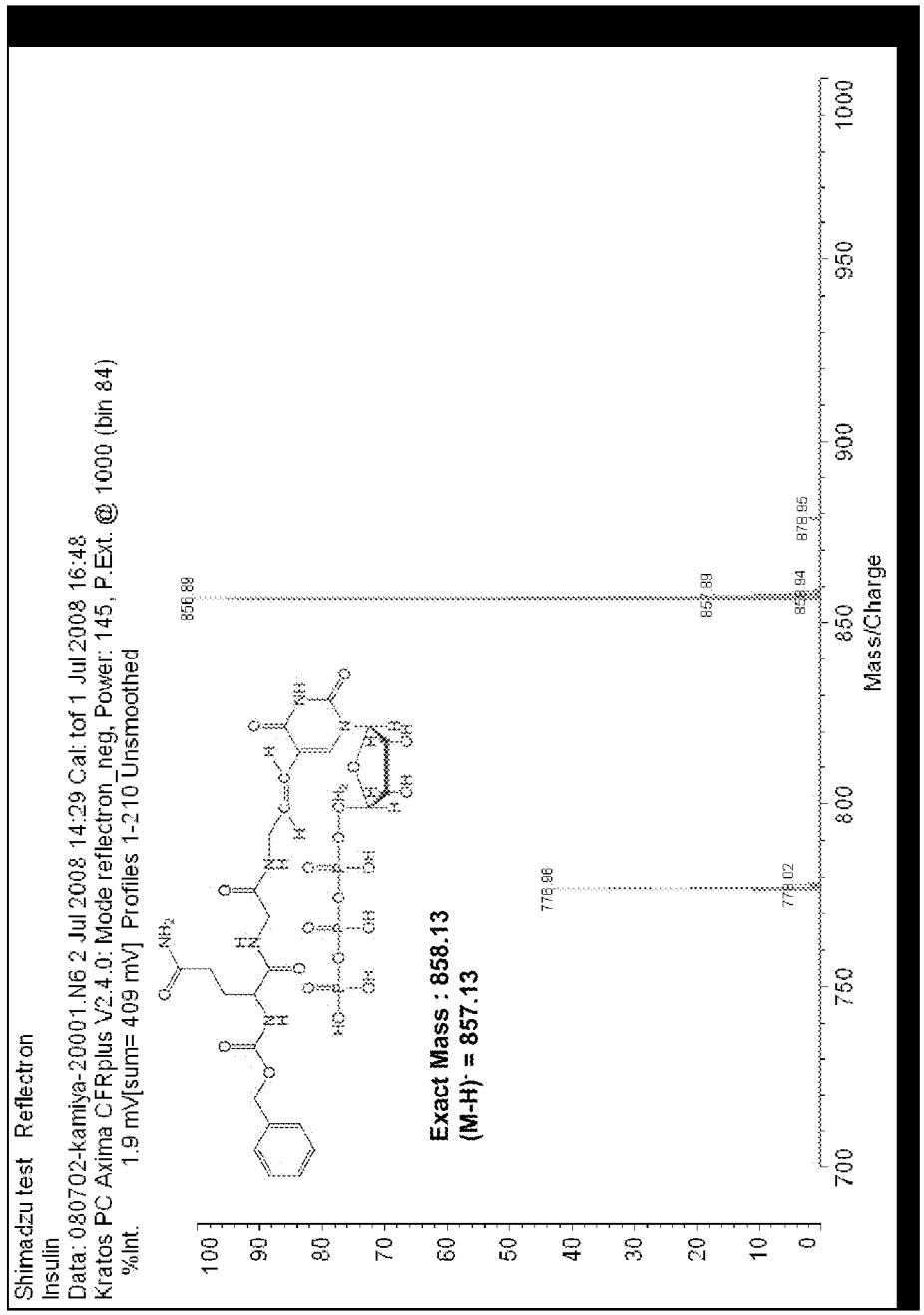
FIG. 6 is a diagram illustrating the results of performing a MALDI TOF-MS analysis of the Z-QG-UTP synthesized in example 1 of the present invention.

The peak at a retention time of 18.8 minutes was collected and analyzed by MALDI TOF-MS (see FIG. 6). As a result, a peak was confirmed at 856.89, which represents a good match with the theoretical molecular weight of 857.13 and therefore indicates the synthesis of Z-QG-UTP.

[Test 1: Evaluation of Detection Sensitivity of Alkphos Direct Kit]

<Preparation of Sense Chain RNA and Antisense Chain RNA>

By performing a transcription using RNA polymerase, a sense chain RNA and antisense chain RNA were prepared. As a target nucleic acid (the target), an mRNA (shh) that codes the protein known as Sonic hedgehog (SHH), which has a known expression pattern within mice, was used as a model. First, PCR was conducted using a plasmid containing an SHH-coded gene as a template, yielding a DNA fragment with a length of approximately 1,000 bp. Primer design was conducted so that a T3 promoter was introduced upstream and a T7 promoter was introduced downstream. Subsequently, using the obtained PCR product as a substrate, an RNA synthesis was conducted using T3 polymerase (for preparing a sense chain (S)), thereby effecting a transcription reaction with the T3 polymerase and preparing a sense chain sequence (sequence number: 24). In a similar manner, an RNA synthesis was conducted using T7 polymerase (for preparing an antisense chain (AS)), thereby effecting a transcription reaction with the T7 polymerase and synthesizing an antisense chain sequence (sequence number: 25). The conditions are listed below in Table 3. Reaction was conducted for 2 hours at 37° C., and the obtained sense chain RNA and antisense chain were recovered by precipitation in ethanol, and were then suspended in 20 μL of a TE buffer. RNase inhibitor and DTT were then added to suppress decomposition by RNase.

TABLE 3

| In vitro transcription conditions | |
| --- | --- |
| Components | Amount added |
| Template (220 ng/μL) | 2 μL |
| 10 × Buffer | 2 μL |
| 10 × NTP Mix | 2 μL |
| RNase Inhibitor (40 U/μL) | 1 μL |
| Sterilized water | 11 μL |
| T3 or T7 polymerase | 2 μL |

<Measurement of RNA Concentration>

Following the transcription reaction, the RNA concentration was measured using a Nano prop device. The results revealed a sense chain concentration of 1,019 ng/μl, and an antisense chain concentration of 815 ng/μL.

<Preparation of Labeled Probe>

A labeled probe was prepared using the reagents provided with an Alkphos Direct kit (a registered trademark, manufactured by GE Healthcare Bioscience Bioprocess Corporation). First, 60 μL of a sample prepared by diluting the above antisense chain RNA to a concentration of 10 ng/μL with sterilized water (total amount: 600 ng) was heat-denatured at 99.9° C., and was then cooled rapidly. 60 μL of the reaction buffer, 12 μL of the labeling reagent and 60 μL of the cross-linker solution appended to the kit were added, in that order, to the heat-denatured RNA, and the mixture was incubated at 37° C. for 30 minutes to complete preparation of a labeled probe.

<Preparation of Detection Membrane>

First, 1 μL of each of a series of samples prepared by using sterilized water to dilute the sense chain RNA and antisense chain RNA targets to 6 different concentration stages within the range from 1 pg/μL to 50 ng/μL was applied to a positively charged membrane (Hybond N+, manufactured by GE Healthcare Bioscience Bioprocess Corporation). Subsequently, each sample was baked at 80° C. for 2 hours.

<Hybridization>

The membrane prepared in the above detection membrane preparation was transferred to the hybridization buffer appended to the kit, and a pre-hybridization was performed at 55° C. for 5 minutes. Subsequently, the standard probe described above was added in an amount sufficient to achieve a concentration of 50 ng/mL, and hybridization was conducted overnight (approximately 14 to 16 hours) at 55° C.

<Membrane Washing>

Following hybridization, the membrane was transferred to a Wash I buffer (Table 4) and was washed by shaking for 15 minutes at 55° C. This operation was performed twice. Subsequently, the membrane was washed in a Wash II buffer (Table 5). This operation was also performed twice.

TABLE 4

| Composition of Wash I buffer | |
| --- | --- |
| Component | Final concentration |
| Urea | 2M |
| SDS | 0.1% |
| Na phosphate (pH 7.0) | 50 mM |
| NaCl | 150 mM |
| $MgCl_2$ | 1 mM |
| Blocking reagent | 0.2% |

TABLE 5

| Composition of Wash II buffer | |
| --- | --- |
| Component | Final concentration |
| Tris base | 50 mM |
| NaCl | 100 mM |
| $MgCl_2$ | 2 mM |

<Detection by Color Development Method>

The membrane was washed for 5 minutes at room temperature (approximately 18 to 22° C. on the day of testing) in a NTMTx buffer (Table 6), and was then transferred to a staining solution (375 μg/mL NBT+188 μg/mL BCIP in NTMTx), and color development was performed for two hours at room temperature under blackout conditions. NBT is an abbreviation for nitro blue tetrazolium chloride, and BCIP is 5-bromo-4-chloro-3-indolyl phosphate, toluidine salt.

TABLE 6

| Composition of NTMTx buffer | |
| --- | --- |
| Component | Final concentration |
| NaCl | 100 mM |
| Tris-HCl (pH 9.5) | 100 mM |
| $MgCl_2$ | 50 mM |
| Triton X-100 | 0.1% |

Figure 7:
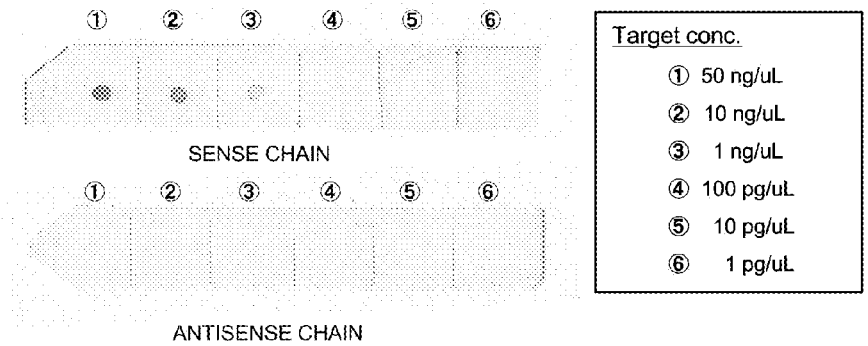
FIG. 7 is a diagram illustrating the results of dot blots using a standard probe of test 1 in example 1.

The results of dot blots are illustrated in FIG. 7. The membrane of the probe and the complementary sense chain was able to be detected down to the 100 pg/μL dot. Further, even for the antisense chain, a faint signal was observed for the 50 and 10 ng/μL dots. This results suggests there is a possibility that the template DNA used during preparation of the target RNA was unable to be treated by the DNaseI and remained within the sample. Further, another possibility is that the temperature decreased during the washing operations, and the resulting reduction in stringency may have caused non-specific adsorption.

[Test 2: Evaluation of Detection Sensitivity for the Case where a TGase Substrate-Multilabeled Nucleic Acid Probe was Used in a System According to Alkphos Direct Protocol]
<Preparation of TGase Substrate-Multilabeled Nucleic Acid>

In addition to the preparation of the sense chain RNA and antisense chain RNA described above for test 1, TGase substrate-multilabeled nucleic acids were also prepared in a similar manner using T7 polymerase in accordance with the conditions listed in Table 7 and Table 8. Following preparation, the nucleic acids were treated with DNaseI, and the RNA was concentrated and purified by precipitation in ethanol, and then suspended in 20 µL of a TE buffer. RNase inhibitor and DTT were also added, completing preparation of novel enzyme-multilabeled nucleic acid probes.

TABLE 7

In vitro transcription conditions for TGase substrate-multilabeled nucleic acid probes

| Component | Amount added |
|---|---|
| Template DNA (SHH PCR Product: 400 ng/µL) | 2 µL |
| 10x Buffer | 2 µL |
| 10 mM NTP Mix (Table 8) | 2 µL |
| RNase Inhibitor (40 U/µL) | 1 µL |
| Sterilized water | 11 µL |
| T7 polymerase | 2 µL |
| Total | 20 µL |

TABLE 8

Composition of various NTP Mixes

| NTP | (1) Z-QG-UTP 0% | (2) Z-QG-UTP 20% | (3) Z-QG-UTP 40% | (4) Z-QG-UTP 60% | (5) Z-QG-UTP 80% | (6) Z-QG-UTP 100% |
|---|---|---|---|---|---|---|
| ATP, CTP, GTP | 10 mM | 10 mM | 10 mM | 10 mM | 10 mM | 10 mM |
| UTP | 10 mM | 8 mM | 6 mM | 4 mM | 2 mM | 0 mM |
| Z-QG-UTP | 0 mM | 2 mM | 4 mM | 6 mM | 8 mM | 10 mM |

<Measurement of RNA Concentration>

Following the transcription reaction, the RNA concentration was measured using a Nano Drop device. The results of the measurements are listed below.

(1) Z-QG-UTP 0%: 410 ng/µL
(2) Z-QG-UTP 20%: 424 ng/µL
(3) Z-QG-UTP 40%: 378 ng/µL
(4) Z-QG-UTP 60%: 368 ng/µL
(5) Z-QG-UTP 80%: 311 ng/µL
(6) Z-QG-UTP 100%: 256 ng/µL

<Preparation of Labeled Probe>

TGase substrate-multilabeled nucleic acids containing different proportions of Z-QG-UTP were heat-denatured for 5 minutes at 99.9° C., and were then cooled rapidly. Using the heat-denatured nucleic acids, a series of reaction solutions were prepared under the conditions listed in Table 9, and each solution was then reacted at 4° C. for 6 hours to prepare an enzyme-multilabeled probe (sequence number: 23).

TABLE 9

Reaction conditions

| Component | Final concentration |
|---|---|
| Z-QG RNA | 50 ng/uL |
| pfuAP | 0.4 mg/mL |
| MTG | 5 U/mL |
| Tris-HCl (pH 8.0) | 100 mM |
| RNase inhibitor | 1 U/uL |

Subsequently, preparation of detection membranes, hybridization, and membrane washing were performed in the same manner as described above for test 1.

<Detection by Color Development Method>

Figure 8:
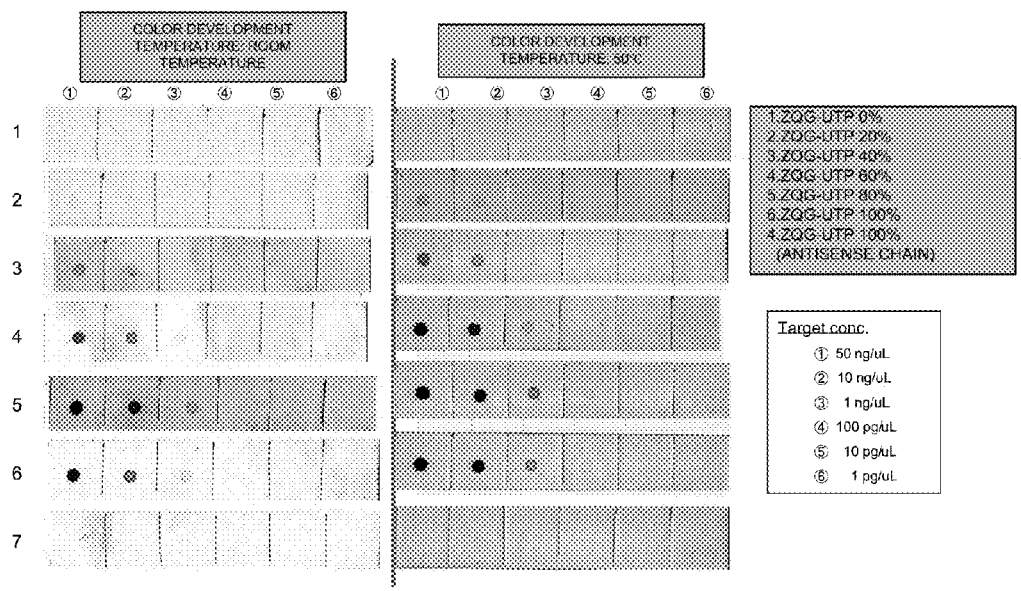
FIG. 8 is a diagram illustrating the results detected in accordance with Alkphos Direct protocol using enzyme-multilabeled nucleic acid probes of test 2 in example 1.

With the exception of setting the temperature during color development to room temperature (approximately 18 to 22° C. on the day of testing) or 50° C., detection was conducted in accordance with the color development method described for test 1. The results detected in accordance with Alkphos Direct protocol using the enzyme-multilabeled nucleic acid probes are illustrated in FIG. 8. In those cases where color development was conducted at room temperature, detection was capable down to 10 ng/µL for the probes having a Z-QG-UTP proportion of 20 to 40%, and down to 1 ng/µL for the probes having a Z-QG-UTP proportion of 60 to 100%. Further, when color development was conducted at 50° C., detection was capable down to 10 ng/µL for a Z-QG-UTP proportion of 20%, down to 1 ng/µL for Z-QG-UTP proportions of 40 to 60%, and down to 100 pg/µL for Z-QG-UTP proportions of 80 to 100%.

From these results it is evident that the detection sensitivity improves with increasing proportion of Z-QG introduction. For color development conditions at room temperature, detection of 1 ng/µL of the target nucleic acid was successful when the proportion of Z-QG-UTP was 60% or greater. Further, when the temperature during color development approached the optimum temperature for the new enzyme (alkaline phosphatase: PfuAP), Z-QG-UTP proportions of 80% or greater yielded detection sensitivity levels similar to those of the detection limit for the commercially available Alkphos Direct (100 pg/µL), and high-contrast images were obtainable.

Example 2

Evaluation of Detection Sensitivity by Dot Blots in Accordance with ISH Protocol

[Preparation and Functional Evaluation of PfuAP-Multilabeled RNA Probe]

Sonic hedgehog gene (shh), for which the gene expression pattern within cellular tissue is known, was used as the target mRNA. First, PCR was used to obtain a shh-coding DNA fragment (approximately 1,000 bp). Primer design was conducted so that a T3 promoter was introduced upstream of the gene and a T7 promoter was introduced downstream. Subsequently, using the obtained PCR product as a substrate, a transcription reaction was performed using T7 polymerase (Table 10). During this reaction, by adding the Z-QG-UTP synthesized in test 1 at a variety of different proportions (0 to 100%) instead of the UTP, Z-QG RNA samples having different rates of introduction were prepared. The resulting Z-QG RNA samples were collected by ethanol precipitation, and evaluated by agarose gel electrophoresis and by using a microchip electrophoresis device (Experion, manufactured by Bio-Rad Laboratories, Inc.).

TABLE 10

In vitro transcription conditions

| Component | Concentration |
| --- | --- |
| 10x Transcription Buffer | 1x Buffer |
| PCR product | 20 ng/uL |
| ATP, CTP, GTP | each 1 mM |
| UTP + Z-QG-UTP | Total 1 mM |
| RNase Inhibitor | 1.0 units/uL |
| T7 RNA polymerase | 1.0 units/uL |

10x Transcription Buffer = 0.4M Tris-HCl (pH 8.0), 60 mM MgCl$_2$, 100 mM dithiothreitol, 20 mM spermidine <Preparation of PfuAP-Multilabeled RNA>

In order to investigate, using genetic engineering methods, whether NK14-PfuAP having an introduced peptide tag containing an MTG-recognizable K (MKHK(GGGS)$_2$GS) at the N-terminal could be bound to Z-QG RNA using MTG, firstly, Z-QG RNA samples prepared using a variety of different proportions of Z-QG-UTP were subjected to heat-denaturation by heating to 99.9° C. followed by rapid cooling. Subsequently, reactions were conducted for 6 hours in a 100 mM Tris-HCl buffer solution (pH 8.0), under conditions including 50 μg/mL of each of the Z-QG RNA samples, 0.4 mg/mL of NK14-PfuAP, 5.0 U/mL of MTG, and 1.0 U/μL of RNase inhibitor. As a control, the same operations were performed without the addition of MTG. The reactions were evaluated by agarose gel electrophoresis.

<Evaluation of Probe Capability by Dot Blots> shh S (the target) was immobilized on a membrane, and detection was tested using the PfuAP-multilabeled nucleic acid probes (shh antisense, AS). First, a dilution series of an unlabeled shh S (prepared using T3 polymerase) (50 ng/μL, 10 ng/μL, 1 ng/μL, 0.1 mg/μL) was prepared, and a 1 μL sample of each solution was spotted onto a membrane, and immobilized in an oven (80° C., 2 hours). Subsequently, the operations listed in Table 11 were performed, and the PfuAP-multilabeled probes were used to perform shh S detection. As a control, a membrane was prepared by immobilizing an shh AS chain in the same manner as above, and detection was also performed using this membrane. The compositions of the various solutions are listed in Table 12.

TABLE 11

Conditions for target detection operations in accordance with ISH protocol

| Operation | Solution | Temp. | Time | Repetitions |
| --- | --- | --- | --- | --- |
| Washing | PBSTx | R.T. | 10 min | 3 |
| Hybridization | Hybridization Buffer | R.T. | 10 min | 2 |
|  | Hybridization Buffer | 60° C. | 60 min | 1 |
|  | 50 ng/mL probe in Hybridization Buffer | 60° C. | 10 hours | 1 |

TABLE 11-continued

Conditions for target detection operations in accordance with ISH protocol

| Operation | Solution | Temp. | Time | Repetitions |
| --- | --- | --- | --- | --- |
| Probe washing | Wash 1 | 60° C. | 20 min | 3 |
|  | Wash 2 | 55° C. | 20 min | 3 |
|  | NTMTx | R.T. | 5 min | 2 |
| AP color development reaction | Staining | R.T. | 2 hours | 1 |

TABLE 12

Composition of various buffers

| Solution | Composition |
| --- | --- |
| PBSTx | PBS + 0.1% Triton X-100 |
| Hybridization | 50% Formamide + 5x SSC (pH 7.0) + 2% Casein + 0.1 Triton X-100 + 0.1% CHAPS + 1 mg/mL torula yeast RNA + 5 mM EDTA + 50 ug/mL Heparin |
| Wash 1 | 50% Formamide + 5x SSC (pH 4.5) + 0.1% Triton X-100 + 0.1% CHAPS |
| Wash 2 | 50% Formamide + 5x SSC (pH 7.0) |
| NTMTx | 100 mM NaCl + 100 mM Tris-HCl (pH 9.5) + 50 mM MgCl$_2$ + 0.1% Triton X-100 |
| Staining | 375 ug/mL NBT + 188 ug/mL BCIP in NTMTx |

<Preparation of Z-QG-Multilabeled RNA>

Figures 9A, 9B:
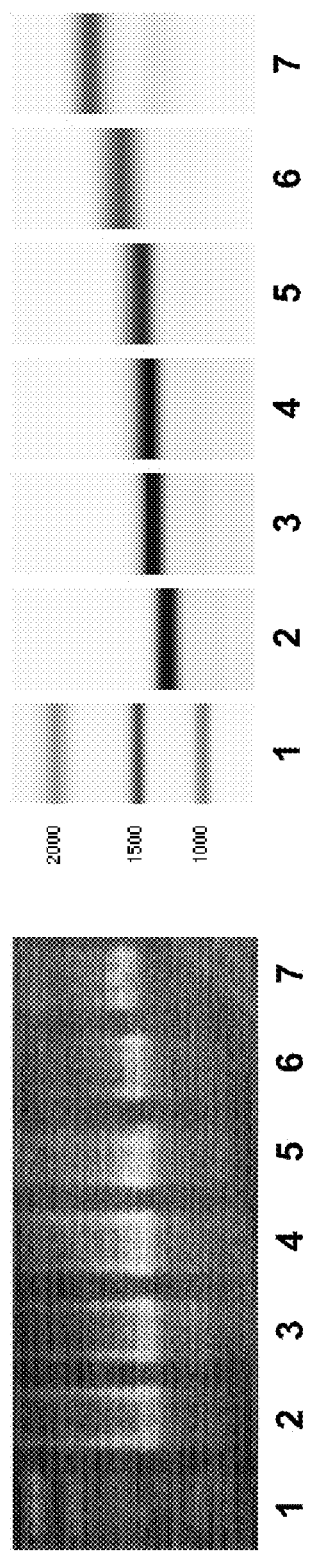
FIG. 9A is a diagram illustrating the results of performing electrophoresis with an agarose gel electrophoresis device, indicating the changes in molecular weight observed when RNA was prepared with varying ratios between UTP and Z-QG-UTP.
FIG. 9B is a diagram illustrating the results of performing electrophoresis with a microchip electrophoresis device, indicating the changes in molecular weight observed when RNA was prepared with varying ratios between UTP and Z-QG-UTP.

The results of preparing RNA with different proportions of UTP and Z-QG-UTP are illustrated in FIG. 9A and FIG. 9B. These results reveal that RNA synthesis was successful under all the different conditions employed, confirming that the synthesized Z-QG-UTP was recognized by the T7 polymerase as a comparatively good substrate. Further, because there is a shift to higher molecular weight with increasing Z-QG-UTP proportion, the amount of Z-QG-UTP introduced into the Z-QG RNA can be adjusted by altering the concentration of the Z-QG-UTP.

<Preparation of PfuAP-Multilabeled Nucleic Acid Probes>

Figure 10:
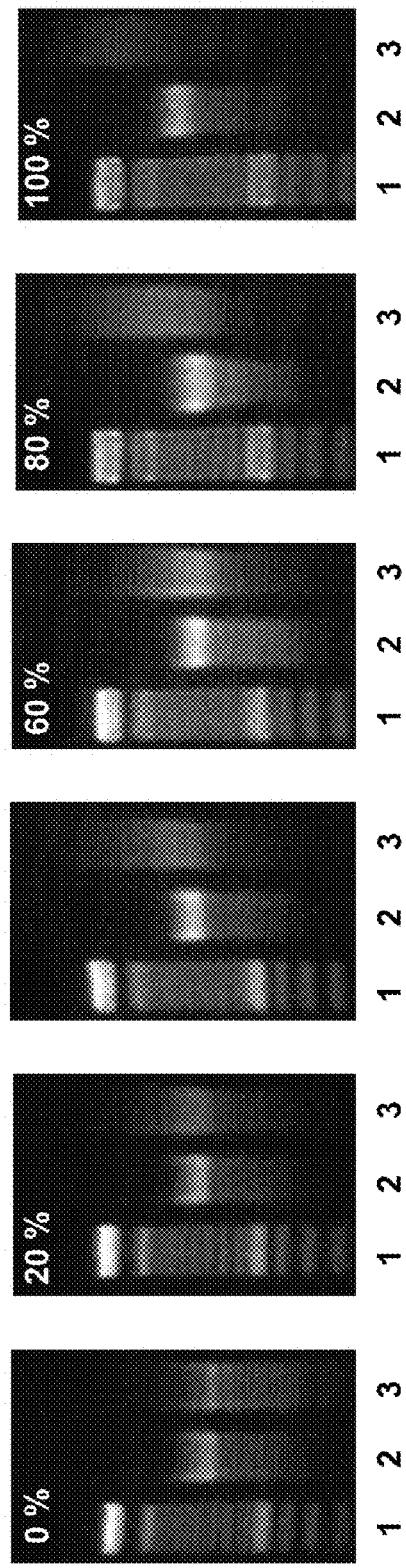
FIG. 10 is a diagram illustrating the results of electrophoresis with an agarose gel electrophoresis device when PfuAP labeling was performed using MTG.

The results of performing PfuAP labeling, using MTG, of Z-QG RNA samples having differing amounts of Z-QG-UTP introduction are illustrated in FIG. 10. Lane 2 illustrates the results when no MTG was added, and lane 3 illustrates the results when MTG was added. Under conditions of 20% to 100%, a shift to higher molecular weight was observed when MTG was added, whereas no such shift was confirmed when Z-QG-UTP was 0%, indicating specific labeling of the introduced Z-QG. Further, the fact that the shift to higher molecular weight increases in size with increasing amounts of introduced Z-QG means that the amount of PfuAP labeling of the probe can be controlled by altering the proportion of Z-QG-UTP.

<Evaluation of Probe Capability by Dot Blots>

Figure 11:
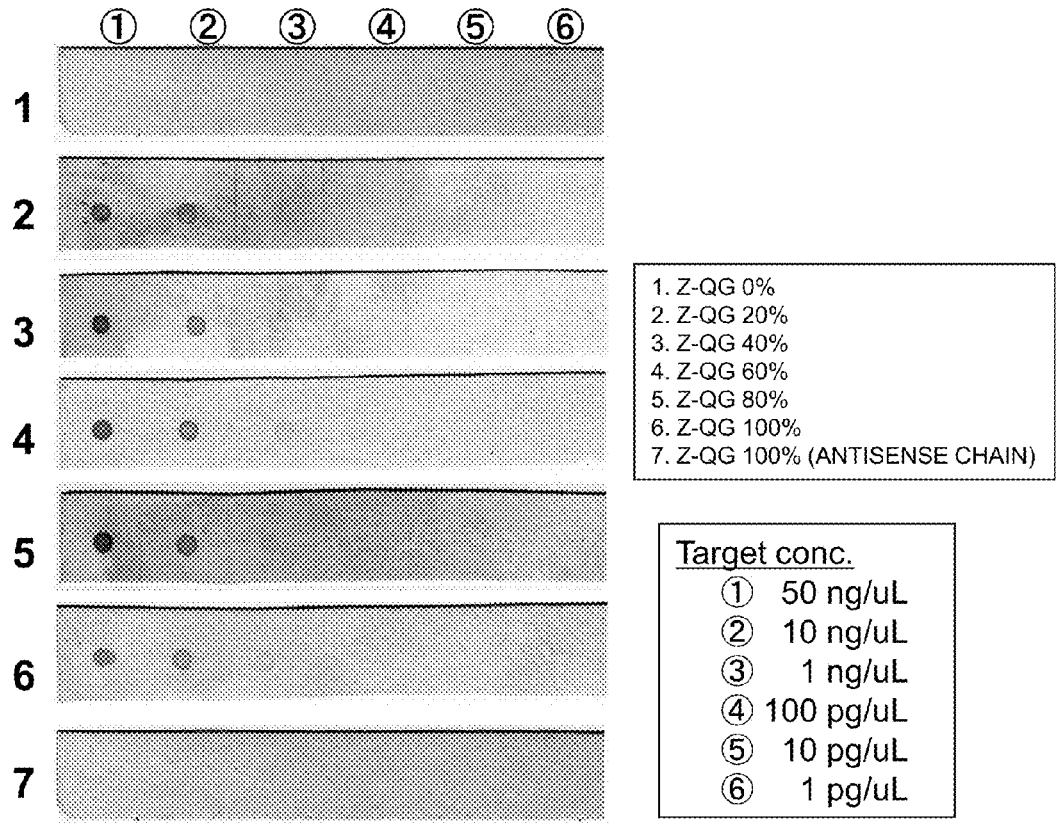
FIG. 11 is a diagram illustrating the results of dot blots at room temperature using the nucleic acid probe of a PfuAP-multilabeled RNA probe.

Dot blots were performed to investigate the functionality of the prepared PfuAP-multilabeled RNA probes as nucleic acid probes (FIG. 11). No spots were confirmed when the AS (antisense) chain was immobilized on the membrane, confirming that a base sequence-specific detection was being achieved. For the probes containing 20 to 100% introduction, detection of the sense chain at 1 ng/μL was possible. These results indicate that by altering the Z-QG-UTP concentration during the transcription reaction, the amount of introduced Z-QG within the resulting modified RNA, and the amount of PfuAP labeling subsequently achieved using MTG can both be controlled. Unlike example 1, no improvement in detection sensitivity was confirmed with increasing amounts of Z-QG introduction. One possible reason for this observation is that, as illustrated above in Tables 11 and 12, the hybridization conditions and washing conditions are considerably more stringent than the Alkphos Direct conditions. As illustrated in FIG. 10, in each case the band broadened upon PfuAP labeling, meaning the PfuAP cannot be claimed to have been introduced uniformly. Consequently, it is surmised that probes containing a smaller number of introduced PfuAP labels or an unmodified probe will hybridize more strongly with the target (AS chain), resulting in similar sensitivity levels for all of the probes. Furthermore, the possibility of a deterioration in the probe double strand formability resulting from the introduction of PfuAP may be another reason for the above sensitivity observation.

On the other hand, if the temperature during staining is increased from room temperature to approximately 50° C. to activate the hyperthermophile-derived enzyme PfuAP, then a further improvement in sensitivity may be expected at this stage.

<Evaluation of ISH Detection Sensitivity Using Enzyme-Labeled Nucleic Acid Probe in the Case where Color Development is Performed Under High-Temperature Conditions>

Figure 12:
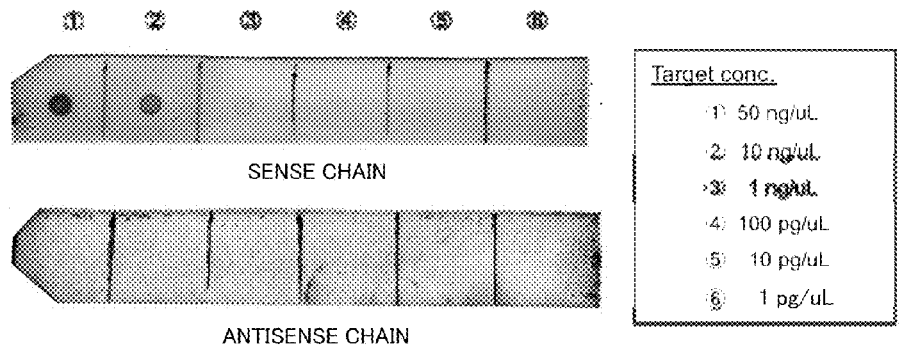
FIG. 12 is a diagram illustrating an evaluation of the detection sensitivity of ISH using an enzyme-multilabeled nucleic acid probe prepared using an Alkphos Direct kit.
Figure 13:
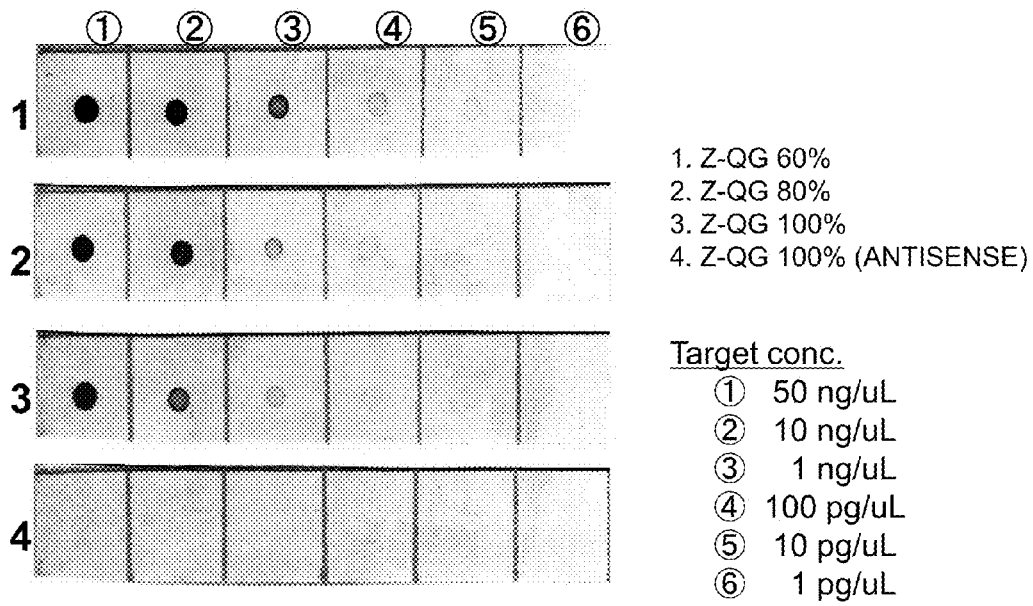
FIG. 13 is a diagram illustrating the results of dot blots at 50° C. using the nucleic acid probe of a PfuAP-multilabeled RNA probe.

The PfuAP used for labeling a nucleic acid probe in the present invention exhibits higher catalytic activity under high-temperature conditions than at room temperature. Accordingly, the detection sensitivity was evaluated for the case where the reaction temperature under the enzyme color development conditions listed in Table 11 was raised from room temperature to 50° C. In order to evaluate the performance as an enzyme-labeled nucleic acid probe, first, the performance of the enzyme-labeled nucleic acid probe obtained with the Alkphos Direct kit and the PfuAP-labeled nucleic acid probe of the present invention were compared for ISH conditions. With the exception of preparing the enzyme-labeled nucleic acid probe using the kit, a dot blot test was performed using the same operations as those described above. The results revealed that detection was possible of the sense chain at 1 ng/μL (FIG. 12). These results indicate that, under ISH conditions, the newly prepared PfuAP multilabeled nucleic acid probe can be used as a probe that exhibits similar detection sensitivity to a probe prepared using a commercially available Alkphos Direct kit. The temperature during the step of performing final detection of the nucleic acid, namely the color development reaction of the enzyme (alkaline phosphatase) region, was room temperature. However, the PfuAP used for labeling the nucleic acid probe of the present invention exhibits higher catalytic activity under high-temperature conditions than at room temperature. Accordingly, the detection sensitivity was evaluated for the case where the reaction temperature for the enzyme color development conditions listed in Table 10 was raised from room temperature to 50° C. As illustrated in FIG. 13, the results revealed that the detection limit varied depending on the proportion of Z-QG introduction, with detection of the nucleic acid possible at 100 pg/μL to 1 ng/μL for Z-QG proportions of 80% or 100%, and at 10 pg/μL at a Z-QG proportion of 60%, and it was clear that an improvement in the detection sensitivity of at least approximately two orders of magnitude was possible compared with the case where the Alkphos Direct probe of the above test 1 was used (1 ng/μL).

In the above examples, testing was conducted using samples for which the concentration had been determined in the manner described below.

[Calculation of Z-QG-UTP Concentration]
<Calculation of Aminoallyl-UTP Absorption Coefficient (@290 nm)>

Figure 14:
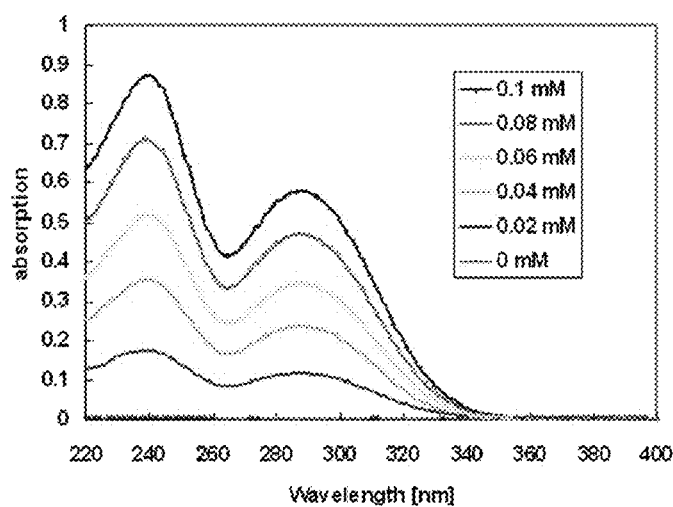
FIG. 14 is a diagram illustrating the results of measuring absorption spectra relative to aminoallyl-UTP concentration in an aminoallyl-UTP in TE buffer (pH 8.0).
Figure 15:
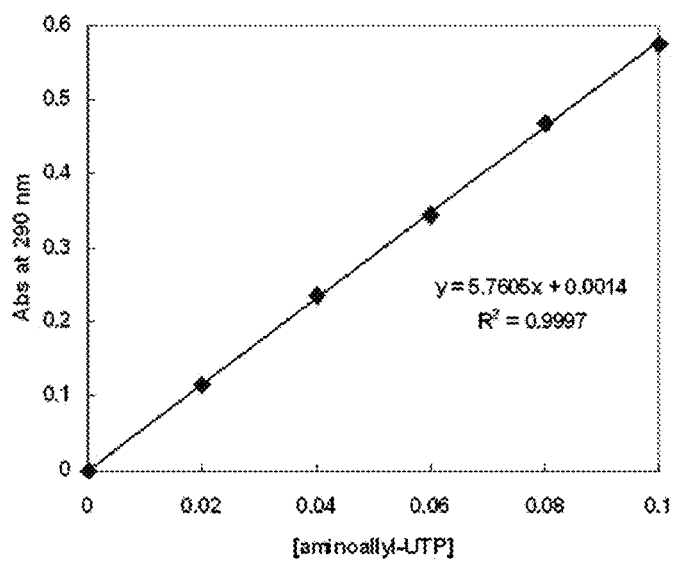
FIG. 15 is a diagram illustrating a calibration curve calculated from the absorbance at 290 nm within the spectra.

Aminoallyl-UTP was dissolved in TE Buffer (pH 8.0), samples were then prepared having concentrations of 0, 0.02, 0.04, 0.06, 0.08 and 0.1 mM, and absorption spectral measurements were then conducted (FIG. 14). The absorbance values at 290 nm were calculated from the spectra and used to create a calibration curve (FIG. 15). In the spectra of FIG. 14, the spectral chart having the highest absorption sensitivity was 0.1 mM, with the absorption sensitivity decreasing thereafter in order from 0.08 mM to 0.06 mM, 0.04 mM, 0.02 mM and 0 mM.

The absorption coefficient at 290 nm is calculated from FIG. 15 ($\epsilon_{290}$=5760 $M^{-1}$ $cm^{-1}$), and taking into consideration the fact that the purity of the commercially available aminoallyl-UTP (manufactured by Sigma-Aldrich Co., Ltd.) was 84% yields a value of $\epsilon_{290}$=6860 $M^{-1}$ $cm^{-1}$. Moreover, because absorption by Z-QG at 290 nm is substantially non-existent, even if unreacted Z-QG remains within the Z-QG-UTP sample, the effect on the concentration determination can be ignored.

<Preparation of Z-QG-UTP Stock Sample>

Following purification by HPLC, the solvent was removed by freeze drying, and the sample was then dissolved in sterilized water (2 mL). Subsequently, a Speed vac was used to concentrate the sample (at this point, a precipitate was observed, and is thought to be due to precipitation of unreacted Z-QG. A spectrum of the same shape as that for aminoallyl-UTP increased with increasing concentration, and therefore it was assumed that the precipitate was not Z-QG-UTP). Following concentration, the supernatant was collected, and following dilution 10-fold with TE buffer, the absorbance was measured using a Nano prop device (light path length: 1 mm) and yielded a result of absorbance ABS=1.061. Accordingly, the Z-QG-UTP concentration C prior to dilution is calculated from the following formula.

$$1.061 = 6860\ [M^{-1}\ cm^{-1}] \times 0.1\ [cm] \times C/10 \quad \text{(Numerical formula 1)}$$

Thus C=approximately 15.5 [mM]

Example 3

Preparation of PfuAP-Multilabeled DNA Probe Using Z-QG DNA and Evaluation of Detection Sensitivity Using Dot Blots A PfuAP-multilabeled DNA probe was prepared using Z-QG DNA, and the probe was evaluated for detection sensitivity by dot blots.

<Synthesis and Purification of Z-QG-dUTP>

Figure 17:
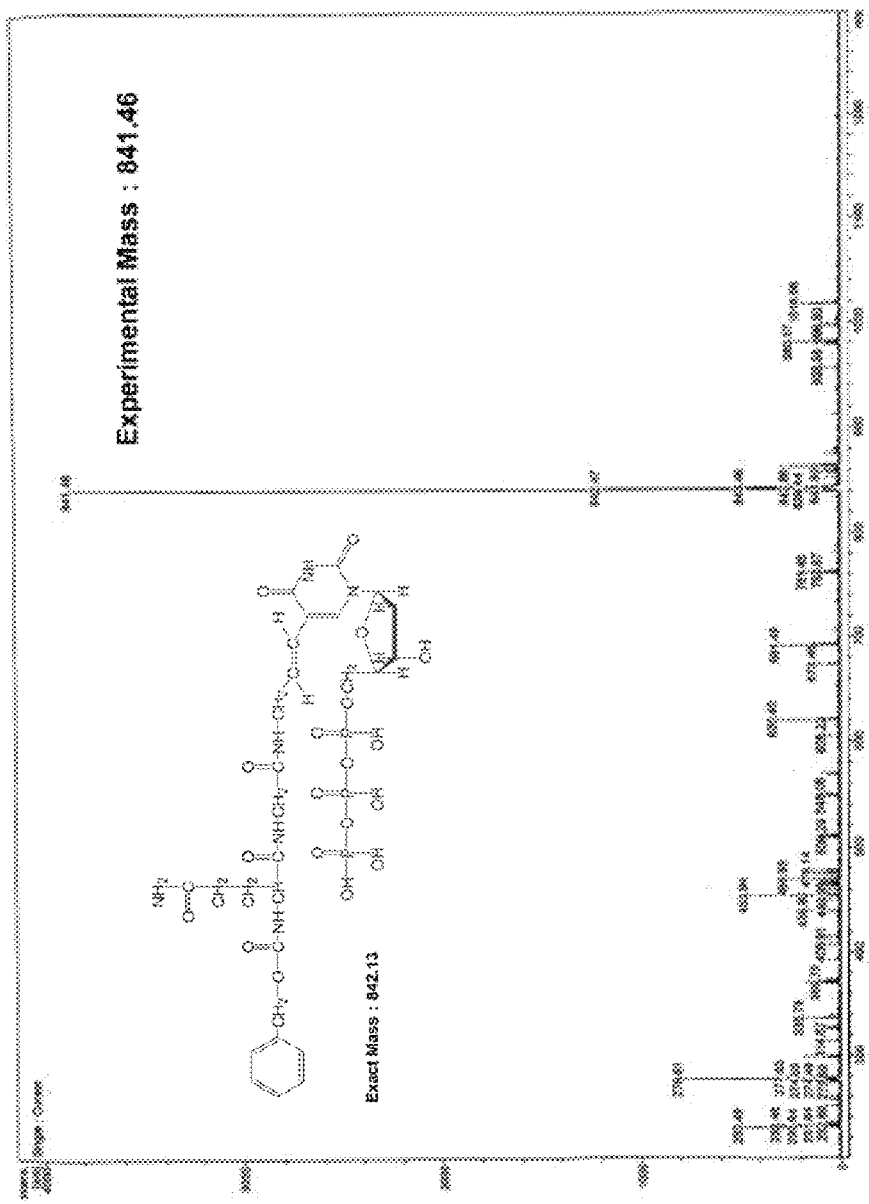
FIG. 17 is a diagram illustrating the results of performing a MALDI TOF-MS analysis of the Z-QG-dUTP synthesized in example 3 of the present invention.

First, 100 mM of N,N'-diisopropylcarbodiimide (DIC), 100 mM of N-hydroxysuccinimide (NHS) and 50 mM of Z-QG were reacted for 20 hours at room temperature (approximately 18 to 22° C. on the day of preparation) in 4 mL of N,N-dimethylformamide (DMF), thus yielding NHS-modified Z-QG (50 mM). Meanwhile, 16 μL of a 10 mM Tris-HCl (pH 7.5) solution (manufactured by Ambion, Inc.) containing 50 mM of 5-(3-aminoallyl)-dUTP (hereinafter abbreviated as "aminoallyl-dUTP", manufactured by Sigma-Aldrich Co., Ltd.), 40 μL of a boric acid buffer solution (pH 8.8) and 16 μL of sterilized water were mixed, preparing 80 μL of a 10 mM aminoallyl-dUTP solution. To this solution was added 80 μL of the NHS-modified Z-QG solution prepared above, and the resulting mixture was reacted overnight at 25° C. Following completion of the reaction, a sample was diluted 10-fold with Milli-Q, and purification was performed by HPLC (manufactured by JASCO Corporation, high-performance liquid chromatograph and pump: TRI ROTAR-V series, variable loop injector: model VL-613, ultraviolet-visible spectroscopic detector: model UVIDEC-100-IV) under the conditions listed in Table 13. Identification of the product was performed using a MALDI TOF-MS apparatus (Autoflex III, manufactured by Bruker Daltonics Corporation). The result is shown in FIG. 17. For this identification, 3-hydroxypicolinic acid (3-HPA) was used as a matrix.

TABLE 13

| HPLC measurement conditions | |
|---|---|
| Column | Inertsil ODS-3 (10 mm × 250 mm) |
| Solvent | A = 100 mM TEAA (pH 7.0), B = acetonitrile |
| Gradient | A = 98% → 88% (5 min) |
| | A = 88% → 73% (30 min) |
| | A = 73% → 63% (10 min) |
| | A = 63% → 98% (5 min) |
| Flow rate | 5.0 mL/min |
| Detection wavelength | 260 nm |

Figure 18:
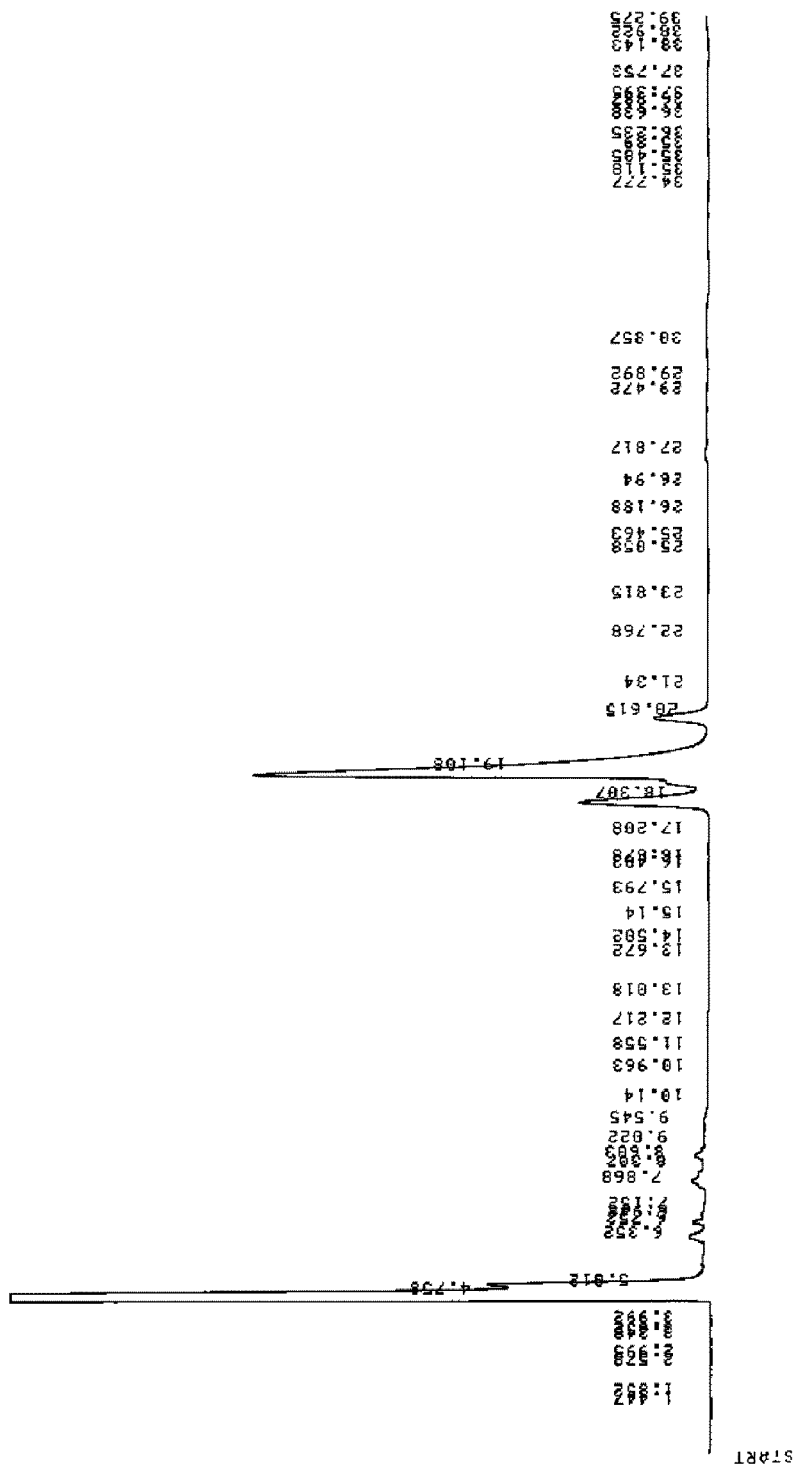
FIG. 18 is a diagram illustrating the results of performing reverse phase HPLC (under the HPLC measurement conditions listed in Table 13) following the synthesis of Z-QG-dUTP in example 3 of the present invention.
Figure 19:
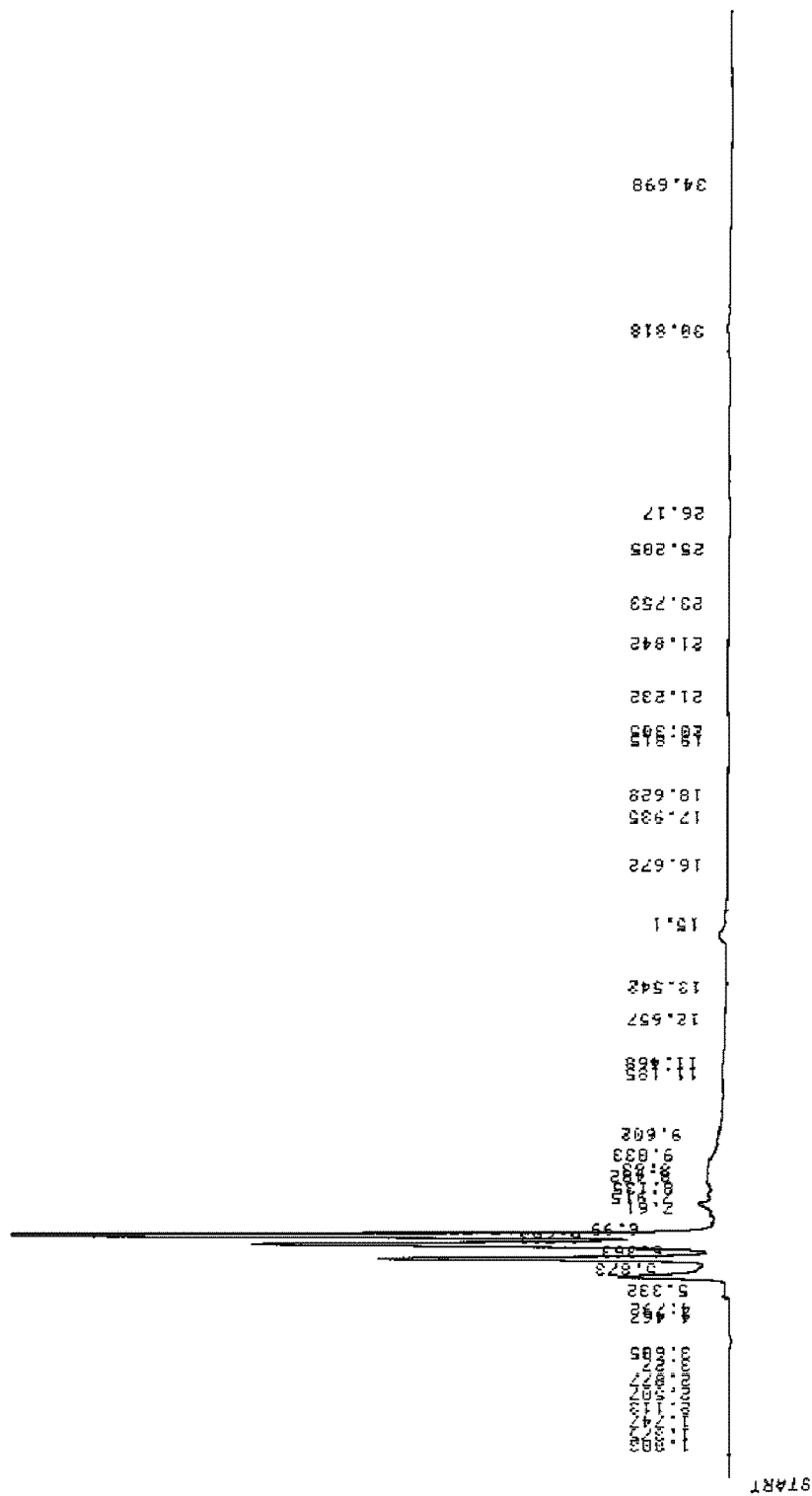
FIG. 19 is a diagram illustrating the results of performing reverse phase HPLC (under the HPLC measurement conditions listed in Table 13) of aminoallyl-dUTP in example 3 of the present invention.

The results of performing reverse phase HPLC following synthesis of the Z-QG-dUTP are illustrated in FIG. 18. Compared with the results obtained for aminoallyl-dUTP (see FIG. 19), a new peak appeared at the hydrophobic side, and it was assumed that this peak represented the Z-QG-dUTP. The peak at a retention time of 19.1 minutes was collected and analyzed by MALDI TOF-MS. As a result, as illustrated in FIG. 17, a peak was confirmed at 841.46, which represents a good match with the theoretical molecular weight of 842.13 and therefore indicates the synthesis of Z-QG-dUTP.

<Preparation of Z-QG DNA by PCR>

First, a primer (Table 14, sequence numbers: 28, 29) was designed for PCR amplification of approximately 300 bp (sequence number: 27) within the gene that codes mouse-derived sonic hedgehog (SHH). Using a plasmid DNA containing the entire sequence (approximately 990 bp) of the gene for coding mouse-derived Shh as the PCR template, a reaction solution was prepared using KOD-Fx (manufactured by Toyobo Co., Ltd.) as the DNA polymerase (Table 15 and Table 16). The PCR conditions comprised one cycle of 94° C.×2 minutes, and 30 cycles of 94° C.×20 seconds, 52° C.×20 seconds and 72° C.×15 seconds. Following PCR, the amplified fragment was confirmed by agarose electrophoresis. The obtained amplified fragment was purified using a MinElute PCR Purification kit (manufactured by Qiagen), and the Z-QG DNA concentration was measured using a Nano Drop device.

TABLE 14

| Shh 300 by fragment primer sequence | |
|---|---|
| | Primer sequence |
| Shh300 Primer-1 | 5'-AGGAAAACACGGGAGCAGAC-3' |
| Shh300 Primer-2 | 5'-TCTCTGCTTTCACAGAACAG-3' |

TABLE 15

| PCR reaction solution composition | | |
|---|---|---|
| Composition | Amount added | Final concentration |
| 12 ng/μL plasmid DNA | 8 μL | 24 ng |
| 10 μM Shh300 Primer-1 | 3 μL | 0.3 μM |
| 10 μM Shh300 Primer-2 | 3 μL | 0.3 μM |
| KOD-Fx | 2 μL | 2 Unit |
| 1.5 mM dATP, dCTP, dGTP | 10 μL | 0.15 mM |
| 1.5 mM dTTP + Z-QG-dUTP (Table 3) | 10 μL | 0.15 mM |
| 2x Buffer | 50 μL | 1x |
| Water | 24 μL | |
| Total | 100 μL | |

TABLE 16

| | Z-QG-dUTP 0% | Z-QG-dUTP 50% | Z-QG-dUTP 100% |
|---|---|---|---|
| dTTP | 1.5 mM | 0.75 mM | — |
| Z-QG-dUTP | — | 0.75 mM | 1.5 mM |

Figure 20:
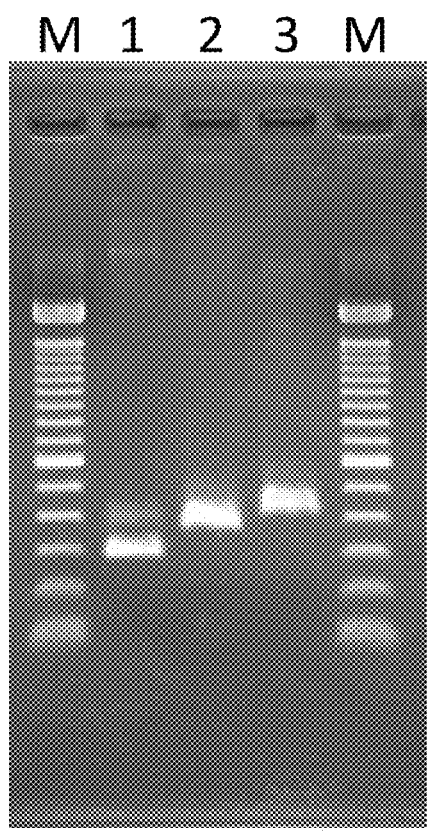
FIG. 20 is a diagram illustrating the results of performing electrophoresis when PCR was performed for various proportions of Z-QG-dUTP during the preparation of Z-QG DNA in example 3 of the present invention.

The electrophoresis results when PCR was performed for various Z-QG-dUTP proportions are illustrated in FIG. 20. The fact that a band was confirmed for the amplified fragment even when PCR was performed with the proportion of the Z-QG-dUTP set to 50% or 100% indicates that the Z-QG-dUTP is recognized as a DNA polymerase substrate. Furthermore, from the fact that the band shifts to a higher molecular weight as the proportion of the Z-QG-dUTP is increased, it was clear that the amount of Z-QG introduced could be adjusted by altering the amount of the Z-QG-dUTP during PCR. When a Nano prop device was used to measure the Z-QG DNA concentration levels within each of the purified samples, the results revealed a concentration of 73.8 ng/μL for the Z-QG DNA prepared with 0% Z-QG-dUTP, a concentration of 111.6 ng/μL for the Z-QG DNA prepared with 50% Z-QG-dUTP, and a concentration of 59.1 ng/μL for the Z-QG DNA prepared with 100% Z-QG-dUTP <Investigation of PfuAP Labeling of Z-QG DNA>

An investigation of whether genetic engineering could be used to bind NK14-PfuAP having an introduced peptide tag containing an MTG-recognizable lysine residue (K) to Z-QG DNA using MTG was conducted by using Z-QG DNA samples having various amounts of introduced Z-QG. First, 15 ng/μL of each of the various Z-QG DNA samples was reacted for 6 hours at 4° C. with 0.4 mg/mL of NK14-PfuAP and 5.0 Unit/mL of MTG in a Tris-HCl buffer solution (pH 8.0). The case in which no MTG was added was also investigated. Confirmation of the PfuAP labeling was performed by agarose electrophoresis.

Figure 21:
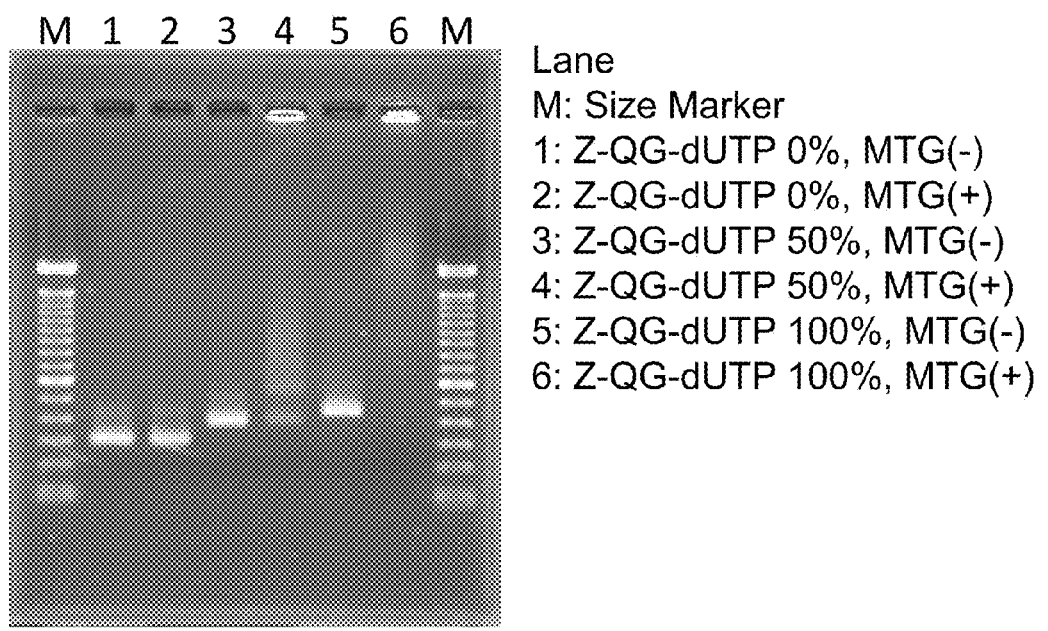
FIG. 21 is a diagram illustrating the results of performing agarose electrophoresis following reaction with MTG, during the investigation of PfuAP labeling of Z-QG DNA in example 3 of the present invention.

The results of agarose electrophoresis following the MTG reaction are illustrated in FIG. 21. When Z-QG DNA that was prepared under conditions of 50% or 100% of Z-QG-dUTP was used, a shift to higher molecular weight was observed upon addition of the MTG, but with the Z-QG-unlabeled DNA (the negative control DNA prepared with 0% of Z-QG-dUTP), no such shift to higher molecular weight was observed. Further, no increase in molecular weight was observed when no MTG was added to the Z-QG DNA. From these results it was clear that, in the presence of MTG, the NK14-PfuAP was binding specifically to the Z-QG region of the Z-QG DNA. Further, the fact that the shift to a higher molecular weight was more definite when the Z-QG DNA was prepared under conditions of 100% of Z-QG-dUTP rather than 50% of Z-QG-dUTP indicated that the amount of bound PfuAP can be adjusted by altering the proportion of Z-QG-dUTP used during the PCR amplification.

<Preparation of PfuAP-Multilabeled DNA Probes>

Z-QG DNA samples prepared under conditions of 50% or 100% of Z-QG-dUTP and NK14-PfuAP were bound using MTG to prepare PfuAP-multilabeled DNA probes. First, each Z-QG DNA was subjected to heat treatment for 5 minutes at 90° C. to convert the DNA to a single strand, and a reaction was then conducted for 6 hours at 4° C. in a 100 mM Tris-HCl buffer solution (pH 8.0), under conditions including 25 ng/μL of the Z-QG DNA, 0.4 mg/mL of NK14-PfuAP, and 5.0 Unit/mL of MTG (yielding a probe in which heat treatment was performed prior to MTG reaction). Converting the DNA to a single strand by heat treatment has a large effect on the detection capability of the probe, and therefore a probe was also prepared using a Z-QG DNA that had not been subjected to heat treatment, by performing PfuAP labeling under the same conditions and subsequently performing a heat treatment for 5 minutes at 90° C. (yielding a probe in which heat treatment was performed following MTG reaction). The PfuAP labeling of the DNA probes was confirmed by agarose electrophoresis.

Figure 22:
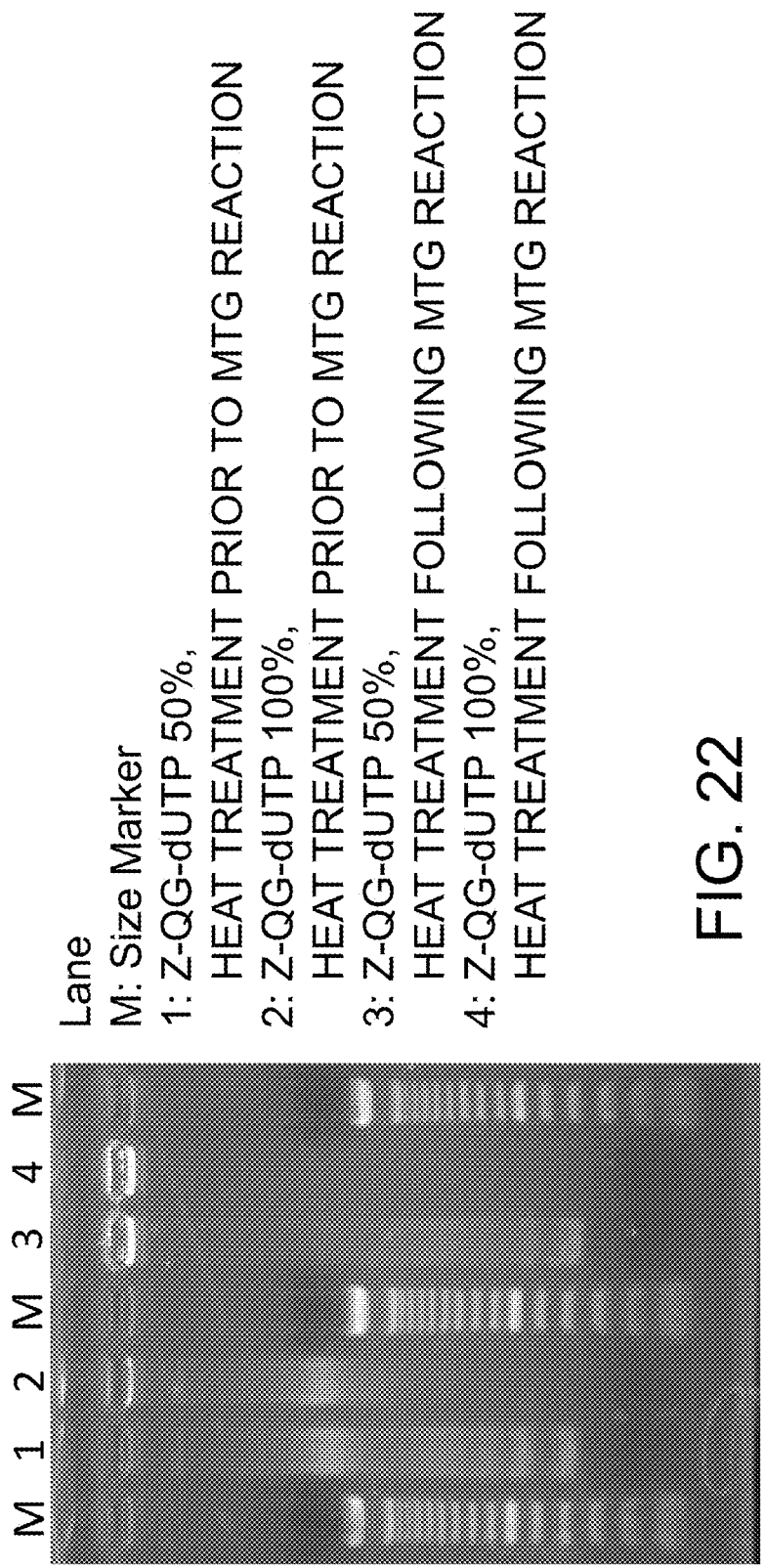
FIG. 22 is a diagram illustrating the results of performing agarose electrophoresis following reaction with MTG, for the preparation of a PfuAP-multilabeled DNA probe of example 3 of the present invention.

The results of the agarose electrophoresis following the MTG reaction are illustrated in FIG. 22. The fact that the Z-QG DNA subjected to heat treatment prior to the MTG reaction and the Z-QG DNA subjected to heat treatment following the MTG reaction both exhibited a shift to higher molecular weight confirmed PfuAP labeling of the Z-QG DNA.

<Evaluation of Detection Sensitivity by Dot Blots>

Evaluation of the detection sensitivity of each of the prepared PfuAP-multilabeled probes was performed by dot blots. The various compositions and the protocol used during hybridization were in accordance with those of the commercially available detection kit Alkphos Direct (manufactured by GE Healthcare Bioscience Bioprocess Corporation). A 990 bp Shh DNA fragment containing the probe sequence (sequence number: 30, see Table 17 for the primer sequence (sequence number: 31)) and a 300 bp Shh DNA fragment having the same sequence as the probe were used as the target DNA. Further, an approximately 1.7 kb DNA fragment of a PfuAP encoding gene (sequence number: 32, see Table 18 for the primer sequences (sequence numbers: 33, 34)) was used as a negative control.

TABLE 17

| | Primer sequence |
|---|---|
| T7 promoter primer | 5'-TAATACGACTCACTATAGGGAGGTGC CAATGTGGTAGAGC-3' |

TABLE 18

| | Primer sequence |
|---|---|
| PfuAP Primer-1 | 5'-TAA TAC GAC TCA CTA TAG GG-3' |
| PfuAP Primer-2 | 5'-TGC TAG TTA TTG CTC AGC GG-3' |

Each of the target DNA samples was diluted to concentrations of 50 ng/μL and 50 pg/μL using TE buffer (the negative control was only diluted to 50 ng/μL), and 1 μL of each solution was spotted onto a positively charged membrane (Hybond N+, manufactured by GE Healthcare Bioscience Bioprocess Corporation) and then subjected to heat treatment for 2 hours at 80° C., thereby immobilizing the DNA on the membrane. Subsequently, the membrane was transferred to the hybridization buffer appended to the detection kit, and a pre-hybridization was performed for 30 minutes at 55° C. Each of the PfuAP-multilabeled DNA probes prepared using the method described above was then added to the hybridization buffer in sufficient amount to achieve a concentration of 50 ng/mL, and hybridization was conducted overnight (approximately 14 to 16 hours) at 55° C.

Following hybridization, the membrane was transferred to a Wash I buffer (Table 19) and was washed by shaking for 15 minutes at 55° C. This operation was performed twice. Subsequently, the membrane was washed in a Wash II buffer (Table 20) for 5 minutes at room temperature (approximately 18 to 22° C. on the day of testing). This operation was also performed twice.

TABLE 19

| Component | Final concentration |
|---|---|
| Urea | 2M |
| SDS | 0.1% |
| Na phosphate (pH 7.0) | 50 mM |
| NaCl | 150 mM |
| MgCl$_2$ | 1 mM |
| Blocking reagent | 0.2% |

TABLE 20

| Component | Final concentration |
|---|---|
| Tris base | 50 mM |
| NaCl | 100 mM |
| MgCl$_2$ | 2 mM |

The membrane was washed for 5 minutes at room temperature in a NTMTx buffer (Table 21), and then transferred to a staining solution (375 μg/mL NBT+188 μg/mL BCIP in NTMTx), and color development was performed by standing for two hours at 50° C. under blackout conditions.

TABLE 21

| Component | Final concentration |
|---|---|
| Tris-HCl (pH 9.5) | 100 mM |
| NaCl | 100 mM |
| MgCl$_2$ | 50 mM |
| Triton X-100 | 0.1% |

The results of dot blots using each of the PfuAP-labeled DNA probes are illustrated in FIG. 23. Dot signals were detected regardless of which DNA probe was used, indicating that DNA probes prepared by labeling Z-QG DNA with PfuAP using MTG exhibit detection capabilities as nucleic acid probes. It was also evident that the probes prepared by performing heat treatment of the Z-QG DNA prior to the MTG reaction (the probes in which heat treatment was performed prior to MTG reaction) exhibited improved detection sensitivity compared with the probes prepared by performing heat treatment following the MTG reaction (the probes in which heat treatment was performed following MTG reaction). It is thought that the reasons for this observation may include the fact that in the probes in which heat treatment was performed following MTG reaction, because the PfuAP-labeled DNA probe was subjected to heat treatment, the increase in reaction volume during the heat treatment may have resulted in an inadequate heat treatment, meaning the DNA may not have undergone complete heat denaturation, and the fact that heat treatment of the labeled probe may have caused deactivation of the PfuAP.

The probes in which heat treatment was performed prior to MTG reaction were able to detect dots down to a concentration of 50 pg/μL for both the probe containing 50% of introduced Z-QG and the probe containing 100% of introduced Z-QG. In the negative control in which the target nucleic acid concentration was a high value of 50 ng/μL, a faint non-specific signal was detected, but complementary DNA was able to be distinguished clearly. Further, the difference in chain length of the target DNA had no significant effect on the detection sensitivity.

Example 4

RNA Detection in Accordance with ISH Protocol by PfuAP-Multilabeled DNA Probes Using Z-QG DNA In example 3, the detection target nucleic acid was DNA. In this example 4, the functionality of PfuAP-multilabeled DNA probes as nucleic acid probes was evaluated for the case where the detection target nucleic acid was RNA.

<Preparation of Z-QG DNA by PCR>

Preparation of Z-Qg DNA by PCR was performed in the same manner as that described for example 3.

<Preparation of PfuAP-Multilabeled DNA Probes>

Z-QG DNA samples prepared under conditions of 50% or 100% of Z-QG-dUTP and NK14-PfuAP were bound using MTG to prepare PfuAP-multilabeled DNA probes. First, each Z-QG DNA was subjected to heat treatment for 5 minutes at 90° C. to convert the DNA to a single strand, and a reaction was then conducted for 6 hours at 4° C. in a 100 mM Tris-HCl buffer solution (pH 8.0), under conditions including 25 ng/μL of the Z-QG DNA, 0.4 mg/mL of NK14-PfuAP, and 5.0 Unit/mL of MTG. The PfuAP labeling of the DNA probes was confirmed by agarose electrophoresis.

Figure 24:
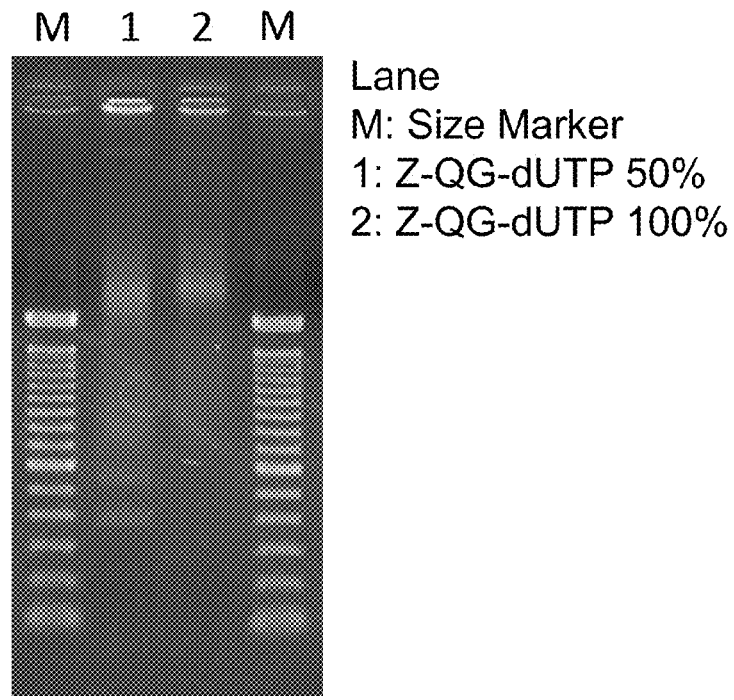
FIG. 24 is a diagram illustrating the results of performing agarose electrophoresis following reaction with MTG, for the preparation of a PfuAP-multilabeled DNA probe of example 4 of the present invention.

The results of the agarose electrophoresis following the MTG reaction are illustrated in FIG. 24. For both the Z-QG DNA containing 50% introduced Z-QG-dUTP and the Z-QG DNA containing 100% introduced Z-QG-dUTP, the band shifted to a higher molecular weight following the MTG reaction. These results confirmed PfuAP labeling of the Z-QG DNA, and therefore the labeled Z-QG DNA samples were used as DNA probes for dot blots.

<Evaluation of Detection Sensitivity by Dot Blots in Accordance with ISH Protocol>

An Shh DNA fragment of 990 bp containing the probe sequence was obtained by PCR (sequence number: 30). Primer design was performed so that a T7 promoter was incorporated downstream of the Shh gene (sequence number: 31, see Table 17). Subsequently, using the obtained PCR product as a substrate, a transcription reaction was conducted using T7 polymerase (Table 22). Following the transcription reaction, unreacted NTP and the like were removed by purification using a gel permeation column (Mini Quick Spin Column, manufactured by Roche Ltd.), and the purified product was used as the target RNA.

TABLE 22

| Composition | Amount added | Final concentration |
|---|---|---|
| Template DNA (200 ng/μL) | 2 uL | 20 ng/uL |
| T7 Polymerase | 2 uL | 1.0 Units/uL |
| 10 mM NTP Mix | 2 uL | 1 mM |
| 20 U/uL RNase inhibitor | 1 uL | 1.0 Units/uL |
| 10x Transcription Buffer | 2 uL | 1x |
| Sterilized water | 11 uL | |
| Total | 20 uL | |

The obtained target RNA was diluted using TE Buffer to form a 3-stage series of 50 ng/μL, 1 ng/μL and 50 pg/μL, and 1 μL of each solution was spotted onto a positively charged membrane (Hybond N+, manufactured by GE Healthcare Bioscience Bioprocess Corporation) and then subjected to heat treatment for 2 hours at 80° C., thereby immobilizing the RNA on the membrane. As a negative control, a commercially available yeast RNA (Ribonucleic torula yeast RNA, manufactured by Sigma-Aldrich Co., Ltd.) was diluted to 50 ng/μL, and 1 μL of the dilute solution was then spotted onto a membrane and immobilized in the same manner as described above. Subsequently, the membrane was transferred to a hybridization buffer (Table 23), and a pre-hybridization was performed for 30 minutes at 60° C. Each of the DNA probes prepared using the method described above was then added to the hybridization buffer in sufficient amount to achieve a concentration of 50 ng/μL, and hybridization was conducted overnight (approximately 14 to 16 hours) at 60° C.

TABLE 23

| Component | Final concentration |
|---|---|
| Formamide | 50% |
| SSC (pH 7.0) | 5x |
| Casein | 2% |
| Trion X-100 | 0.1% |
| CHAPS | 0.1% |
| Torula yeast RNA | 1 mg/mL |
| EDTA | 5 mM |
| Heparin | 50 ug/mL |

Following hybridization, the membrane was subjected to washing operations. The various washing solutions are listed in Table 24. The membrane was transferred to the Wash I buffer and washed by shaking for 20 minutes at 60° C. This operation was performed three times. Subsequently, the membrane was washed in the Wash II buffer for 20 minutes at 55° C. This operation was also performed three times. Subsequently, the membrane was twice washed for 5 minutes at room temperature (approximately 18 to 22° C. on the day of testing) in the NTMTx buffer, and the washed membrane was then transferred to a staining solution (375 μg/mL NBT+188 μg/mL BCIP in NTMTx), and color development was performed by standing for two hours at 50° C. under blackout conditions.

TABLE 24

| Wash solution | Component | Final concentration |
|---|---|---|
| Wash I | Formamide | 50% |
| | SSC (pH 4.5) | 5x |
| | Triton X-100 | 0.1% |
| | CHAPS | 0.1% |
| Wash II | Formamide | 50% |
| | SSC (pH 7.0) | 5x |
| NTMTx | NaCl | 100 mM |
| | Tris-HCl (pH 9.5) | 100 mM |
| | MgCl$_2$ | 50 mM |
| | Triton X-100 | 0.1% |

Figure 25:
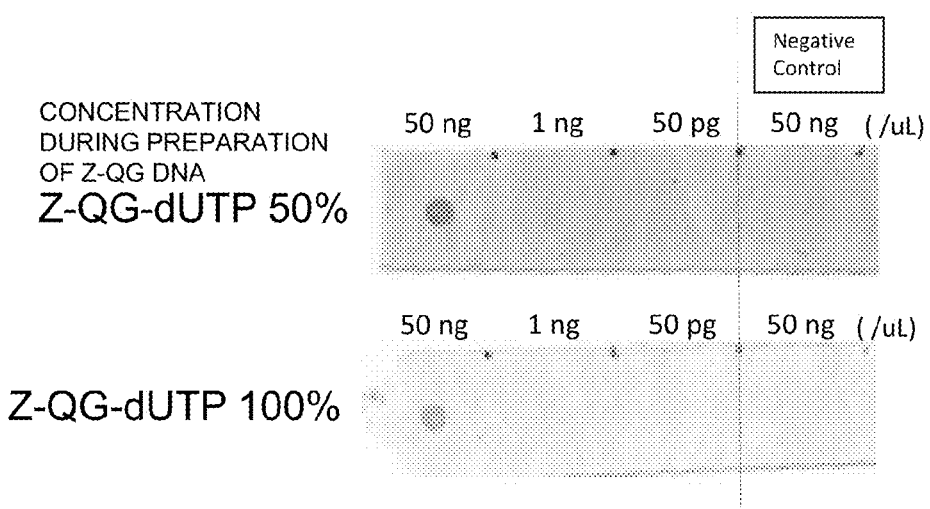
FIG. 25 is a diagram illustrating the results of dot blots for each PfuAP-labeled DNA probe in example 4 of the present invention.

The results of dot blots using each of the PfuAP-labeled DNA probes in accordance with ISH protocol are illustrated in FIG. 25. The DNA probes containing 50% and 100% of introduced Z-QG were both able to detect dots down to a concentration of 1 ng/μL, and the signal color development intensity was substantially the same regardless of which probe was used. In the case of the negative control, no non-specific signal was detected. Based on these results, it was clear that DNA probes prepared by using MTG to label Z-QG DNA with PfuAP were able to be used as probes for detecting RNA.

Example 5

Evaluations of probe capability were also performed for multilabeled nucleic acid probes prepared by performing labeling using an AP (BAP) derived from the mesophile *Escherichia coli* in the same manner as that described for example 2.

<Preparation of BAP-Multilabeled RNA>

An RNA denaturation treatment was performed in the same manner as that described for example 2, and reactions were then conducted for 6 hours in a 100 mM Tris-HCl buffer solution (pH 8.0), under conditions including 50 μg/mL of each of the Z-QG RNA samples, 0.4 mg/mL of NK14-BAP, 5.0 U/mL of MTG, and 1.0 U/μL of RNase inhibitor. As a control, the same operations were performed without the addition of MTG. The reactions were evaluated by agarose gel electrophoresis.

<Evaluation of Probe Capability by Dot Blots>

The capabilities of the probes were evaluated by dot blots in the same manner as that described for example 2.

Figure 26:
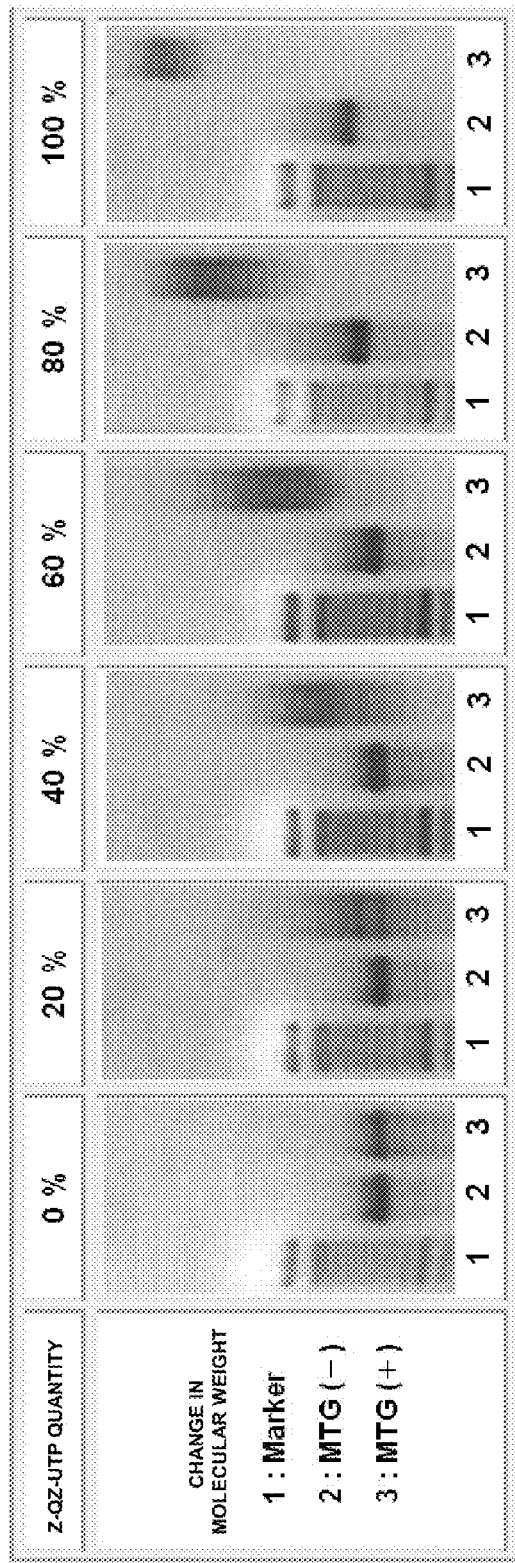
FIG. 26 is a diagram illustrating the results of performing electrophoresis with an agarose gel electrophoresis device when MTG was used to perform BAP labeling in example 5 of the present invention.

The changes in molecular weight upon labeling are illustrated in FIG. 26. The results confirmed that a marked increase in molecular weight had occurred in proportion to the amount of introduced Z-QG. Further, when Z-QG RNA (100%) was used, a narrowing of the molecular weight distribution was confirmed. When only Z-QG-UTP was used during preparation of the RNA, it is thought that because the number and location of the introduced Z-QG were effectively monodisperse (in theory, all of the U sites), labeling proceeded substantially uniformly. The fact that, compared with PfuAP (FIG. 10), a more marked increase in molecular weight was observed was a result that indicated that BAP exhibits a higher level of reactivity with Z-QG RNA.

Figure 27:
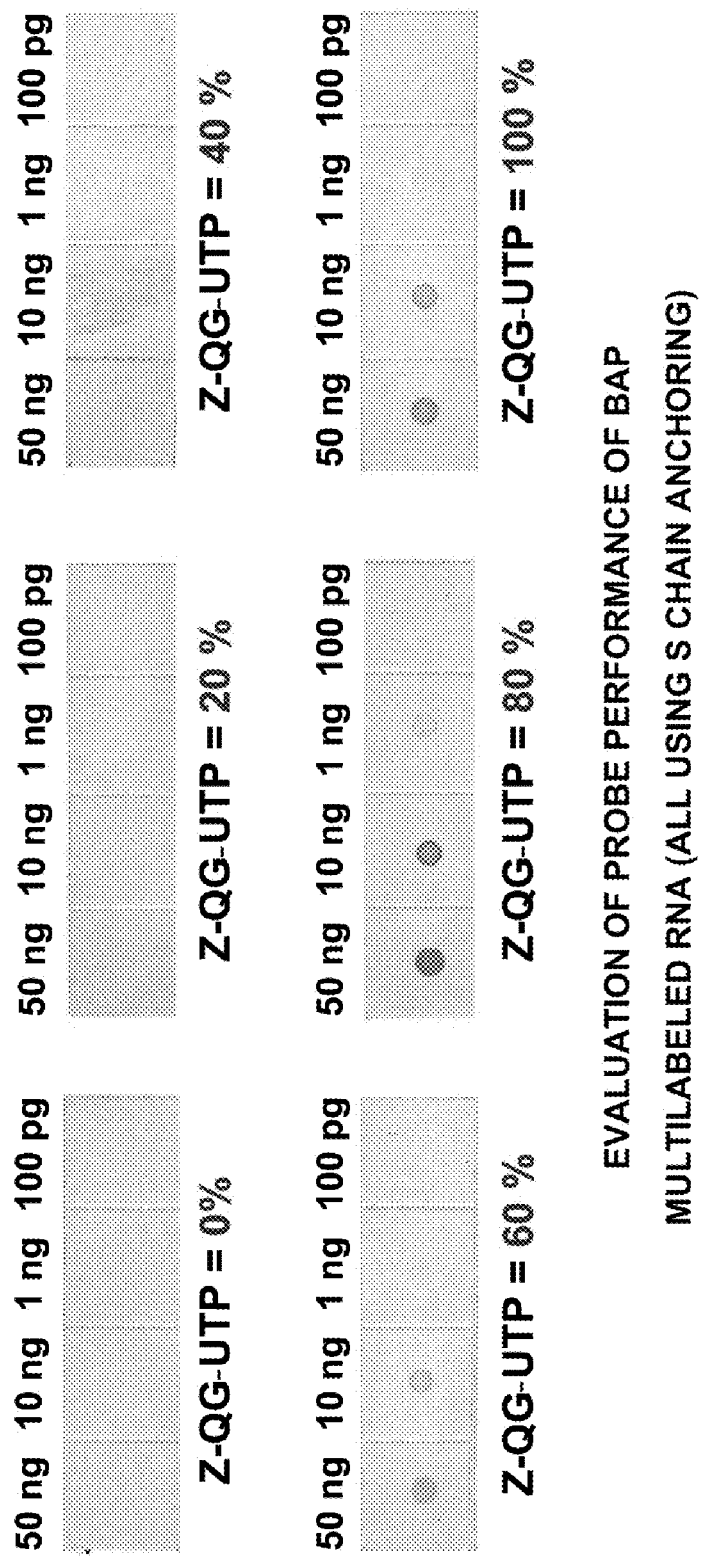
FIG. 27 is a diagram illustrating the results of dot blots at room temperature using the nucleic acid probe of a BAP-multilabeled RNA probe in example 5 of the present invention.

Using the obtained BAP-multilabeled RNA, the probe capabilities were evaluated by dot blots (see FIG. 27). The results revealed that when BAP labeling was performed for mRNA having 60%, 80% or 100% of introduced Z-QG, approximately 1 ng of RNA was detectable. The reason that substantially no detection was observed at 20% and 40% is thought to be due to residual BAP-unmodified RNA (see FIG. 26). Comparison with the probes labeled using PfuAP (detection limit: 10 μg) indicated that PfuAP is more suitable as the labeling enzyme for this system.

Example 6

Fluorescent Dye Labeling of Z-QG RNA Using MTG, and Detection of a Target Nucleic Acid by Dot Blots <Preparation of Alexa Fluor 555-Multilabeled RNA>

An investigation was to conducted as to whether the primary amine-derived Alexa Fluor (a registered trademark) 555 cadaverine (manufactured by Invitrogen Corporation) could be bound, as a fluorescent dye, to Z-QG RNA using MTG. First, Z-QG RNA prepared under conditions including a Z-QG-UTP usage rate of 100% was subjected to a denaturation treatment by heating to 99.0° C. followed by rapid cooling. Subsequently, a reaction was conducted for 6 hours in a 100 mM Tris-HCl buffer solution (pH 8.0), under conditions including 50 μg/mL of the Z-QG RNA, 20 μM of Alexa Fluor 555 cadaverine, 5.0 units/mL of MTG, and 1.0 U/μL of RNase inhibitor. As controls, the same operations were performed without the addition of MTG and for an unmodified RNA with no introduced Z-QG. The reactions were evaluated by agarose gel electrophoresis.

Figure 28:
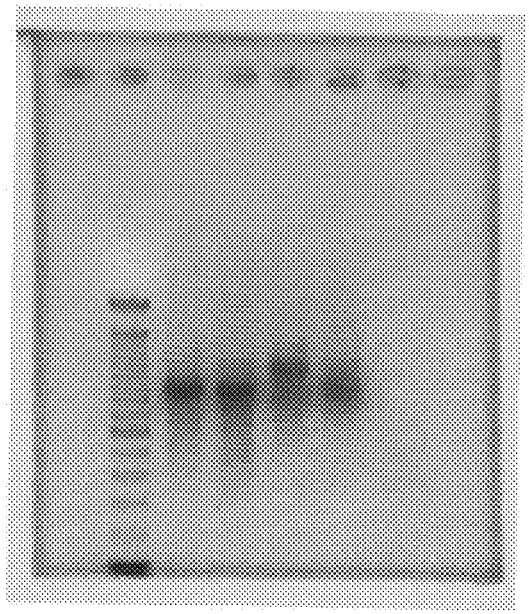
FIG. 28 is a diagram illustrating the results of performing Alexa Fluor 555 cadaverine labeling of Z-QG RNA using MTG in example 6 of the present invention.

The results of labeling the Z-QG RNA with Alexa Fluor 555 cadaverine using MTG are illustrated in FIG. 28. In the figure, lane 2 illustrates the result for unmodified RNA and Alexa Fluor 555 cadaverine, lane 3 illustrates the result for the same conditions as lane 2 with added MTG, lane 4 illustrates the result for Z-QG RNA and Alexa Fluor 555 cadaverine, and lane 5 illustrates the result for the same conditions as lane 4 with added MTG. The signals in lanes 4 and 5 observed at substantially the same location as the unmodified RNA are thought to be derived from unreacted Alexa Fluor 555 cadaverine. This premise is also supported by the fact that a similar band was also confirmed, prior to staining with ethidium bromide, in each of lanes 2 to 4. Whereas no change was observed between lane 2 and lane 3, comparison of lane 4 and lane 5 revealed that when MTG was added, the band derived from Z-QG RNA disappeared, and a shift to lower molecular weight was confirmed. This finding indicates that the negatively charged Alexa Fluor 555 cadaverine had bound to the Z-QG RNA, suggesting the generation of Alexa Fluor 555-multilabeled RNA.

<Evaluation of Probe Capability by Dot Blots> shh S (the target) was immobilized on a membrane, and detection was tested using the Alexa Fluor 555-multilabeled nucleic acid probe. First, a solution of unlabeled shh S with a concentration of 50 ng/μL was prepared, a 1 μL sample of this solution was spotted onto a membrane, and following drying, another 1 μL was added (total: 1,000 ng) and immobilization was performed in an oven (80° C., 2 hours). Subsequently, the operations listed in Table 25 were performed, and detection of the shh S by the Alexa Fluor 555-multilabeled nucleic acid probe was performed using a fluorescent imager (Molecular Imager FX Pro, manufactured by BIO-RAD Laboratories, Inc, 532 nm excitation, 555 nm long pass). As a control, the same operations as those described above were also performed on a membrane on which an shh AS chain had been immobilized in the same manner as above. The compositions of the various solutions are listed in Table 26.

TABLE 25

Dot blot operations when Alexa Fluor 555-multilabeled RNA was used as a probe

| Operation | Solution | Temp. | Time | Repetitions |
| --- | --- | --- | --- | --- |
| Washing | PBSTx | R.T. | 10 min | 3 |
| Hybridization | Hybridization Buffer | R.T. | 10 min | 2 |
|  | Hybridization Buffer | 60° C. | 60 min | 1 |
|  | 500 ng/mL probe in Hybridization Buffer | 60° C. | 10 hours | 1 |
| Probe washing | Wash 1 | 60° C. | 20 min | 3 |
|  | Wash 2 | 55° C. | 20 min | 3 |
|  | NTMTx | R.T. | 5 min | 2 |

TABLE 26

Composition of various buffers used

| Solution | Composition |
| --- | --- |
| PBSTx | PBS + 0.1% Triton X-100 |
| Hybridization | 50% Formamide + 5x SSC (pH 7.0) + 2% Casein + 0.1 Triton X-100 + 0.1% CHAPS + 1 mg/mL torula yeast RNA + 5 mM EDTA + 50 ug/mL Heparin |
| Wash 1 | 50% Formamide + 5x SSC (pH 4.5) + 0.1% Triton X-100 + 0.1% CHAPS |
| Wash 2 | 50% Formamide + 5x SSC (pH 7.0) |
| NTMTx | 100 mM NaCl + 100 mM Tris-HCl (pH 9.5) + 50 mM $MgCl_2$ + 0.1% Triton X-100 |

Figure 29:
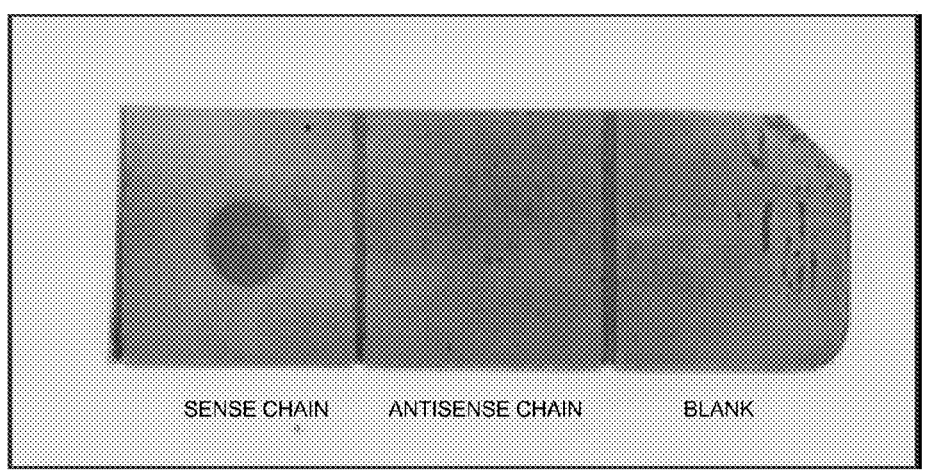
FIG. 29 is a diagram illustrating the results of dot blots at room temperature using the nucleic acid probe of an Alex Fluor 555-multilabeled RNA in example 6 of the present invention.

In order to investigate the applicability of the prepared Alexa Fluor 555-multilabeled RNA as a nucleic acid probe, a series of dot blots were conducted (see FIG. 29). Whereas no signal was observed when the AS chain was immobilized, fluorescence was confirmed in the case of the S chain immobilization, indicating that the Alexa Fluor 555-multilabeled RNA could be used as a probe. Further, because the base sequence specificity is retained, future optimization of the temperature and formamide concentration during the hybridization process can be expected to yield higher sensitivity detection.

The invention claimed is:

1. A nucleoside triphosphate derivative which is represented by formula (5) below:

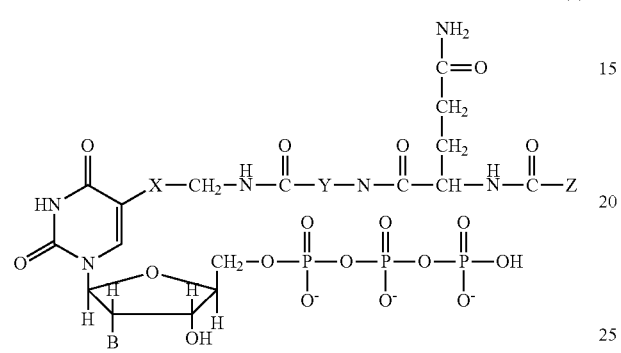

(5)

wherein each of X and Y independently represents a bivalent linking group,
wherein Z represents a substituent, and
wherein B represents a hydrogen atom or a hydroxyl group.

2. The nucleoside triphosphate derivative according to claim 1,
wherein each of X and Y independently represents an alkylene group having a carbon number of 1 to 48 or an alkenylene group having a carbon number of 2 to 48, and
wherein Z represents an alkyl group having a carbon number of 1 to 48, an alkoxy group having a carbon number of 1 to 48, an aryl group having a carbon number of 6 to 48, an aryloxy group having a carbon number of 6 to 48, an arylalkyl group having a carbon number of 7 to 48, or an arylalkyloxy group having a carbon number of 7 to 48.

3. The nucleoside triphosphate derivative according to claim 2,
wherein X represents an ethenylene group,
wherein Y represents a methylene group, and
wherein Z represents a benzyloxy group.

4. A nucleic acid probe, comprising:
a plurality of nucleoside triphosphate derivatives,
wherein each of the plurality of nucleoside triphosphate derivatives is represented by formula (5) below:

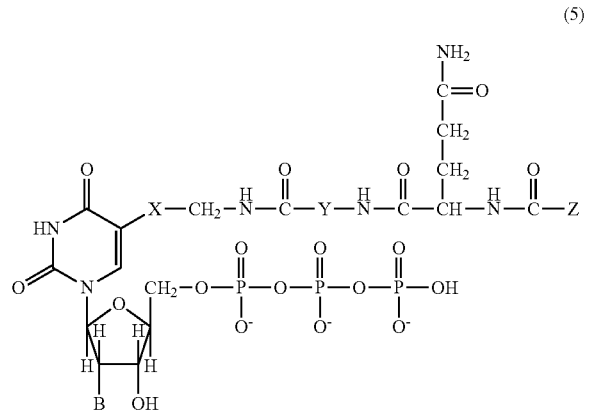

(5)

wherein each of X and Y independently represents a bivalent linking group,
wherein Z represents a substituent, and
wherein B represents a hydrogen atom or a hydroxyl group.

5. A multilabeled nucleic acid probe, comprising:
(1) a nucleic acid probe comprising plurality of nucleoside triphosphate derivatives, each of the plurality of nucleoside triphosphate derivatives having a glutamine residue, and a labeling compound comprising a lysine residue and a labeling portion, or
(2) a nucleic acid probe comprising plurality of nucleoside triphosphate derivatives, each of the plurality of nucleoside triphosphate derivatives having a lysine residue, and a labeling compound comprising a glutamine residue and residue and a labeling portion,
wherein said labeling compound is bound the nucleic acid probe by covalent binding between the glutamine residue and the lysine residue.

6. The multilabeled nucleic acid probe according to claim 5, wherein the labeling portion is at least one of an enzyme and a fluorescent dye.

7. The multilabeled nucleic acid probe according to claim 6, wherein the labeling portion is an enzyme derived from a hyperthermophile.

8. A method for producing a multilabeled nucleic acid probe, the method comprising:
providing either
(1) a nucleic acid probe comprising plurality of nucleoside triphosphate derivatives, each of the plurality of nucleoside triphosphate derivatives having a glutamine residue, and a labeling compound comprising a lysine residue and a labeling portion, or
(2) a nucleic acid probe comprising plurality of nucleoside triphosphate derivatives, each of the plurality of nucleoside triphosphate derivatives having a lysine residue, and a labeling compound comprising a glutamine residue and a labeling portion, and
using a transglutaminase to bind the labeling compound to the nucleic acid probe,
wherein said labeling compound is bound to the nucleic acid probe by covalent binding between the glutamine residue and the lysine residue.

9. The method for producing a multilabeled nucleic acid probe according to claim 8, the labeling portion is at least one of an enzyme and a fluorescent dye.

10. The method for producing a multilabeled nucleic acid probe according to claim 9, wherein the labeling portion is an enzyme derived from a hyperthermophile.

11. A method for detecting a target nucleic acid, the method comprising
performing specific binding, via nucleic acid portions, of the multilabeled nucleic acid probe according to claim 5, and a target nucleic acid, and
detecting the bound multilabeled nucleic acid probe via the labeling portion.

12. A method for detecting a target nucleic acid, the method comprising:
performing specific binding, via nucleic acid portions, of:
a nucleic acid probe comprising a plurality of nucleoside triphosphate derivatives, where either (1) each of the plurality of nucleoside triphosphate derivatives have a glutamine residue, or (2) each of the plurality of nucleoside triphosphate derivatives have a lysine residue, and a target nucleic acid, subsequently introducing a plurality of labeling compounds which either (1) comprise a glutamine residue and a labeling portion, or (2) comprise a lysine residue and a labeling portion, then using a transglutaminase to react the labeling compounds with the nucleic acid probes, and detecting the bound nucleic acid probe via the labeling portions, wherein said labeling compounds are bound to the nucleic acid probe by covalent binding between the glutamine residue and the lysine residue.

* * * * *

SEQUENCE LISTING

<160> NUMBER OF SEQ ID NOS: 37

<210> SEQ ID NO 1
<211> LENGTH: 4
<212> TYPE: PRT
<213> ORGANISM: Artificial
<220> FEATURE:
<223> OTHER INFORMATION: Chemically Synthesized

<400> SEQUENCE: 1

Leu Leu Gln Gly
1

<210> SEQ ID NO 2
<211> LENGTH: 4
<212> TYPE: PRT
<213> ORGANISM: Artificial
<220> FEATURE:
<223> OTHER INFORMATION: Chemically Synthesized

<400> SEQUENCE: 2

Leu Ala Gln Gly
1

<210> SEQ ID NO 3
<211> LENGTH: 4
<212> TYPE: PRT
<213> ORGANISM: Artificial
<220> FEATURE:
<223> OTHER INFORMATION: Chemically Synthesized

<400> SEQUENCE: 3

Leu Gly Gln Gly
1

<210> SEQ ID NO 4
<211> LENGTH: 6
<212> TYPE: PRT
<213> ORGANISM: Artificial
<220> FEATURE:
<223> OTHER INFORMATION: Chemically Synthesized

<400> SEQUENCE: 4

Pro Leu Ala Gln Ser His
1               5

<210> SEQ ID NO 5
<211> LENGTH: 8
<212> TYPE: PRT
<213> ORGANISM: Artificial
<220> FEATURE:
<223> OTHER INFORMATION: Chemically Synthesized

<400> SEQUENCE: 5

Phe Glu Arg Gln His Met Asp Ser
1               5

<210> SEQ ID NO 6
<211> LENGTH: 11
<212> TYPE: PRT
<213> ORGANISM: Artificial
<220> FEATURE:
<223> OTHER INFORMATION: Chemically Synthesized

<400> SEQUENCE: 6

Thr Glu Gln Lys Leu Ile Ser Glu Glu Asp Leu

```
1               5               10

<210> SEQ ID NO 7
<211> LENGTH: 7
<212> TYPE: PRT
<213> ORGANISM: Artificial
<220> FEATURE:
<223> OTHER INFORMATION: Chemically Synthesized

<400> SEQUENCE: 7

Gly Leu Gly Gln Gly Gly Gly
1               5

<210> SEQ ID NO 8
<211> LENGTH: 7
<212> TYPE: PRT
<213> ORGANISM: Artificial
<220> FEATURE:
<223> OTHER INFORMATION: Chemically Synthesized

<400> SEQUENCE: 8

Gly Phe Gly Gln Gly Gly Gly
1               5

<210> SEQ ID NO 9
<211> LENGTH: 7
<212> TYPE: PRT
<213> ORGANISM: Artificial
<220> FEATURE:
<223> OTHER INFORMATION: Chemically Synthesized

<400> SEQUENCE: 9

Gly Val Gly Gln Gly Gly Gly
1               5

<210> SEQ ID NO 10
<211> LENGTH: 7
<212> TYPE: PRT
<213> ORGANISM: Artificial
<220> FEATURE:
<223> OTHER INFORMATION: Chemically Synthesized

<400> SEQUENCE: 10

Gly Gly Leu Gln Gly Gly Gly
1               5

<210> SEQ ID NO 11
<211> LENGTH: 7
<212> TYPE: PRT
<213> ORGANISM: Artificial
<220> FEATURE:
<223> OTHER INFORMATION: Chemically Synthesized

<400> SEQUENCE: 11

Glu Ala Gln Gln Ile Val Met
1               5

<210> SEQ ID NO 12
<211> LENGTH: 7
<212> TYPE: PRT
<213> ORGANISM: Artificial
<220> FEATURE:
<223> OTHER INFORMATION: Chemically Synthesized

<400> SEQUENCE: 12

Gly Gly Gly Gln Leu Gly Gly
1               5
```

```
<210> SEQ ID NO 13
<211> LENGTH: 7
<212> TYPE: PRT
<213> ORGANISM: Artificial
<220> FEATURE:
<223> OTHER INFORMATION: Chemically Synthesized

<400> SEQUENCE: 13

Gly Gly Gly Gln Val Gly Gly
1               5

<210> SEQ ID NO 14
<211> LENGTH: 7
<212> TYPE: PRT
<213> ORGANISM: Artificial
<220> FEATURE:
<223> OTHER INFORMATION: Chemically Synthesized

<400> SEQUENCE: 14

Gly Gly Gly Gln Arg Gly Gly
1               5

<210> SEQ ID NO 15
<211> LENGTH: 6
<212> TYPE: PRT
<213> ORGANISM: Artificial
<220> FEATURE:
<223> OTHER INFORMATION: Chemically Synthesized

<400> SEQUENCE: 15

Gly Gln Gln Gln Leu Gly
1               5

<210> SEQ ID NO 16
<211> LENGTH: 7
<212> TYPE: PRT
<213> ORGANISM: Artificial
<220> FEATURE:
<223> OTHER INFORMATION: Chemically Synthesized

<400> SEQUENCE: 16

Pro Asn Pro Gln Leu Pro Phe
1               5

<210> SEQ ID NO 17
<211> LENGTH: 7
<212> TYPE: PRT
<213> ORGANISM: Artificial
<220> FEATURE:
<223> OTHER INFORMATION: Chemically Synthesized

<400> SEQUENCE: 17

Pro Lys Pro Gln Gln Phe Met
1               5

<210> SEQ ID NO 18
<211> LENGTH: 6
<212> TYPE: PRT
<213> ORGANISM: Artificial
<220> FEATURE:
<223> OTHER INFORMATION: Chemically Synthesized

<400> SEQUENCE: 18

Met Lys His Lys Gly Ser
1               5

<210> SEQ ID NO 19
```

```
<211> LENGTH: 21
<212> TYPE: PRT
<213> ORGANISM: Artificial
<220> FEATURE:
<223> OTHER INFORMATION: Chemically Synthesized

<400> SEQUENCE: 19

Gly Ser Gly Met Lys Glu Thr Ala Ala Ala Arg Phe Glu Arg Ala His
1               5                   10                  15

Met Asp Ser Gly Ser
            20

<210> SEQ ID NO 20
<211> LENGTH: 13
<212> TYPE: PRT
<213> ORGANISM: Artificial
<220> FEATURE:
<223> OTHER INFORMATION: Chemically Synthesized

<400> SEQUENCE: 20

Met Gly Gly Ser Thr Lys His Lys Ile Pro Gly Gly Ser
1               5                   10

<210> SEQ ID NO 21
<211> LENGTH: 5
<212> TYPE: PRT
<213> ORGANISM: Artificial
<220> FEATURE:
<223> OTHER INFORMATION: Chemically Synthesized

<400> SEQUENCE: 21

Gly Gly Gly Gly Gly
1               5

<210> SEQ ID NO 22
<211> LENGTH: 14
<212> TYPE: PRT
<213> ORGANISM: Artificial
<220> FEATURE:
<223> OTHER INFORMATION: Chemically Synthesized

<400> SEQUENCE: 22

Met Lys His Lys Gly Ser Gly Gly Gly Ser Gly Gly Gly Ser
1               5                   10

<210> SEQ ID NO 23
<211> LENGTH: 990
<212> TYPE: RNA
<213> ORGANISM: Artificial
<220> FEATURE:
<223> OTHER INFORMATION: Chemically Synthesized

<400> SEQUENCE: 23
aggugccaau gugguagagc agcugcgagu accaguggau gcccgcaguc ggcuccgcgc      60
cccucgcuuc cguugcagau ugcgcugcag ggaugcugcc cccgccccg ccguccgugc      120 gggcggguge cagcgcggcc agcagcgcgu gcgccaggcg gaaaggcgcg aaggcccggu      180
gugcccagcu gugcuccucg augacagcgu acgacgagge gagcacccgg uugaugagaa      240
uggugccgug cgccgugagc ggcgcguacg cgcccgccuc cuccucucgc agcgucacgc      300
ugugcaccgc ggcgggcagc agccggccggu ccccgccgcg uucagccacc acguacacgc      360
gcugcccggg gcgcacgcgg cuggcaaaga gcgcgcuugg cccgggcgug ggccccgagu      420
cguugugcgg cgccacgaag agcagggcgc ggcggugag cagcaggcgc ucgcgcggcu      480
ccagcgucuc gaucacguag aaguccuucu uggcgccuuc gucgcggucc aggaaggugga     540
```

| | | | | |
|---|---|---|---|---|
| ggaagucgcu | guacagcagc | cggcccuggu | cgucagccgc | cagcacgcgg | ucuccgggac | 600 |
| guaaguccuu | caccagcuug | gugccgcccu | gcuccaggug | cacgguggcg | gaucccggga | 660 |
| aacagccgcc | ggauuuggcc | gccacggagu | cucucugcuuu | cacagaacag | uggaugugag | 720 |
| cuuuggauuc | auaguagacc | cagucgaaac | cugcuuccac | agccaggcga | gccagcaugc | 780 |
| cguacuugcu | gcgguccggg | ucggacgugg | ugauguccac | ugcucgaccc | ucauagugua | 840 |
| gagacucccuc | ugccugaugg | ccguccucau | cccagcccuc | ggucacucgc | agcuucacuc | 900 |
| caggccacug | guucaucaca | gagauggcca | aggcauuuaa | cuugucuuug | caccucugag | 960 |
| ucaucagccg | gucugguccc | guguuuuccu | | | | 990 |

<210> SEQ ID NO 24
<211> LENGTH: 990
<212> TYPE: RNA
<213> ORGANISM: Mus musculus
<220> FEATURE:
<221> NAME/KEY: gene
<222> LOCATION: 1-990
<223> OTHER INFORMATION: Sonic hedgehog (ssh) gene

<400> SEQUENCE: 24

| | | | | | | |
|---|---|---|---|---|---|---|
| aggaaaacac | gggagcagac | cggcugauga | cucagaggug | caaagacaag | uuaaaugccu | 60 |
| uggccaucuc | ugugaugaac | caguggccug | gagugaagcu | gcgagugacc | gagggcuggg | 120 |
| augaggacgg | ccaucauuca | gaggagucuc | uacacuauga | gggucgagca | guggacauca | 180 |
| ccacguccga | ccgggaccgc | agcaaguacg | gcaugcuggc | ucgccuggcu | uggaagcag | 240 |
| guuucgacug | ggucuacuau | gaauccaaag | cucacaucca | cuguucugug | aaagcagaga | 300 |
| acuccgug gc | ggccaaaucc | ggcggcuguu | ucccgggauc | cgccaccgug | caccuggagc | 360 |
| agggcggcac | caagcuggug | aaggacuuac | guccggaga | ccgcgugcug | gcggcugacg | 420 |
| accagggccg | gcugcuguac | agcgacuccc | ucaccuuccu | ggaccgcgac | gaaggcgcca | 480 |
| agaaggucuu | cuacgugauc | gagacgcugg | agccgcgcga | gcgccugcug | cucaccgccg | 540 |
| cgcaccugcu | cuucguggcg | ccgcacaacg | acucgggggcc | cacgcccggg | ccaagcgcgc | 600 |
| ucuuugccag | ccgcgugcgc | cccgggcagc | gcguguacgu | ggugcugaa | cgcggcgggg | 660 |
| accgccggcu | gcugcccgcc | gcggugcaca | gcgugacgcu | gcgagaggag | gaggcgggcg | 720 |
| cguacgcgcc | gcucacggcg | cacggcacca | uucucaucaa | ccgggugcuc | gccucgugcu | 780 |
| acgcugucau | cgaggagcac | agcugggcac | accgggccuu | cgcgccuuuc | cgccuggcgc | 840 |
| acgcgcugcu | ggccgcgcug | gcacccgccc | gcacggacgg | cgggggcggg | ggcagcaucc | 900 |
| cugcagcgca | aucugcaacg | gaagcgaggg | gcgcggagcc | gacugcgggc | auccacuggu | 960 |
| acucgcagcu | gcucuaccac | auuggcaccu | | | | 990 |

<210> SEQ ID NO 25
<211> LENGTH: 990
<212> TYPE: RNA
<213> ORGANISM: Mus musculus
<220> FEATURE:
<221> NAME/KEY: gene
<222> LOCATION: 1-990
<223> OTHER INFORMATION: Sonic hedgehog (ssh) gene

<400> SEQUENCE: 25

| | | | | | | |
|---|---|---|---|---|---|---|
| aggugccaau | gugguagagc | agcugcgagu | accaguggau | gcccgcaguc | ggcuccgcgc | 60 |
| cccucgcuuc | cguugcagau | ugcgcugcag | ggaugcugcc | cccgccccg | ccguccguc | 120 |
| gggcggguge | cagcgcggcc | agcagcgcgu | gcgccaggcg | gaaaggcgcg | aaggcccggu | 180 |

```
gugcccagcu gugcuccucg augacagcgu acgacgaggc gagcacccgg uugaugagaa      240
uggugccgug cgccgugagc ggcgcguacg cgcccgccuc cuccucucgc agcgucacgc      300
ugugcaccgc ggcgggcagc agccggcggu ccccgccgcg uucagccacc acguacacgc      360
gcugcccggg gcgcacgcgg cuggcaaaga gcgcgcuugg cccgggcgug ggccccgagu      420
cguugugcgg cgccacgaag agcaggugcg cggcggugag cagcaggcgc ucgcgcggcu      480
ccagcgucuc gaucacguag aaguccuucu uggcgccuuc gucgcggucc aggaagguga      540
ggaagucgcu guacagcagc cggcccuggu cgucagccgc cagcacgcgg ucuccgggac      600
guaaguccuu caccagcuug gugccgcccu gcuccaggug cacgguggcg gaucccggga      660
aacagccgcc ggauuuggcc gccacggagu cucucugcuuu cacagaacag uggaugugag      720
cuuuggauuc auaguagacc cagucgaaac cugcuuccac agccaggcga gccagcaugc      780
cguacuugcu gcgguccegg ucggacgugg ugaugccac ugcucgaccc ucauagugua      840 gagacucccuc ugccugaugg ccguccucau cccagcccuc ggcacucgc agcuucacuc      900 caggccacug guucaucaca gagauggcca aggcauuuaa cuugucuuug caccucugag      960
ucaucagccg gucuggucccc guguuuuccu                                      990
```

<210> SEQ ID NO 26
<211> LENGTH: 3685
<212> TYPE: DNA
<213> ORGANISM: Artificial
<220> FEATURE:
<223> OTHER INFORMATION: Chemically Synthesized
<400> SEQUENCE: 26

```
acgtgccgat caacgtctca ttttcgccaa aagttggccc agggcttccc ggtatcaaca       60
gggacaccag gatttattta ttctgcgaag tgatcttccg ttcgacggag ttccactgag      120
cgtcagaccc cgtagaaaag atcaaaggat cttcttgaga tcctttttt ctgcgcgtaa      180 tctgctgctt gcaaacaaaa aaaccaccgc taccagcggt ggtttgtttg ccggatcaag      240
agctaccaac tcttttttccg aaggtaactg gcttcagcag agcgcagata ccaaatactg      300
tccttctagt gtagccgtag ttaggccacc acttcaagaa ctctgtagca ccgcctacat      360
acctcgctct gctaatcctg ttaccagtgg ctgctgccag tggcgataag tcgtgtctta      420
ccgggttgga ctcaagacga tagttaccgg ataaggcgca gcggtcgggc tgaacggggg      480
gttcgtgcac acagcccagc ttggagcgaa cgacctacac cgaactgaga tacctacagc      540
gtgagcattg agaaagcgcc acgcttcccg aagggagaaa ggcggacagg tatccggtaa      600
gcggcagggt cggaacagga gagcgcacga gggagcttcc agggggaaac gcctggtatc      660
tttatagtcc tgtcgggttt cgccacctct gacttgagcg tcgatttttg tgatgctcgt      720
caggggggcg gagcctatgg aaaaacgcca gcaacgcggc cttttacgg ttcctggcct      780 tttgctggcc ttttgctcac atgttctttc ctgcgttatc ccctgattct gtggataacc      840
gtattaccgc ctttgagtga gctgataccg ctcgccgcag ccgaacgacc gagcgcagcg      900
agtcagtgag cgaggaagcg gaagaagctc attcgccatt caggctgcgc aactgttggg      960
aagggcgatc ggtgcgggcc tcttcgctat tacgccagct ggcgaagggg ggatgtgctg     1020
caaggcgatt aagttgggta acgccagggt tttcccagtc acgacgttgt aaaacgacgg     1080
ccagtgaatt ccatatgaaa cataaaggcg gaggttcagg tggcggatct ggcagtgctt     1140
acgattctca ggaagtgggg attaaaaata tcattatcct gattggcgac ggtatgggga     1200
tgtcgcacgt gcaaatcacc aaactggttt acggccatct gaacatggag gagttcccta     1260
```

```
ttatcgggtt tgagctgact gaaagcctgt cgggcgaagt caccgatagt gccgcagctg    1320
gtacagcgat tgccaccggg gtaaagacgt ataaccgtat gatttctgtc acgaatatta    1380
caggcaaagt taccaatctg accacgctgc tggagatcgc acaggtcctg ggtaaatcca    1440
ctgggctggt aacaacgacc cgcattactc acgcgacgcc ggcagtattt gcctcgcacg    1500
ttccggaccg tgatatggaa gaggaaatcg cacgccaact gattgctcac cgtgttaacg    1560
tactgctggg tgggggacgc aagaagttcg acgaaaatac cctgaaaatg gctaaggagc    1620
aagggtacaa tatcgtattt actaaagagg aactggaaaa agccgaaggg gagtttatcc    1680
tgggactgtt cgcagacagt cacattccgt acgttctgga ccgtaagccg gaggacgtcg    1740
gactgctgga gatgaccaaa aaagctatct ctattctgga aaagaatccg aacggttttt    1800
tcctgatgat cgaaggtggg cgtattgatc acgcggccca cgagaacgat atcgcaagtg    1860
tcgttgcgga aactaaagag ttcgatgacg tagtgggcta cgtcctggag tatgctaaaa    1920
agcgtggtga tacactggtt attgtcctgg ctgatcacga aacgggggc ctgggtctgg    1980 gcctgacata cggtgacgca atcaacgagg atgtaattcg caatatcaat gcgtcggtat    2040
ccaagatcgc gagcgagatt cgcgccacca acgatattaa acgcgttatt aagaaatata    2100
cagggtttga actgacggag gatgaaatta actatatcga gaggcgatt aacctggcgg    2160 atgaatacgc gctgcaaaac gctattgcag atattattaa taaacgtgtg ggcgtaggtt    2220
ttgtatccca aagcacacg ggggcgccag tctctctgct ggcttatggt ccggggcag    2280 agaacttcgc gggcttttctg caccacgtcg atactgctaa actgatcgcc aaactgatgc    2340
tgttcggtaa gaaagatatt ccggtcacaa ttctgggtat ttctggagtt aaaggtgata    2400
tcaccggcgc actttaaggta gatgaacaag atgcgtacgt cacactgatg atgctgctgg    2460
gtgagcgcgt cgatacggaa ctggaacgta aagtggatat gaataacaat ggaattattg    2520 aactgggga cgtactgctg atcctgcaag agtcgggttc ccaccaccac caccaccact    2580
aaggatccga attcaagctt ggcgtaatca tggtcatagc tgtttcctgt gtgaaattgt    2640
tatccgctca caattccaca acaacatacga gccggaagca taaagtgtaa agcctggggt    2700
gcctaatgag tgagctaact cacattaatt gcgttgcgct cactgcccgc tttccagtcg    2760
ggaaacctgt cgtgccagct gcattaatga atcggccaac gcgcggggag aggcggtttg    2820
cgtattggag cttggcactg gccaagctg aatttctgcc attcatccgc ttattatcac    2880
ttattcaggc gtagcaccag gcgtttaagg gcaccaataa ctgccttaaa aaaattacgc    2940
cccgccctgc cactcatcgc agtactgttg taattcatta agcattctgc cgacatggaa    3000
gccatcacag acggcatgat gaacctgaat cgccagcggc atcagcacct gtcgccttg    3060 cgtataatat ttgcccatgg tgaaaacggg ggcgaagaag ttgtccatat ggccacgtt    3120 taaatcaaaa ctggtgaaac tcacccaggg attggctgag acgaaaaaca tattctcaat    3180
aaacccttta gggaaatagg ccaggttttc accgtaacac gccacatctt gcgaatatat    3240
gtgtagaaac tgccggaaat cgtcgtggta ttcactccag agcgatgaaa cgtttcagt    3300 ttgctcatgg aaaacggtgt aacaagggtg aacactatcc catatcacca gctcaccgtc    3360
tttcattgcc atacgaaatt ccggatgagc attcatcagg cgggcaagaa tgtgaataaa    3420
ggccggataa aacttgtgct tattttttctt tacggtcttt aaaaaggccg taatatccag    3480
ctgaacggtc tggttatagg tacattgagc aactgactga atgcctcaa aatgttcttt    3540 acgatgccat tgggatatat caacggtggt atatccagtg atttttttct ccattttagc    3600
ttccttagct cctgaaaatc tcgataactc aaaaaatacg cccggtagtg atcttatttc    3660
```

```
attatggtga aagttggaac ctctt                                          3685

<210> SEQ ID NO 27
<211> LENGTH: 300
<212> TYPE: DNA
<213> ORGANISM: Mus musculus
<220> FEATURE:
<221> NAME/KEY: gene
<222> LOCATION: 1-300
<223> OTHER INFORMATION: Sonic hedgehog (ssh) gene

<400> SEQUENCE: 27
aggaaaacac gggagcagac cggctgatga ctcagaggtg caaagacaag ttaaatgcct      60
tggccatctc tgtgatgaac cagtggcctg gagtgaagct gcgagtgacc gagggctggg     120
atgaggacgg ccatcattca gaggagtctc tacactatga gggtcgagca gtggacatca     180
ccacgtccga ccgggaccgc agcaagtacg gcatgctggc tcgcctggct gtggaagcag     240
gtttcgactg ggtctactat gaatccaaag ctcacatcca ctgttctgtg aaagcagaga     300

<210> SEQ ID NO 28
<211> LENGTH: 20
<212> TYPE: DNA
<213> ORGANISM: Mus musculus
<220> FEATURE:
<221> NAME/KEY: gene
<222> LOCATION: 1-20
<223> OTHER INFORMATION: Sonic hedgehog (ssh) gene

<400> SEQUENCE: 28
aggaaaacac gggagcagac                                                 20

<210> SEQ ID NO 29
<211> LENGTH: 20
<212> TYPE: DNA
<213> ORGANISM: Mus musculus
<220> FEATURE:
<221> NAME/KEY: gene
<222> LOCATION: 1-20
<223> OTHER INFORMATION: Sonic hedgehog (ssh) gene

<400> SEQUENCE: 29
tctctgcttt cacagaacag                                                 20

<210> SEQ ID NO 30
<211> LENGTH: 990
<212> TYPE: DNA
<213> ORGANISM: Mus musculus
<220> FEATURE:
<221> NAME/KEY: gene
<222> LOCATION: 1-990
<223> OTHER INFORMATION: Sonic hedgehog (ssh) gene

<400> SEQUENCE: 30
aggaaaacac gggagcagac cggctgatga ctcagaggtg caaagacaag ttaaatgcct      60
tggccatctc tgtgatgaac cagtggcctg gagtgaagct gcgagtgacc gagggctggg     120
atgaggacgg ccatcattca gaggagtctc tacactatga gggtcgagca gtggacatca     180
ccacgtccga ccgggaccgc agcaagtacg gcatgctggc tcgcctggct gtggaagcag     240
gtttcgactg ggtctactat gaatccaaag ctcacatcca ctgttctgtg aaagcagaga     300
actccgtggc ggccaaatcc ggcggctgtt tcccgggatc cgccaccgtg cacctggagc     360
agggcggcac caagctggtg aaggacttac gtccggaga ccgcgtgctg gcggctgacg     420
accagggccg gctgctgtac agcgacttcc tcaccttcct ggaccgcgac gaaggcgcca     480
```

| | |
|---|---|
| agaaggtctt ctacgtgatc gagacgctgg agccgcgcga gcgcctgctg ctcaccgccg | 540 |
| cgcacctgct cttcgtggcg ccgcacaacg actcggggcc cacgcccggg ccaagcgcgc | 600 |
| tctttgccag ccgcgtgcgc cccgggcagc gcgtgtacgt ggtggctgaa cgcggcgggg | 660 |
| accgccggct gctgcccgcc gcggtgcaca gcgtgacgct gcgagaggag gaggcgggcg | 720 |
| cgtacgcgcc gctcacggcg cacggcacca ttctcatcaa ccgggtgctc gcctcgtgct | 780 |
| acgctgtcat cgaggagcac agctgggcac accgggcctt cgcgcctttc cgcctggcgc | 840 |
| acgcgctgct ggccgcgctg gcaccccgcc gcacggacgg cggggggcggg ggcagcatcc | 900 |
| ctgcagcgca atctgcaacg gaagcgaggg gcgcggagcc gactgcgggc atccactggt | 960 |
| actcgcagct gctctaccac attggcacct | 990 |

<210> SEQ ID NO 31
<211> LENGTH: 40
<212> TYPE: DNA
<213> ORGANISM: Artificial
<220> FEATURE:
<223> OTHER INFORMATION: Chemically Synthesized and containing
      naturally occuring T7 phage promoter sequence

<400> SEQUENCE: 31

| | |
|---|---|
| taatacgact cactataggg aggtgccaat gtggtagagc | 40 |

<210> SEQ ID NO 32
<211> LENGTH: 1712
<212> TYPE: DNA
<213> ORGANISM: Artificial
<220> FEATURE:
<223> OTHER INFORMATION: Chemically Synthesized

<400> SEQUENCE: 32

| | |
|---|---|
| taatacgact cactataggg gaattgtgag cggataacaa ttcccctcta gaaataattt | 60 |
| tgtttaactt taagaaggag atatacatat gaaacataaa ggcggaggtt caggtggcgg | 120 |
| atctggcagt gcttacgatt ctcaggaaag tgggattaaa aatatcatta tcctgattgg | 180 |
| cgacggtatg gggatgtcgc acgtgcaaat caccaaactg gtttacgcc atctgaacat | 240 |
| ggaggagttc cctattatcg ggtttgagct gactgaaagc ctgtcgggcg aagtcaccga | 300 |
| tagtgccgca gctggtacag cgattgccac cggggtaaag acgtataacc gtatgatttc | 360 |
| tgtcacgaat attacaggca aagttaccaa tctgaccacg ctgctggaga tcgcacaggt | 420 |
| cctgggtaaa tccactgggc tggtaacaac gacccgcatt actcacgcga cgccggcagt | 480 |
| atttgcctcg cacgttccgg accgtgatat ggaagaggaa atcgcacgcc aactgattgc | 540 |
| tcaccgtgtt aacgtactgc tgggtggggg acgcaagaag ttcgacgaaa ataccctgaa | 600 |
| aatggctaag gagcaagggt acaatatcgt atttactaaa gaggaactgg aaaaagccga | 660 |
| aggggagttt atcctgggac tgttcgcaga cagtcacatt ccgtacgttc tggaccgtaa | 720 |
| gccggaggac gtcggactgc tggagatgac caaaaaagct atctctattc tggaaaagaa | 780 |
| tccgaacggt ttttcctga tgatcgaagg tgggcgtatt gatcacgcgg cccacgagaa | 840 |
| cgatatcgca agtgtcgttg cggaaactaa agagttcgat gacgtagtgg gctacgtcct | 900 |
| ggagtatgct aaaaagcgtg gtgatacact ggttattgtc ctggctgatc acgaaacggg | 960 |
| gggcctgggt ctgggcctga catacggtga cgcaatcaac gaggatgtaa ttcgcaatat | 1020 |
| caatgcgtcg gtatccaaga tcgcgagcga gattcgcgcc accaacgata ttaaacgcgt | 1080 |
| tattaagaaa tatacagggt ttgaactgac ggaggatgaa attaactata tcgaagaggc | 1140 |

```
gattaacctg gcggatgaat acgcgctgca aaacgctatt gcagatatta ttaataaacg   1200
tgtgggcgta ggttttgtat cccacaagca cacgggggcg ccagtctctc tgctggctta   1260
tggtccgggg gcagagaact tcgcgggctt tctgcaccac gtcgatactg ctaaactgat   1320
cgccaaactg atgctgttcg gtaagaaaga tattccggtc acaattctgg gtatttctgg   1380
agttaaaggt gatatcaccg gcgactttaa ggtagatgaa caagatgcgt acgtcacact   1440
gatgatgctg ctgggtgagc gcgtcgatac ggaactggaa cgtaaagtgg atatgaataa   1500
caatggaatt attgaactgg gggacgtact gctgatcctg caagagtcgg gttcccacca   1560
ccaccaccac cactaaggat ccgaattcga gctccgtcga caagcttgcg gccgcactcg   1620
agcaccacca ccaccaccac tgagatccgg ctgctaacaa agcccgaaag gaagctgagt   1680
tggctgctgc caccgctgag caataactag ca                                 1712
```

<210> SEQ ID NO 33
<211> LENGTH: 20
<212> TYPE: DNA
<213> ORGANISM: Artificial
<220> FEATURE:
<223> OTHER INFORMATION: Chemically Synthesized

<400> SEQUENCE: 33
taatacgact cactataggg                                                20

<210> SEQ ID NO 34
<211> LENGTH: 20
<212> TYPE: DNA
<213> ORGANISM: Artificial
<220> FEATURE:
<223> OTHER INFORMATION: Chemically Synthesized

<400> SEQUENCE: 34
tgctagttat tgctcagcgg                                                20

<210> SEQ ID NO 35
<211> LENGTH: 6
<212> TYPE: PRT
<213> ORGANISM: Artificial
<220> FEATURE:
<223> OTHER INFORMATION: Chemically Synthesized

<400> SEQUENCE: 35

Met Arg His Lys Gly Ser
1               5

<210> SEQ ID NO 36
<211> LENGTH: 6
<212> TYPE: PRT
<213> ORGANISM: Artificial
<220> FEATURE:
<223> OTHER INFORMATION: Chemically Synthesized

<400> SEQUENCE: 36

Met Arg Arg Lys Gly Ser
1               5

<210> SEQ ID NO 37
<211> LENGTH: 6
<212> TYPE: PRT
<213> ORGANISM: Artificial
<220> FEATURE:
<223> OTHER INFORMATION: Chemically Synthesized

```
<400> SEQUENCE: 37

Met His Arg Lys Gly Ser
1               5
```